(12) United States Patent
Goff et al.

(10) Patent No.: US 7,071,190 B2
(45) Date of Patent: Jul. 4, 2006

(54) INHIBITORS TO TUBULIN POLYMERIZATION

(75) Inventors: Dane Goff, Redwood City, CA (US);
Mark K. Bennett, Moraga, CA (US);
Susan Demo, San Francisco, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 10/369,223

(22) Filed: Feb. 18, 2003

(65) Prior Publication Data

US 2003/0225112 A1 Dec. 4, 2003

Related U.S. Application Data

(60) Provisional application No. 60/357,560, filed on Feb. 15, 2002.

(51) Int. Cl.
*A61K 31/535* (2006.01)

(52) U.S. Cl. .............. 514/234.2; 514/258.1; 514/260.1; 544/117; 544/253; 544/278

(58) Field of Classification Search ........... 544/278, 544/253, 117; 514/234.2, 260.1, 258.1
See application file for complete search history.

(56) References Cited

U.S. PATENT DOCUMENTS

| | | | |
|---|---|---|---|
| 5,942,546 A | 8/1999 | Chern et al. ............. 514/603 |
| 6,133,271 A | 10/2000 | Pamukcu et al. ............. 514/258 |
| 6,169,091 B1 | 1/2001 | Cockerill et al. ............. 514/258 |
| 6,492,383 B1 | 12/2002 | Munchhof et al. ............. 514/301 |
| 6,503,914 B1 | 1/2003 | Benish et al. ............. 514/260.1 |

FOREIGN PATENT DOCUMENTS

| | | |
|---|---|---|
| EP | 0452002 | 3/1991 |
| WO | WO 99/24440 | 5/1999 |
| WO | WO 01/83456 | 11/2001 |
| WO | WO 02/055524 | 7/2002 |
| WO | WO 02/057271 | 7/2002 |
| WO | WO 03/087057 | 10/2003 |
| WO | WO 04/029060 | 4/2004 |
| WO | WO 04/112714 | 12/2004 |

OTHER PUBLICATIONS

Shah et al. Oriental Journal of Chemistry, 2002, 18(1): 159-161.*
Sofina et al. Experimental Evaluation of Antitumor Drugs in the USA and USSR and Clinical Correlations. NCI Monograph 55. NIH Publication No. 80-1933 (1980), pp. 76-78.*
Strandtmann, J. Med. Chem. (1967), 10(6):1063-1065.*
Pettit et al. J. Medicinal Chemistry. 2000, 43: 2731-2737.*
Desbene, Drugs that inhibit tubulin polymerization: the particular case of podophyllotoxin and analogues, PMID: 12678752 (2002).*
Eckardt, Antitumor activity of docetaxel, PMID: 9435925 (1997).*

* cited by examiner

*Primary Examiner*—Amelia A. Owens
(74) *Attorney, Agent, or Firm*—McDonnell Boehnen Hulbert & Berghoff LLP

(57) ABSTRACT

The invention relates to the inhibition of tubulin polymerization. The invention provides compounds and methods for inhibiting tubulin polymerization. The invention also provides compositions and methods for treating cell proliferative diseases and conditions.

22 Claims, 7 Drawing Sheets

INHIBITORS TO TUBULIN POLYMERIZATION

CROSS REFERENCE

This application claims priorty to U.S. Provisional application No. 60/357,560 filed Feb. 15, 2002.

FIELD OF THE INVENTION

This invention relates to the inhibition of tubulin polymerization. More particularly, the invention relates to compounds and methods for inhibiting the polymerization of tubulin.

BACKGROUND OF THE INVENTION

Microtubules are intracellular, filamentous, polymeric structures, present in eukaryotic cells, that extend throughout the cytoplasm and govern the location of membrane-bounded organelles and other cell components. Microtubules are involved in many cellular functions including chromosome migration during mitosis, organelle transport, cytokinesis, cell plate formation, cell motility, and maintenance of cell shape. Microtubules are composed of molecules of tubulin protein, each molecule of which is a heterodimer of α-tubulin and β-tubulin.

Mitosis is the process by which eukaryotic cells ensure the distribution of their chromosomes into two daughter cells during cell division. During this process, the cytoplasmic microtubules are disrupted and reformed as a (mitotic) spindle consisting of large numbers of short microtubules that surround each centrosome. As mitosis proceeds, the elongating ends of the microtubules attach to the chromosomes, the chromosomes align on the metaphase plate, and, during anaphase, the sister chromatids are separated. If any of these stages of chromosomal alignment and separation is disrupted by irregular microtubules, mitosis fails.

Implicit in this mechanism of microtubule-based chromosome migration and separation is that microtubules are labile structures. Further, that lability is critical for their function. The lability manifests through rapid polymerization and depolymerization of the microtubules, which enables cell-scale movements of the chromosomes during mitosis. Even when the mitotic spindle, and the microtubules from which it is made, appears macroscopically inert, tubulin subunits freely exchange on the microtubules. If such free exchange of tubulin subunits is disrupted, the mitotic spindle is compromised and the cell cannot divide. Certain drugs exploit the necessity of tubulin free-exchange in mitosis and act therapeutically by disrupting the delicate balance between microtubule polymerization and depolymerization. Some drugs bind to tubulin subunits, preventing them from being incorporated into a growing microtubule while others bind to the microtubule itself, preventing additional tubulin subunits from binding. As a consequence of either activity, cells undergoing division, and particularly those cells demonstrating aberrant, rapid division, i.e., cancer cells, are killed.

Anticancer drugs that act by binding to tubulin or to microtubules include the alkaloids vincristine and vinblastine, and the taxane-based compounds paclitaxel and docetaxel (see, for example, E. K. Rowinsky and R. C. Donehower, Pharmacology and Therapeutics, 52, 35–84 (1991)). Other antitubulin compounds active against mammalian cells include benzimidazoles such as nocodazole and natural products such as colchicine.

There remains a need in the art for effective, minimally toxic, easily obtained, cytotoxic agents for use in cancer therapy. There remains a need in the art for chemical compounds capable of inhibiting cellular mitosis for use in cancer therapy. Further there remains a need in the art for pharmaceutical compositions for use in cancer therapy. Still further, there remains a need in the art for methods of inhibiting microtubule polymerization and methods of cancer therapy. The present invention provides such embodiments.

BRIEF SUMMARY OF THE INVENTION

The invention provides compounds and methods for treating cell proliferative diseases. The invention provides new inhibitors of tubulin polymerization.

In a first aspect, the invention provides compounds that are useful as inhibitors of tubulin polymerization.

In a second aspect, the invention provides a composition comprising an inhibitor of tubulin polymerization according to the invention and a pharmaceutically acceptable carrier, excipient, or diluent.

In a third aspect, the invention provides a method of inhibiting tubulin polymerization in a cell, comprising contacting a cell in which inhibition of tubulin polymerization is desired with an inhibitor of tubulin polymerization of the invention.

In a fourth aspect, the invention provides a method for treating cell proliferative diseases or conditions, comprising administering to a patient in need thereof an effective amount of an inhibitor of tubulin polymerization of the invention.

The foregoing merely summarizes certain aspects of the invention and is not intended to be limiting in nature. These aspects and other aspects and embodiments are described more fully below.

DETAILED DESCRIPTION OF THE PREFERRED EMBODIMENTS

Figure 1A:
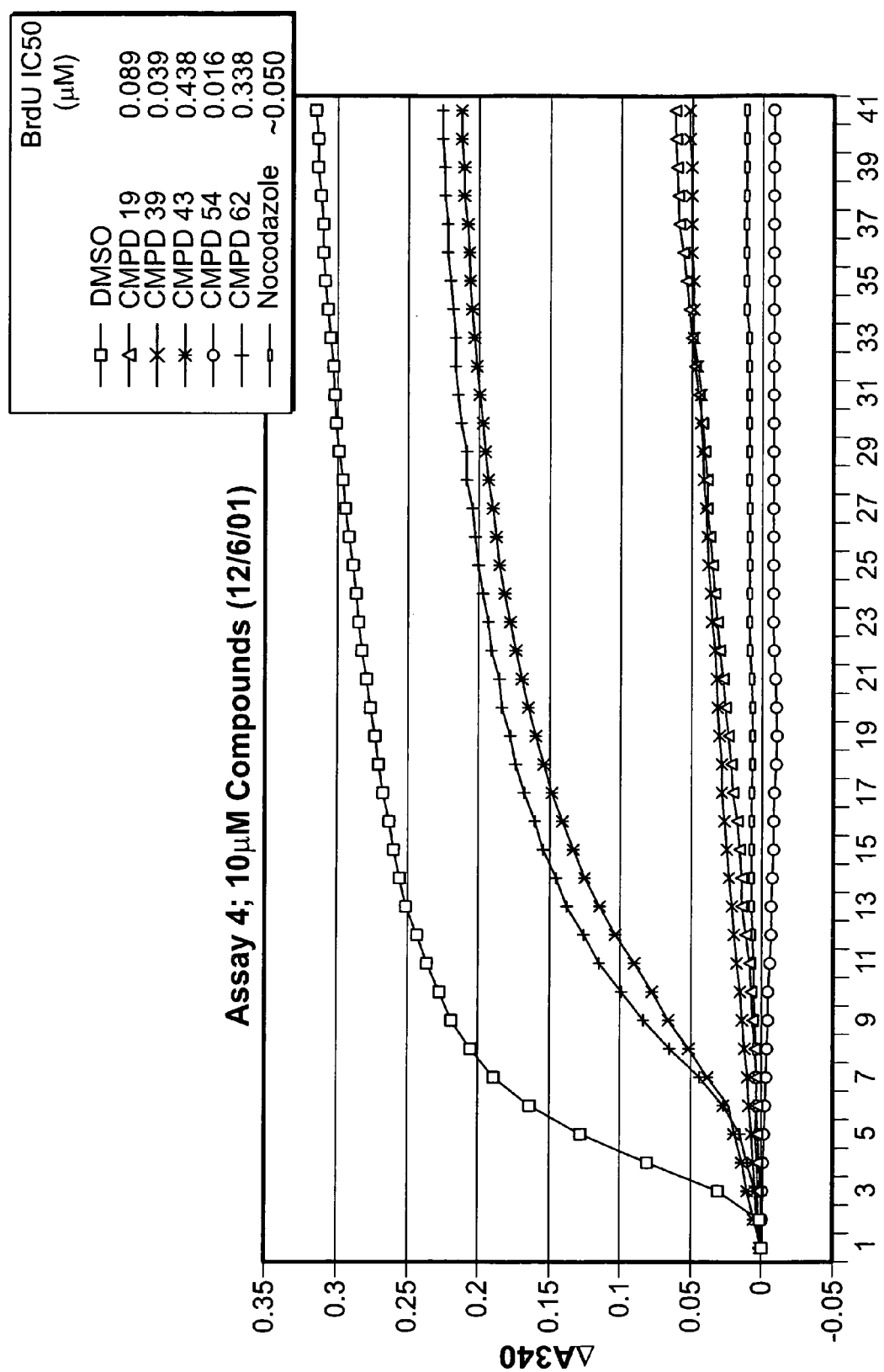
FIG. 1. Tubulin polymerization inhibitory activity of the compounds of the invention was assayed by following the turbidity of a tubulin-containing solution over time. Polymerization of tubulin generates microtubules, the presence of which increases the absorbance of the assay solution over time. Effective inhibition manifests as a reduction of rate of absorbance increase at 340 nanometers. (a) 10 µM of compounds 19, 39, 43, 54 and 62, as well as 10 µM nocodazole as a positive control and DMSO as a negative control. (b) 10 µM of compounds 1, 88, 95, and 54, as well as 10 µM as well a positive controls 1 and 2 and DMSO as a negative control. (c) 0.4, 2.0 and 10 µM compound 54 versus 0.4, 2.0 and 10 µM nocodazole as a positive control and DMSO as a negative control. Inhibition activity is observed for each compound.

The invention provides compounds and methods for inhibiting tubulin polymerization. The invention also provides compositions and methods for treating cell proliferative diseases and conditions. The patent and scientific literature referred to herein establishes knowledge that is available to those with skill in the art. The issued patents, applications, and references that are cited herein are hereby incorporated by reference to the same extent as if each was specifically and individually indicated to be incorporated by reference. In the case of inconsistencies, the present disclosure will prevail.

For purposes of the present invention, the following definitions will be used (unless expressly stated otherwise):

As used herein, the term "tubulin polymerization" refers to the polymerization of tubulin to form microtubules.

The term "tubulin polymerization inhibitor" is used to identify a compound having a structure as defined herein, which is capable of interacting with tubulin and inhibiting its polymerization. "Inhibiting tubulin polymerization" means reducing the ability of tubulin to form microtubules.

Preferably, such inhibition is specific, i.e., the tubulin polymerization inhibitor reduces the ability of tubulin to polymerize at a concentration that is lower than the concentration of the inhibitor that is required to produce another, unrelated biological effect. Preferably, the concentration of the inhibitor required for tubulin polymerization inhibitory activity is at least 2-fold lower, more preferably at least 5-fold lower, even more preferably at least 10-fold lower, and most preferably at least 20-fold lower than the concentration required to produce an unrelated biological effect.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g. $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene.) All atoms are understood to have their normal number of valences for bond formation (i.e., 4 for carbon, 3 for N, 2 for O, and 2, 4, or 6 for S, depending on the oxidation state of the S). On occasion a moiety may be defined, for example, as $(A)_a$-B—, wherein a is 0 or 1. In such instances, when a is 0 the moiety is B— and when a is 1 the moiety is A-B—. Also, a number of moieties disclosed herein exist in multiple tautomeric forms, all of which are intended to be encompassed by any given tautomeric structure.

The term "hydrocarbyl" refers to a straight, branched, or cyclic alkyl, alkenyl, or alkynyl, each as defined herein. A "$C_0$" hydrocarbyl is used to refer to a covalent bond. Thus, "$C_0$–$C_3$-hydrocarbyl" includes a covalent bond, methyl, ethyl, propyl, and cyclopropyl.

The term "alkyl" as employed herein refers to straight and branched chain aliphatic groups having from 1 to 12 carbon atoms, preferably 1–8 carbon atoms, and more preferably 1–6 carbon atoms, which is optionally substituted with one, two or three substituents. Preferred alkyl groups include, without limitation, methyl, ethyl, propyl, isopropyl, butyl, isobutyl, sec-butyl, tert-butyl, pentyl, and hexyl. A "$C_0$" alkyl (as in "$C_0$–$C_3$-alkyl") is a covalent bond (like "$C_0$" hydrocarbyl).

The term "halogenated alkyl" as employed herein refers to an "alkyl" as defined above that is mono- to per-halogenated, but preferably having from 1–3 halo substituents.

The term "alkenyl" as used herein means an unsaturated straight or branched chain aliphatic group with one or more carbon-carbon double bonds, having from 2 to 12 carbon atoms, preferably 2–8 carbon atoms, and more preferably 2–6 carbon atoms, which is optionally substituted with one, two or three substituents. Preferred alkenyl groups include, without limitation, ethenyl, propenyl, butenyl, pentenyl, and hexenyl.

The term "alkynyl" as used herein means an unsaturated straight or branched chain aliphatic group with one or more carbon-carbon triple bonds, having from 2 to 12 carbon atoms, preferably 2–8 carbon atoms, and more preferably 2–6 carbon atoms, which is optionally substituted with one, two or three substituents. Preferred alkynyl groups include, without limitation, ethynyl, propynyl, butynyl, pentynyl, and hexynyl.

An "alkylene," "alkenylene," or "alkynylene" group is an alkyl, alkenyl, or alkynyl group, as defined hereinabove, that is positioned between and serves to connect two other chemical groups. Preferred alkylene groups include, without limitation, methylene, ethylene, propylene, and butylene. Preferred alkenylene groups include, without limitation, ethenylene, propenylene, and butenylene. Preferred alkynylene groups include, without limitation, ethynylene, propynylene, and butynylene.

The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group additionally is optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroalkyl" refers to an alkyl group, as defined hereinabove, wherein one or more carbon atoms in the chain are replaced by a heteroatom selected from the group consisting of O, S, and N.

An "aryl" group is a $C_6$–$C_{14}$ aromatic moiety comprising one to three aromatic rings, which is optionally substituted. Preferably, the aryl group is a $C_6$–$C_{10}$ aryl group. Preferred aryl groups include, without limitation, phenyl, naphthyl, anthracenyl, and fluorenyl. An "aralkyl" or "arylalkyl" group comprises an aryl group covalently linked to an alkyl group, either of which may independently be optionally substituted or unsubstituted. Preferably, the aralkyl group is $(C_1$–$C_6)$alk$(C_6$–$C_{10})$aryl, including, without limitation, benzyl, phenethyl, and naphthylmethyl.

A "heterocyclyl" or "heterocyclic" group is a ring structure having from about 3 to about 8 atoms, wherein one or more atoms are selected from the group consisting of N, O, and S. The heterocyclic group is optionally substituted on carbon at one or more positions. The heterocyclic group is also independently optionally substituted on nitrogen with alkyl, aryl, aralkyl, alkylcarbonyl, alkylsulfonyl, arylcarbonyl, arylsulfonyl, alkoxycarbonyl, aralkoxycarbonyl, or on sulfur with oxo or lower alkyl. Preferred heterocyclic groups include, without limitation, epoxy, aziridinyl, tetrahydrofuranyl, pyrrolidinyl, piperidinyl, piperazinyl, thiazolidinyl, oxazolidinyl, oxazolidinonyl, and morpholino. In certain preferred embodiments, the heterocyclic group is fused to an aryl, heteroaryl, or cycloalkyl group. Examples of such fused heterocyles include, without limitation, tetrahydroquinoline and dihydrobenzofuran. Specifically excluded from the scope of this term are compounds having adjacent annular O and/or S atoms.

As used herein, the term "heteroaryl" refers to groups having 5 to 14 ring atoms, preferably 5, 6, 9, or 10 ring atoms; having 6, 10, or 14 π electrons shared in a cyclic array; and having, in addition to carbon atoms, from one to three heteroatoms per ring selected from the group consisting of N, O, and S. A "heteroaralkyl" or "heteroarylalkyl" group comprises a heteroaryl group covalently linked to an alkyl group, either of which is independently optionally substituted or unsubstituted. Preferred heteroalkyl groups comprise a $C_1$–$C_6$ alkyl group and a heteroaryl group having 5, 6, 9, or 10 ring atoms. Specifically excluded from the scope of this term are compounds having adjacent annular O and/or S atoms. Examples of preferred heteroaralkyl groups include pyridylmethyl, pyridylethyl, pyrrolylmethyl, pyrrolylethyl, imidazolylmethyl, imidazolylethyl, thiazolylmethyl, and thiazolylethyl. Specifically excluded from the scope of this term are compounds having adjacent annular O and/or S atoms.

An "arylene," "heteroarylene," or "heterocyclylene" group is an aryl, heteroaryl, or heterocyclyl group, as defined hereinabove, that is positioned between and serves to connect two other chemical groups.

Preferred heterocyclyls and heteroaryls include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

As employed herein, when a moiety (e.g., cycloalkyl, hydrocarbyl, aryl, heteroaryl, heterocyclic, urea, etc.) is described as "optionally substituted" it is meant that the group optionally has from one to four, preferably from one to three, more preferably one or two, non-hydrogen substituents. Suitable substituents include, without limitation, halo, hydroxy, oxo (e.g., an annular —CH— substituted with oxo is —C(O)—) nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Preferred substituents, which are themselves not further substituted (unless expressly stated otherwise) are:

(a) halo, cyano, oxo, carboxy, formyl, nitro, amino, amidino, guanidino, (b) $C_1$–$C_5$ alkyl or alkenyl or arylalkyl imino, carbamoyl, azido, carboxamido, mercapto, hydroxy, hydroxyalkyl, alkylaryl, arylalkyl, $C_1$–$C_8$ alkyl, $C_1$–$C_8$ alkenyl, $C_1$–$C_8$ alkoxy, $C_1$–$C_8$ alkoxycarbonyl, aryloxycarbonyl, $C_2$–$C_8$ acyl, $C_2$–$C_8$ acylamino, $C_1$–$C_8$ alkylthio, arylalkylthio, arylthio, $C_1$–$C_8$ alkylsulfinyl, arylalkylsulfinyl, arylsulfinyl, $C_1$–$C_8$ alkylsulfonyl, arylalkylsulfonyl, arylsulfonyl, $C_0$–$C_6$ N-alkyl carbamoyl, $C_2$–$C_{15}$ N,N-dialkylcarbamoyl, $C_3$–$C_7$ cycloalkyl, aroyl, aryloxy, arylalkyl ether, aryl, aryl fused to a cycloalkyl or heterocycle or another aryl ring, $C_3$–$C_7$ heterocycle, or any of these rings fused or spiro-fused to a cycloalkyl, heterocyclyl, or aryl, wherein each of the foregoing is further optionally substituted with one more moieties listed in (a), above; and (c) —$(CH_2)_s$—$NR^{30}R^{31}$, wherein s is from 0 (in which case the nitrogen is directly bonded to the moiety that is substituted) to 6, and $R^{30}$ and $R^{31}$ are each independently hydrogen, cyano, oxo, carboxamido, amidino, $C_1$–$C_8$ hydroxyalkyl, $C_1$–$C_3$ alkylaryl, aryl-$C_1$–$C_3$ alkyl, $C_1$–$C_8$ alkyl, $C_1$–$C_8$ alkenyl, $C_1$–$C_8$ alkoxy, $C_1$–$C_8$ alkoxycarbonyl, aryloxycarbonyl, aryl-$C_1$–$C_3$ alkoxycarbonyl, $C_2$–$C_8$ acyl, $C_1$–$C_8$ alkylsulfonyl, arylalkylsulfonyl, arylsulfonyl, aroyl, aryl, cycloalkyl, heterocyclyl, or heteroaryl, wherein each of the foregoing is further optionally substituted with one more moieties listed in (a), above; or $R^{30}$ and $R^{31}$ taken together with the N to which they are attached form a heterocyclyl or heteroaryl, each of which is optionally substituted with from 1 to 3 substituents from (a), above.

In addition, substituents on cyclic moieties (i.e., cycloalkyl, heterocyclyl, aryl, heteroaryl) include 5–6 membered mono- and 10–12 membered bi-cyclic moieties fused to the parent cyclic moiety to form a bi- or tri-cyclic fused ring system. For example, an optionally substituted phenyl includes the following:

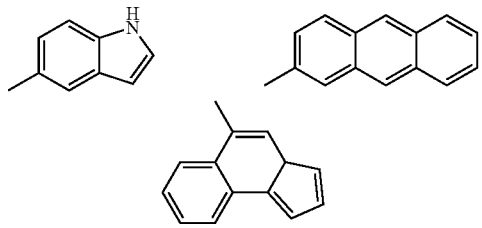

A "halohydrocarbyl" is a hydrocarbyl moiety in which from one to all hydrogens have been replaced with one or more halo.

The term "halogen" or "halo" as employed herein refers to chlorine, bromine, fluorine, or iodine. As herein employed, the term "acyl" refers to an alkylcarbonyl or arylcarbonyl substituent. The term "acylamino" refers to an amide group attached at the nitrogen atom (i.e., R—CO—

NH—). The term "carbamoyl" refers to an amide group attached at the carbonyl carbon atom (i.e., $NH_2$—CO—). The nitrogen atom of an acylamino or carbamoyl substituent is additionally substituted. The term "sulfonamido" refers to a sulfonamide substituent attached by either the sulfur or the nitrogen atom. The term "amino" is meant to include $NH_2$, alkylamino, arylamino, and cyclic amino groups. The term "ureido" as employed herein refers to a substituted or unsubstituted urea moiety.

The term "radical" as used herein means a chemical moiety comprising one or more unpaired electrons.

A moiety that is substituted is one in which one or more hydrogens have been independently replaced with another chemical substituent. As a non-limiting example, substituted phenyls include 2-flurophenyl, 3,4-dichlorophenyl, 3-chloro-4-fluoro-phenyl, 2-fluor-3-propylphenyl. As another non-limiting example, substituted n-octyls include 2,4 dimethyl-5-ethyl-octyl and 3-cyclopentyl-octyl. Included within this definition are methylenes (—$CH_2$—) substituted with oxygen to form carbonyl —CO—).

An "unsubstituted" moiety as defined above (e.g., unsubstituted cycloalkyl, unsubstituted heteroaryl, etc.) means that moiety as defined above that does not have any of the optional substituents for which the definition of the moiety (above) otherwise provides. Thus, for example, while an "aryl" includes phenyl and phenyl substituted with a halo, "unsubstituted aryl" does not include phenyl substituted with a halo.

Preferred embodiments of a particular genus of compounds of the invention include combinations of preferred embodiments. In a non-limiting example, paragraph [0048] identifies a preferred $R^2$ and paragraph [0052] identifies a preferred L (for general formula (1) of paragraph [0047]). Thus, another preferred embodiment includes, for example, those compounds of general formula (1) in paragraph [0047] in which $R^2$ is as defined in paragraph [0048] and L is as defined in paragraph [0052].

Compounds

In a first aspect, the invention provides novel inhibitors of tubulin polymerization. The novel inhibitors of tubulin polymerization are represented by general formula (1):

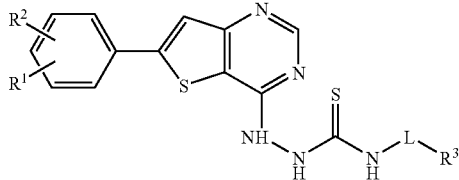

(1)

and pharmaceutically acceptable salts thereof, wherein $R^1$ and $R^2$ are independently selected from the group consisting of —H, halo, $C_1$–$C_6$ alkyl, halogenated $C_1$–$C_6$-alkyl, and —$OR^4$, $R^4$ is selected from the group consisting of $C_1$–$C_6$ alkyl, optionally substituted aryl, and optionally substituted aryl-$C_1$–$C_6$-alkyl, or wherein $R^1$ and $R^2$ together with the carbon to which they are attached form a heterocyclyl;

L is selected from the group consisting of a covalent bond, $C_1$–$C_6$ alkyl, —C(O)—, and —$(CH_2)_{0-3}$C(H)($R^5$)—, $R^5$ is selected from the group consisting of $C_1$–$C_6$ alkyl, aryl, aryl-$C_1$–$C_6$-alkyl, —$R^6$—S—$R^7$, —$R^6$—C(O) $OR^7$, and —$R^6$—O—$R^7$, wherein $R^6$ and $R^7$ are $C_1$–$C_6$ alkyl; and $R^3$ is selected from the group consisting of H, $C_1$–$C_6$ alkyl, hydroxy $C_1$–$C_6$ alkyl, optionally substituted $C_3$–$C_8$-cycloalkyl, optionally substituted heterocyclyl, optionally substituted aryl, optionally substituted heteroaryl, optionally substituted aryl-$C_1$–$C_6$-alkyl, —$OR^8$, —C(O)$OR^9$, —$N(R^{10})R^{11}$, $R^8$ is $C_1$–$C_6$ alkyl or hydroxy $C_1$–$C_6$ alkyl, and $R^9$, $R^{10}$, and $R_{11}$ are $C_1$–$C_6$ alkyl.

In some preferred embodiments of the invention, in the compounds of general formula (1) $R^2$ is H.

In some embodiments of the compounds of general formula (1), $R^1$ and $R^2$ are independently selected from the group consisting of —H, halo, $C_1$–$C_6$ alkyl, halogenated-$C_1$–$C_6$-alkyl, and —$OR^4$ or $R^1$ and $R^2$ together with the carbon to which they are attached form a heterocyclyl. In these embodiments, $R^4$ is preferably selected from the group consisting of $C_1$–$C_6$ alkyl, optionally substituted aryl, and optionally substituted aryl-$C_1$–$C_6$-alkyl.

In a preferred embodiment, $R^1$ and $R^2$ are independently selected from the group consisting of —H, halo, $C_1$–$C_6$ alkyl, and —$OR^4$ and $R^4$ is $C_1$–$C_6$ alkyl, or $R^1$ and $R^2$ together with the carbon to which they are attached form a heterocyclyl moiety. In a more preferred embodiment, $R^1$ and $R^2$ are independently selected from the group consisting —H, —Cl, —$CH_3$, and —$OCH_3$ or $R^1$ and $R^2$ together with the carbon to which they are attached form a 5- or 6-membered heterocyclyl moiety. In a most preferred embodiment, $R^1$ and $R^2$ are both —H.

In some embodiments of the compounds of general formula (1), L is selected from the group consisting of a covalent bond, $C_1$–$C_6$ alkyl, —C(O)—, and —$(CH_2)_{0-3}$C(H)($R^5$)—.

In a preferred embodiment, L is a covalent bond, represented by general formula (2):

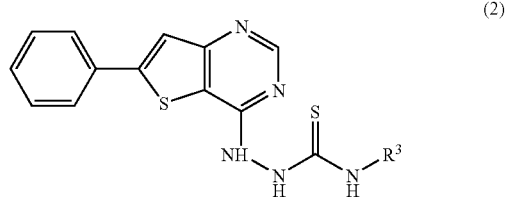

(2)

In a preferred embodiment of the compounds of general formula (2), $R^3$ is selected from the group consisting of H, hydroxy $C_1$–$C_6$ alkyl, optionally substituted cycloalkyl, optionally substituted heterocyclyl, optionally substituted aryl, and optionally substituted heteroaryl. In a more preferred embodiment, $R^3$ is selected from the group consisting of —H, optionally substituted $C_3$–$C_6$ cycloalkyl, optionally substituted $C_5$–$C_6$ heterocyclyl, and optionally substituted aryl. In a most preferred embodiment, $R^3$ is cyclopropyl, benzyl, or substituted benzyl.

In a most preferred embodiment of the compounds of paragraph [0053], $R^3$ is benzyl singly, doubly, or triply substituted with substituents independently selected from the group consisting of —$CH_3$, —$CO_2H$, —$CO_2CH_2CH_3$, —$OCH_3$, —$CF_3$, —CN, —$NO_2$, —$SO_2NH_2$, and —Cl.

In another preferred embodiment of the compounds of general formula (1), L is $C_1$–$C_6$ straight or branched chain alkyl, represented by general formula (3), where n is 1–6:

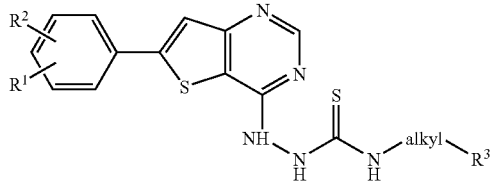

(3)

In a preferred embodiment of the compounds of general formula (3), L is a straight chain alkyl. In a more preferred embodiment, n is 1, 2, or 3.

In a preferred embodiment of the compounds of general formula (3), $R^3$ is selected from the group consisting of —H, optionally substituted $C_3$–$C_8$-cycloalkyl, optionally substituted heterocyclyl, optionally substituted aryl, optionally substituted heteroaryl, —$OR^8$, —$C(O)OR^9$, and —$N(R^{10})R^{11}$, where $R^8$ is $C_1$–$C_6$ alkyl or hydroxy $C_1$–$C_6$ alkyl, and $R^9$, $R^{10}$, and $R^{11}$ are $C_1$–$C_6$ alkyl. In a more prefffered embodiment, $R^3$ is selected from the group consisting of —H, $C_3$–$C_6$ cycloalkyl, $C_4$–$C_6$ heterocyclyl, optionally substituted benzyl, and —$OR^8$. In a more preferred embodiment, $R^8$ is —$CH_3$ or hydroxy alkyl.

In a most preferred embodiment of the compounds of paragraph [0057], $R^3$ is —H, optionally substituted $C_5$–$C_6$ heterocyclyl, optionally substituted benzyl, or —$OCH_3$.

In another preferred embodiment of the compounds of general formula (1), L is —$(CH_2)_{0-3}C(H)(R^5)$—, where $R^5$ is selected from the group consisting of $C_1$–$C_6$ alkyl, aryl, aryl-$C_1$–$C_6$-alkyl, —$R^6$—S—$R^7$, —$R^6$—$C(O)OR^7$, and —$R^6$—O—$R^7$, and where $R^6$ and $R^7$ are $C_1$–$C_6$ alkyl. In a more preferred embodiments L is —$(CH_2)_{0-1}C(H)(R^5)$—. These embodiments are represented by general formula (4):

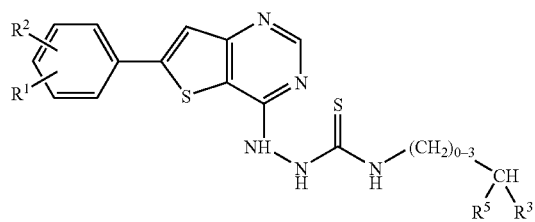

(4)

In a preferred embodiment of the compounds of paragraph [0047], the inhibitors of tubulin polymerization of the invention comprise the following compounds of formula (1), where the notation "CB" is defined as "covalent bond":

| R¹ | R² | L | R³ |
|---|---|---|---|
| H | H | CB | phenyl |
| H | H | CB | 3-methylphenyl |
| H | H | CB | 4-trifluoromethylphenyl |
| H | H | CB | 2-trifluoromethylphenyl |
| H | H | CB | 3-methoxyphenyl |

-continued

| R¹ | R² | L | R³ |
|---|---|---|---|
| H | H | CB | 2-methoxyphenyl (OCH₃ ortho to methyl) |
| H | H | CB | 3-(CO₂H)phenyl |
| H | H | CB | 2-(CO₂CH₂CH₃)phenyl |
| H | H | CB | 4-cyanophenyl |
| H | H | CB | 3-cyanophenyl |
| H | H | CB | 3-nitrophenyl |
| H | H | CB | 4-(SO₂NH₂)phenyl |
| H | H | CB | 2-methyl-5-methoxy-phenyl with additional OCH₃ |
| H | H | CB | 2,3-dimethoxyphenyl (methyl substituted) |
| H | H | CB | 2,3-dimethoxyphenyl (4-methyl) |

-continued
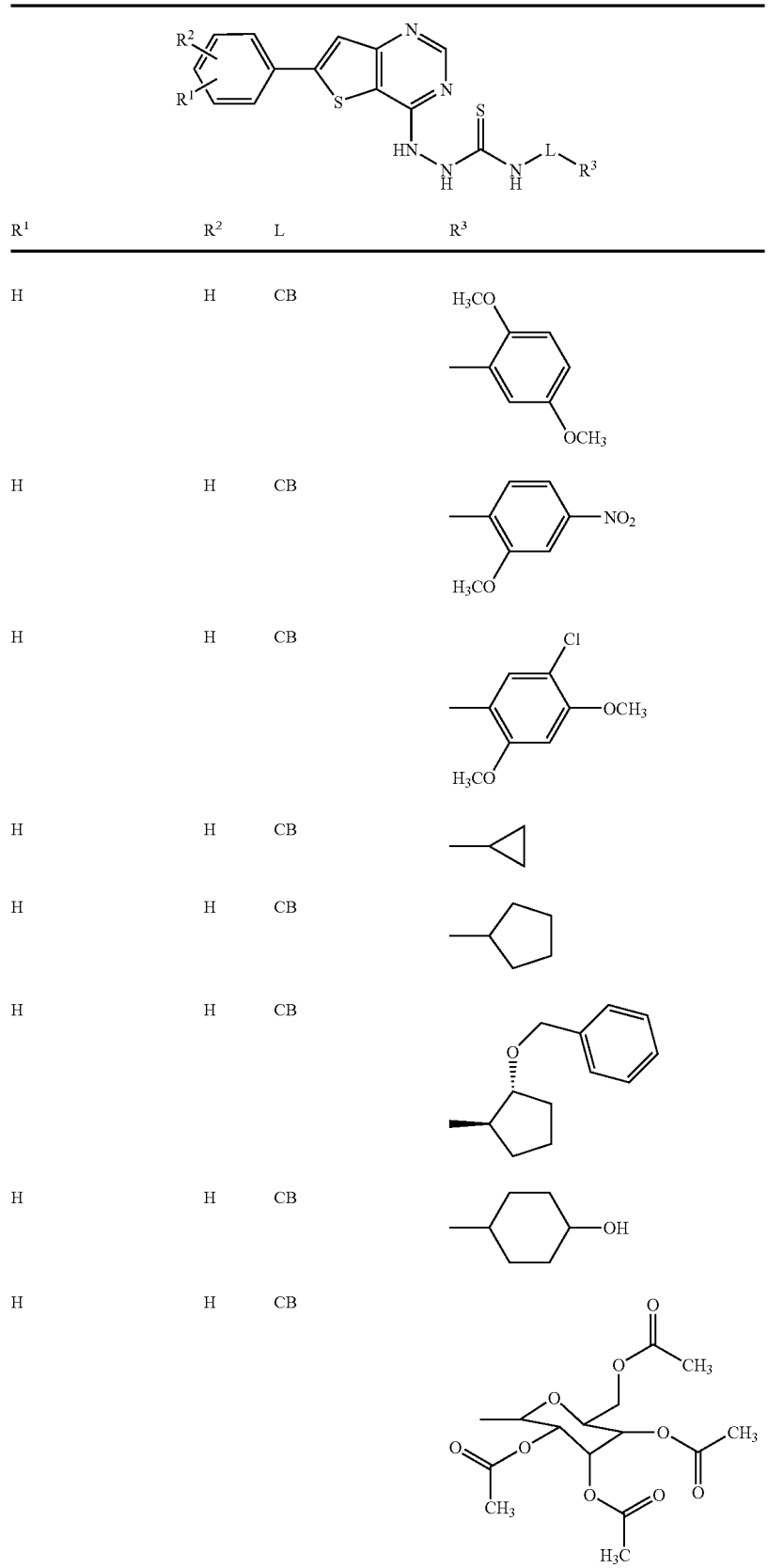

-continued
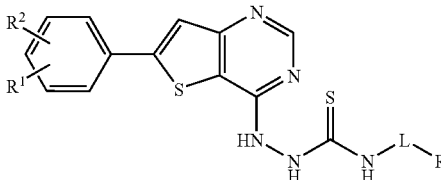
| R¹ | R² | L | R³ |
|---|---|---|---|
| H | H | CB | 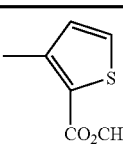 |
| H | H | CB | 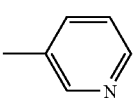 |
| H | H | CB | H |
| H | H | CB | 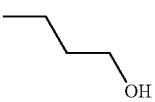 |
| H | H | CB | 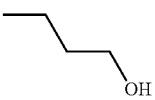 |
| H | H | CB | 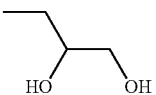 |
| —CH₃ | H | CB | H |
| —CH₃ | H | CB | 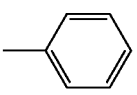 |
| —CF₃ | H | CB | 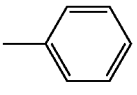 |
| —OCH₃ | H | CB | 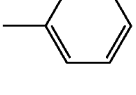 |
| —Cl | H | CB | 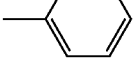 |
| 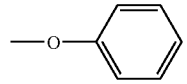 | H | CB | 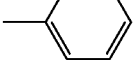 |
| 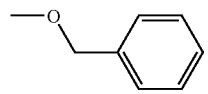 | H | CB | 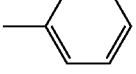 |
| —CH₃ | H | CB |  |

-continued

| R¹ | R² | L | R³ |
|---|---|---|---|
| —OCH₃ | H | CB | cyclopropyl |
| —Cl | H | CB | cyclopropyl |
| —O-phenyl | H | CB | cyclopropyl |
| —O-CH₂-phenyl | H | CB | cyclopropyl |
| —CH₃ | H | CB | cyclopentyl |
| —CH₃ | H | CB | trans-2-(benzyloxy)cyclopentyl |
| —CH₃ | H | CB | —CH₂CH₂CH₂OH |
| —CH₃ | H | CB | —CH₂CH(OH)CH₂OH |
| —CH₃ | —CH₃ | CB | phenyl |
| | 1,3-dioxolane | CB | phenyl |
| | 1,3-dioxane | CB | phenyl |
| —CH₃ | —CH₃ | CB | cyclopropyl |
| | 1,3-dioxolane | CB | cyclopropyl |

-continued

[Structure: 6-aryl-thieno[3,2-d]pyrimidine with 4-position substituted by HN-NH-C(=S)-NH-L-R³; aryl bears R¹ and R²]

| R¹ | R² | L | R³ |
|---|---|---|---|
| H | H | —CH₂— | phenyl |
| H | H | —(CH₂)₂— | phenyl |
| H | H | —(CH₂)₃— | phenyl |
| H | H | —CH₂— | 4-methoxyphenyl |
| H | H | —CH₂— | 4-chlorophenyl |
| H | H | —CH₂— | cyclopropyl |
| H | H | —CH₂— | tetrahydrofuran-2-yl |
| H | H | —CH₂— | (2S)-tetrahydrofuran-2-yl |
| H | H | —CH₂— | (2R)-tetrahydrofuran-2-yl |
| H | H | —CH₂— | 2,2-dimethyl-1,3-dioxolan-4-yl |
| H | H | —CH₂— | piperidin-1-yl |
| H | H | —(CH₂)₂— | morpholin-4-yl |
| H | H | —CH₂— | furan-2-yl |
| H | H | —CH₂— | H |
| H | H | —(CH₂)₃— | H |

-continued

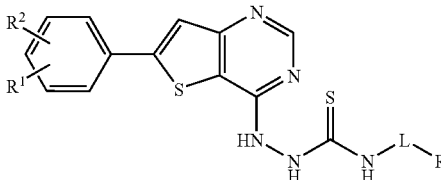

| R¹ | R² | L | R³ |
|---|---|---|---|
| H | H | 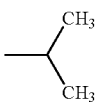 | H |
| H | H | —(CH$_2$)$_2$— | —OR$^8$<br>R$^8$ = —CH$_3$ |
| H | H | —(CH$_2$)$_3$— | —OR$^8$<br>R$^8$ = —CH$_3$ |
| H | H | —(CH$_2$)$_2$— | —OR$^8$<br>R$^8$ = —(CH$_2$)$_2$—OH |
| H | H | —(CH$_2$)$_2$— | —C(O)OR$^9$<br>R$^9$ = —CH$_3$ |
| H | H | —CH$_2$— | —C(O)OR$^9$<br>R$^9$ = —CH$_2$CH$_3$ |
| H | H | —(CH$_2$)$_3$— | —N(R$^{10}$)R$^{11}$<br>R$^{10}$ = —CH$_2$CH$_3$<br>R$^{11}$ = —CH$_2$CH$_3$ |
| —CH$_3$ | H | —CH$_2$— | 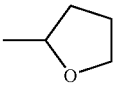 |
| —CH$_3$ | H | —CH$_2$— | 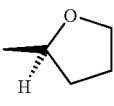 |
| —OCH$_3$ | H | —CH$_2$— | 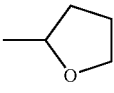 |
| —CH$_3$ | H | —CH$_2$— | 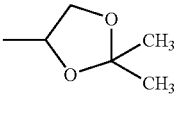 |
| —CH$_3$ | H | —CH$_2$— | 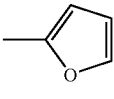 |
| —CH$_3$ | H | —CH$_2$— | H |
| —CH$_3$ | H | —(CH$_2$)$_3$— | H |
| —CH$_3$ | H | 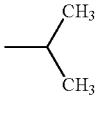 | H |
| —CH$_3$ | H | —(CH$_2$)$_2$— | —OR$^8$<br>R$^8$ = —CH$_3$ |
| —CH$_3$ | H | —(CH$_2$)$_3$— | —OR$^8$<br>R$^8$ = —CH$_3$ |
| —CH$_3$ | H | —(CH$_2$)$_2$— | —OR$^8$<br>R$^8$ = —(CH$_2$)$_2$—OH |
| —CF$_3$ | H | —(CH$_2$)$_2$— | —OR$^8$<br>R$^8$ = —CH$_3$ |
| —OCH$_3$ | H | —(CH$_2$)$_2$— | —OR$^8$<br>R$^8$ = —CH$_3$ |
| —OCH$_3$ | H | —(CH$_2$)$_3$— | —OR$^8$<br>R$^8$ = —CH$_3$ |

-continued
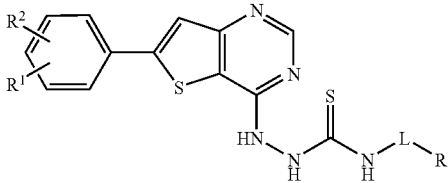
| R¹ | R² | L | R³ |
|---|---|---|---|
| —OCH₃ | H | —(CH₂)₂— | —OR⁸<br>R⁸ = —(CH₂)₂—OH |
| —Cl | H | —(CH₂)₂— | —OR⁸<br>R⁸ = —CH₃ |
| 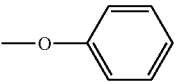 | H | —(CH₂)₂— | —OR⁸<br>R⁸ = —CH₃ |
| 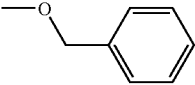 | H | —(CH₂)₂— | —OR⁸<br>R⁸ = —CH₃ |
| —CH₃ | —CH₃ | —CH₂— | 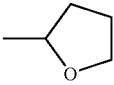 |
| —CH₃ | —CH₃ |  | H |
| —CH₃ | —CH₃ | —(CH₂)₂— | —OR⁸<br>R⁸ = —CH₃ |
| —CH₃ | —CH₃ | —(CH₂)₃— | —OR⁸<br>R⁸ = —CH₃ |
|  | | —(CH₂)₂— | —OR⁸<br>R⁸ = —CH₃ |
| 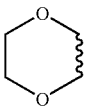 | | —(CH₂)₂— | —OR⁸<br>R⁸ = —CH₃ |
| H | H | —CH(R⁵)—<br>R⁵ = —CH₃ | 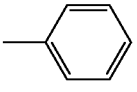 |
| H | H | —CH₂CH(R⁵)—<br>R⁵ = 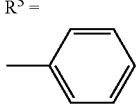 | 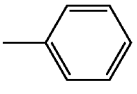 |
| H | H | —CH(R⁵)—<br>R⁵ = R⁶—O—R⁷<br>R⁶ = —CH₂—<br>R⁷ = —CH₃ | 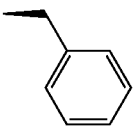 |

-continued

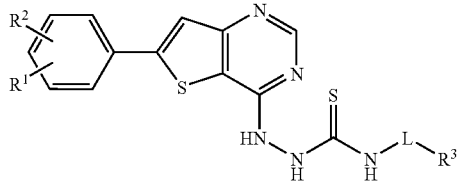

| R¹ | R² | L | R³ |
|---|---|---|---|
| H | H | —CH(R⁵)—<br>R⁵ = R⁶—S—R⁷<br>R⁶ = —(CH₂)₂—<br>R⁷ = —CH₃ | —OR⁸<br>R⁸ = —CH₃ |
| H | H | —CH(R⁵)—<br>R⁵ = 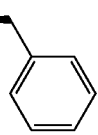 | —C(O)OR⁹<br>R⁹ = —CH₃ |
| H | H | —CH(R⁵)—<br>—R⁶—C(O)OR⁷<br>R⁶ = —CH₂—<br>R⁷ = —CH₃ | —C(O)OR⁹<br>R⁹ = —CH₃ |
| H | H | —C(O)— | 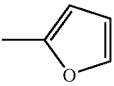 |

In a preferred embodiment the inhibitors of tubulin polymerization of the invention do not include compounds wherein when R¹ and R² are both —H, -L-R³ is one of the following:

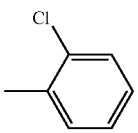 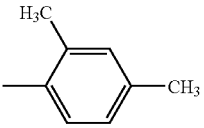

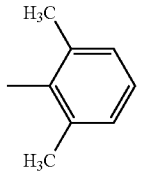 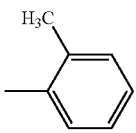

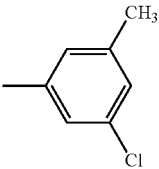 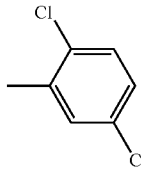

-continued

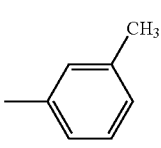 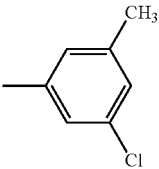

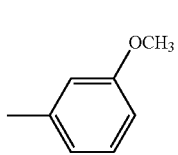 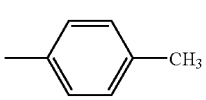

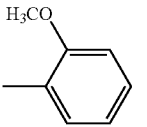 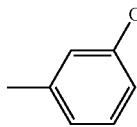

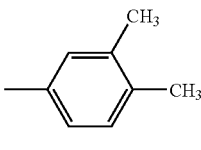

In a most preferred embodiment of the compounds of paragraph [0047], the inhibitors of tubulin polymerization of the invention comprise the following compounds:

| No. | Compound |
|---|---|
| 1 | 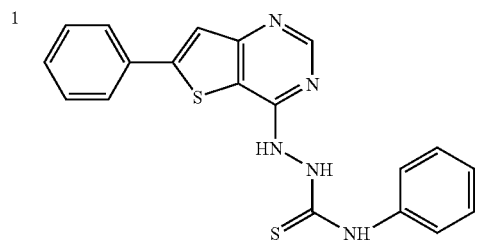 |
| 2 | 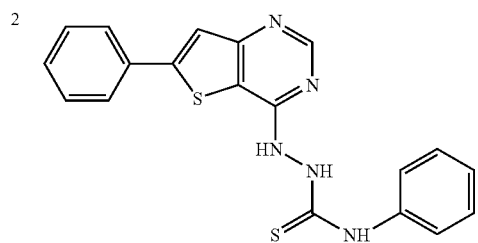 |
| 3 | 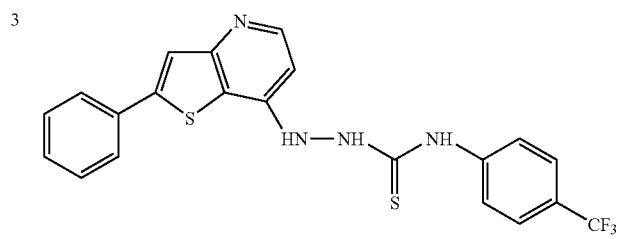 |
| 4 | 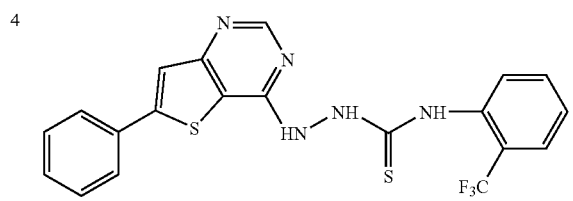 |
| 5 | 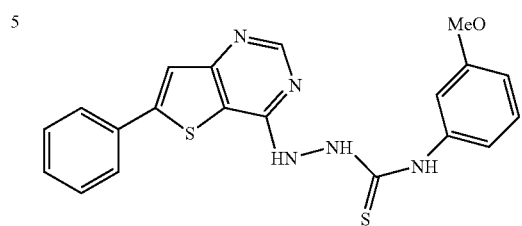 |
| 6 | 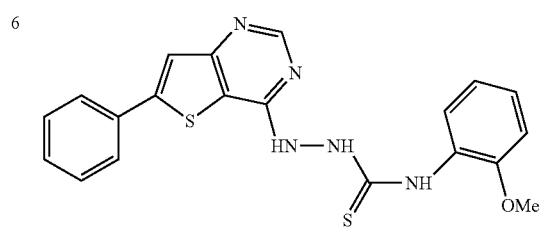 |

-continued
| No. | Compound |
|---|---|
| 7 | 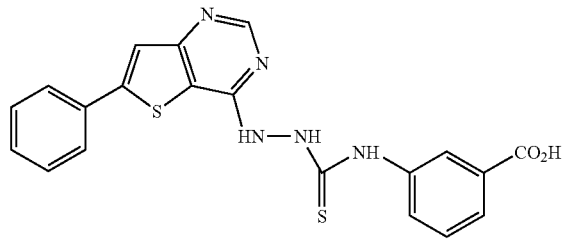 |
| 8 | 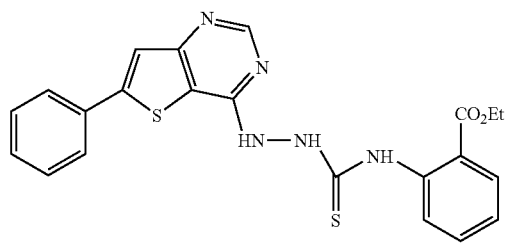 |
| 9 | 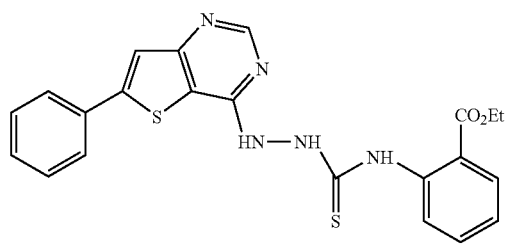 |
| 10 | 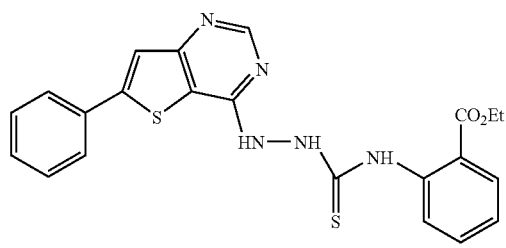 |
| 11 | 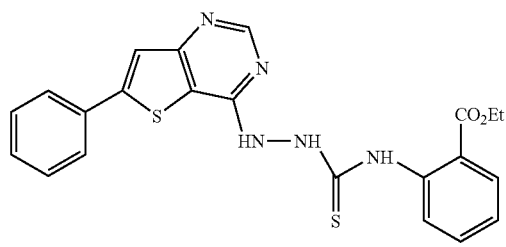 |
| 12 | 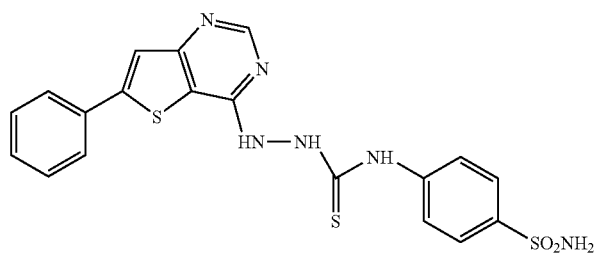 |

-continued

| No. | Compound |
|---|---|
| 13 | 6-phenyl-thieno[3,2-d]pyrimidin-4-yl-HN–NH–C(=S)–NH–(2,4-dimethoxyphenyl) |
| 14 | 6-phenyl-thieno[3,2-d]pyrimidin-4-yl-HN–NH–C(=S)–NH–(2,4-dimethoxyphenyl) |
| 15 | 6-phenyl-thieno[3,2-d]pyrimidin-4-yl-HN–NH–C(=S)–NH–(3,4-dimethoxyphenyl) |
| 16 | 6-phenyl-thieno[3,2-d]pyrimidin-4-yl-HN–NH–C(=S)–NH–(2,5-dimethoxyphenyl) |
| 17 | 6-phenyl-thieno[3,2-d]pyrimidin-4-yl-HN–NH–C(=S)–NH–(2-methoxy-4-nitrophenyl) |
| 18 | 6-phenyl-thieno[3,2-d]pyrimidin-4-yl-HN–NH–C(=S)–NH–(2-methoxy-4-nitrophenyl) |

-continued

| No. | Compound |
|---|---|
| 19 | *6-phenylthieno[3,2-d]pyrimidin-4-yl hydrazine N-cyclopropyl thiosemicarbazide* |
| 20 | *6-phenylthieno[3,2-d]pyrimidin-4-yl hydrazine N-cyclopentyl thiosemicarbazide* |
| 21 | *6-phenylthieno[3,2-d]pyrimidin-4-yl hydrazine N-(2-benzyloxycyclopentyl) thiosemicarbazide* |
| 22 | *6-phenylthieno[3,2-d]pyrimidin-4-yl hydrazine N-(2-benzyloxycyclopentyl) thiosemicarbazide* |
| 23 | *6-phenylthieno[3,2-d]pyrimidin-4-yl hydrazine N-(2-benzyloxycyclopentyl) thiosemicarbazide* |
| 24 | *6-phenylthieno[3,2-d]pyrimidin-4-yl hydrazine N-(2-methoxycarbonylthien-3-yl) thiosemicarbazide* |
| 25 | *6-phenylthieno[3,2-d]pyrimidin-4-yl hydrazine N-(pyridin-3-yl) thiosemicarbazide* |

-continued
| No. | Compound |
|---|---|
| 26 | 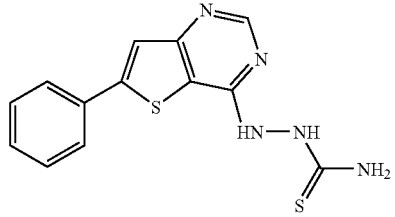 |
| 27 | 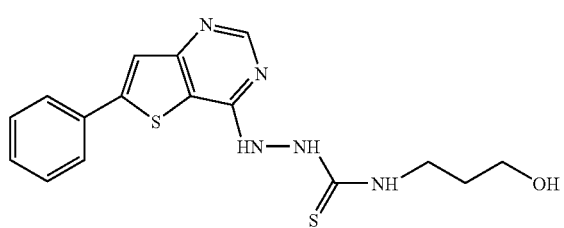 |
| 28 | 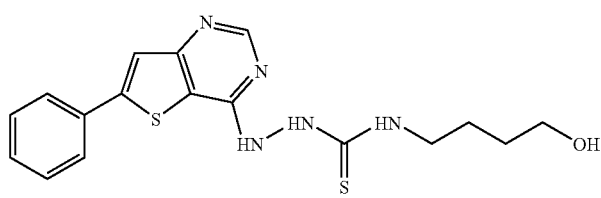 |
| 29 | 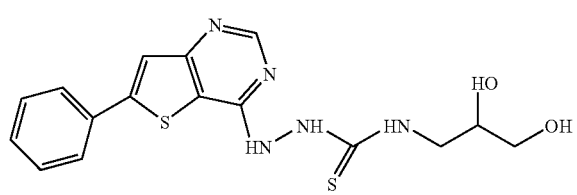 |
| 30 | 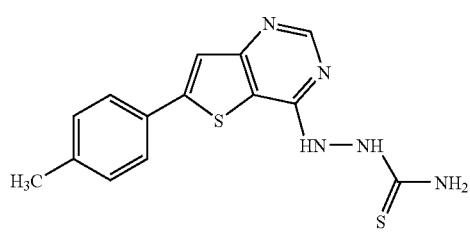 |
| 31 | 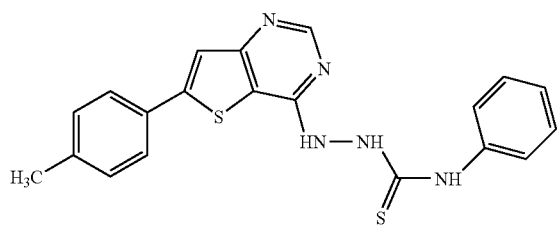 |
| 32 | 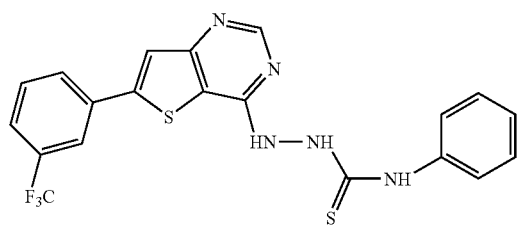 |

-continued
| No. | Compound |
|---|---|
| 33 | 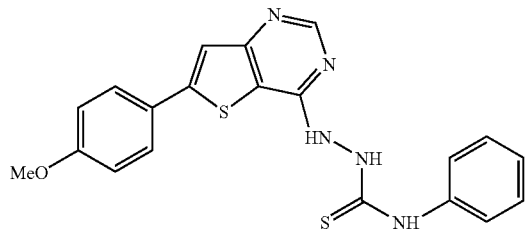 |
| 34 | 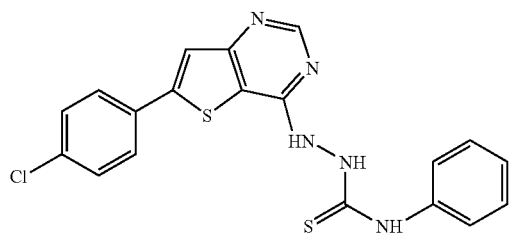 |
| 35 | 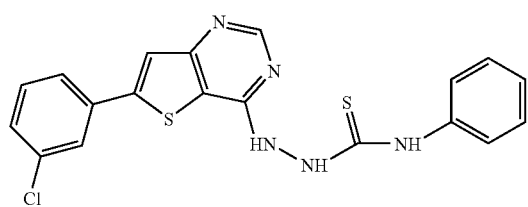 |
| 36 | 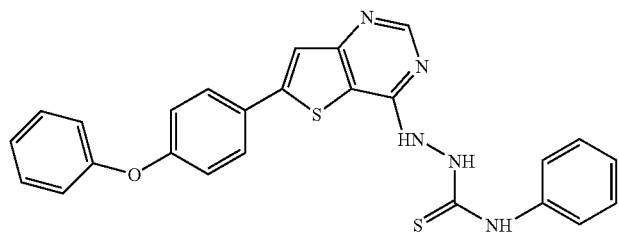 |
| 37 | 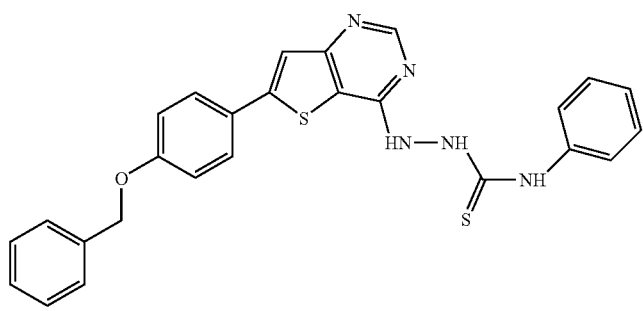 |
| 38 | 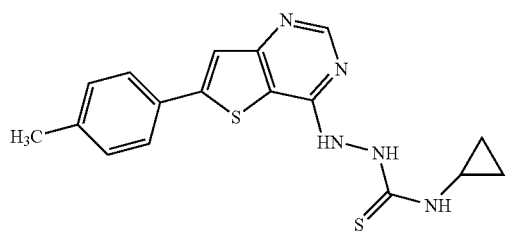 |

-continued
| No. | Compound |
|---|---|
| 39 | 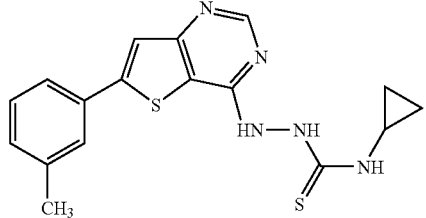 |
| 40 | 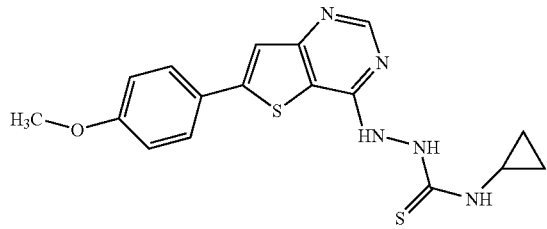 |
| 41 | 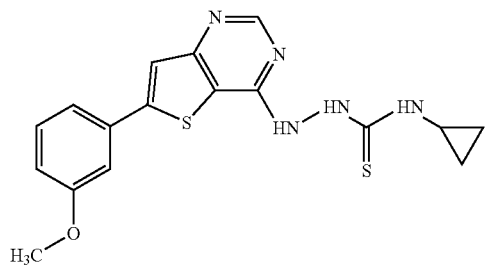 |
| 42 | 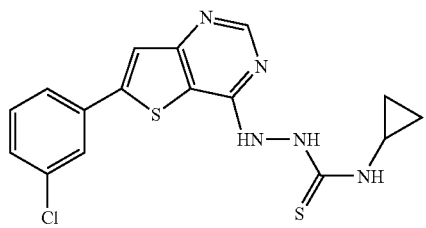 |
| 43 | 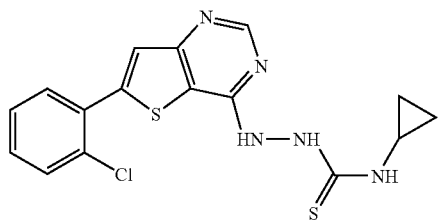 |
| 44 | 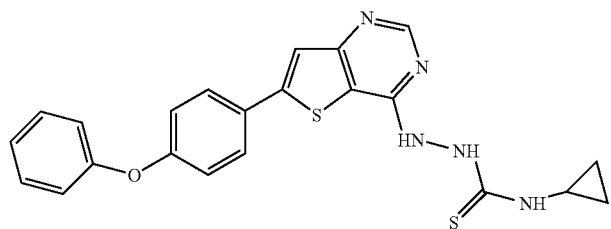 |

-continued

| No. | Compound |
|---|---|
| 45 | |
| 46 | |
| 47 | |
| 48 | |
| 49 | |
| 50 | |

-continued
| No. | Compound |
|-----|----------|
| 51 | 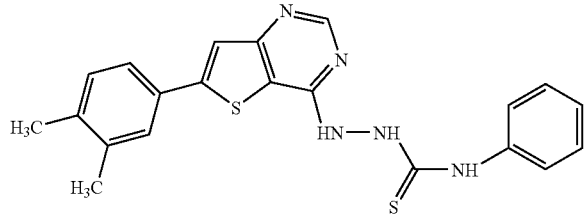 |
| 52 | 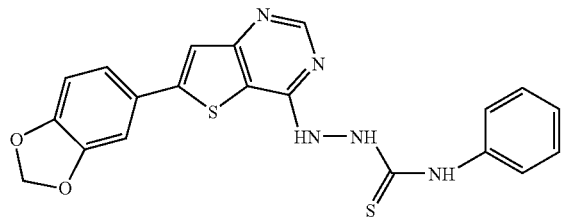 |
| 53 | 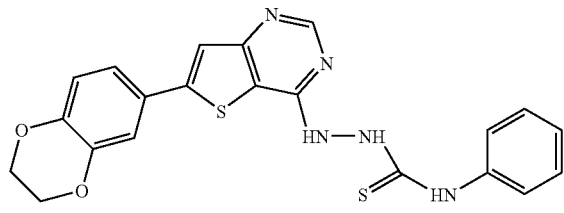 |
| 54 | 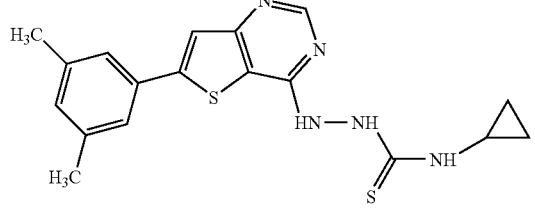 |
| 55 | 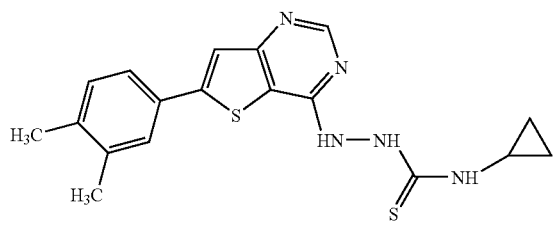 |
| 56 | 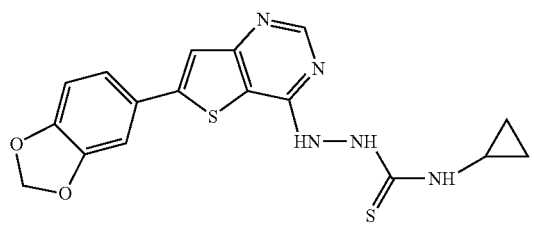 |
| 57 | 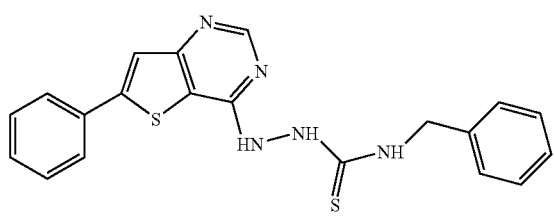 |

| No. | Compound |
|---|---|
| 58 | 6-phenyl-thieno[3,2-d]pyrimidin-4-yl-NH-NH-C(=S)-NH-CH₂CH₂-phenyl |
| 59 | 6-phenyl-thieno[3,2-d]pyrimidin-4-yl-NH-NH-C(=S)-NH-CH₂CH₂CH₂-phenyl |
| 60 | 6-phenyl-thieno[3,2-d]pyrimidin-4-yl-NH-NH-C(=S)-NH-CH₂-(4-MeO-phenyl) |
| 61 | 6-phenyl-thieno[3,2-d]pyrimidin-4-yl-NH-NH-C(=S)-NH-CH₂-(4-Cl-phenyl) |
| 62 | 6-phenyl-thieno[3,2-d]pyrimidin-4-yl-NH-NH-C(=S)-NH-CH₂-cyclopropyl |
| 63 | 6-phenyl-thieno[3,2-d]pyrimidin-4-yl-NH-NH-C(=S)-NH-CH₂-(tetrahydrofuran-2-yl) |
| 64 | 6-phenyl-thieno[3,2-d]pyrimidin-4-yl-NH-NH-C(=S)-NH-CH₂-((2S)-tetrahydrofuran-2-yl) |

-continued
| No. | Compound |
|---|---|
| 65 | 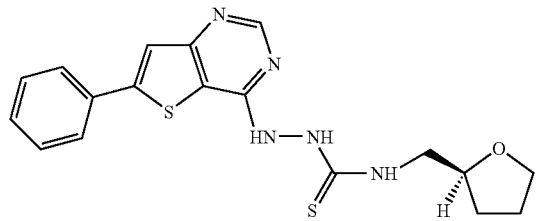 |
| 66 | 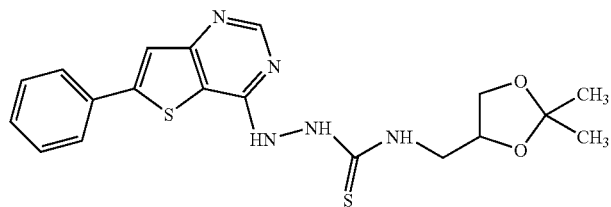 |
| 67 | 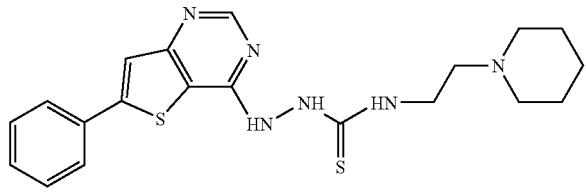 |
| 68 | 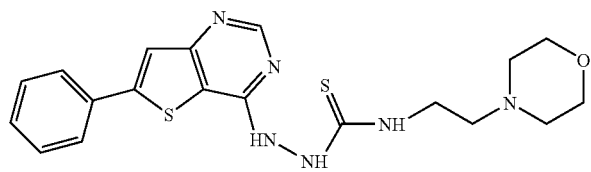 |
| 69 | 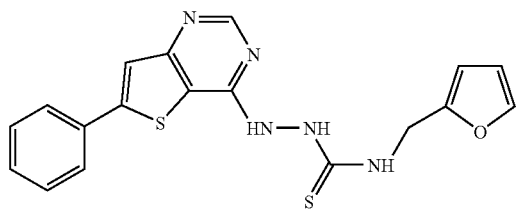 |
| 70 | 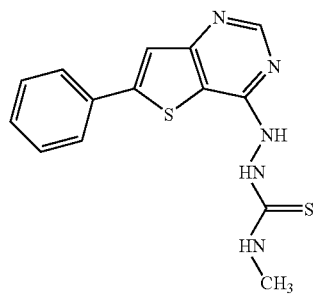 |
| 71 | 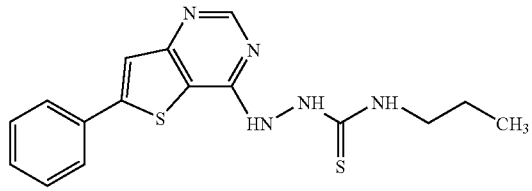 |

-continued
| No. | Compound |
|---|---|
| 72 | 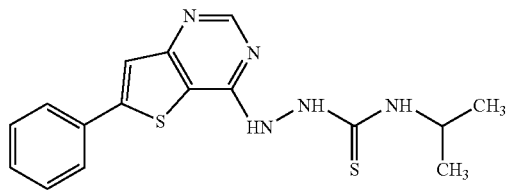 |
| 73 | 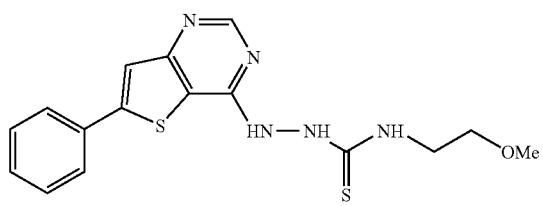 |
| 74 | 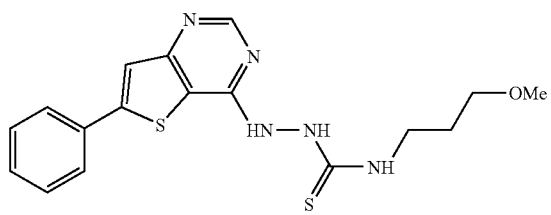 |
| 75 | 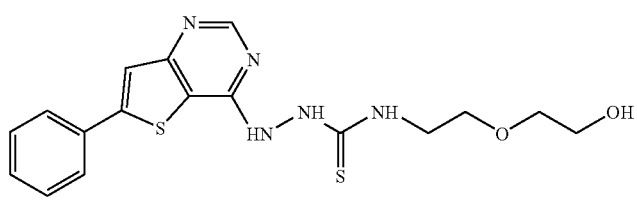 |
| 76 | 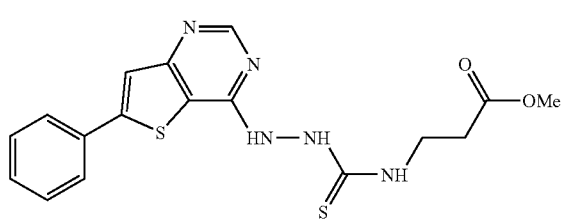 |
| 77 | 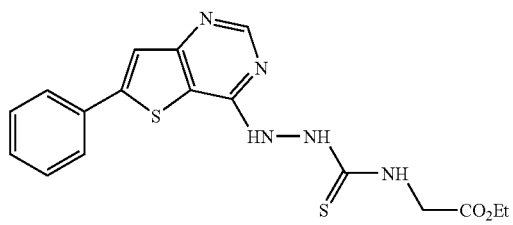 |
| 78 | 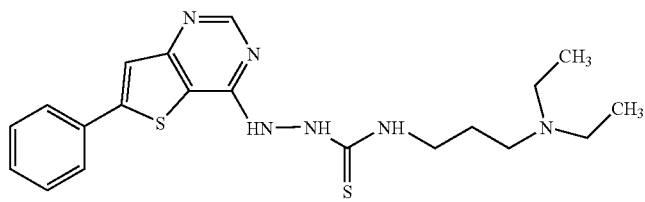 |

| No. | Compound |
|---|---|
| 79 | 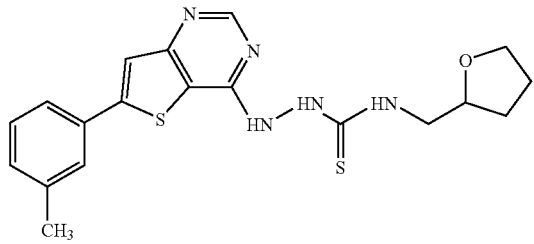 |
| 80 | 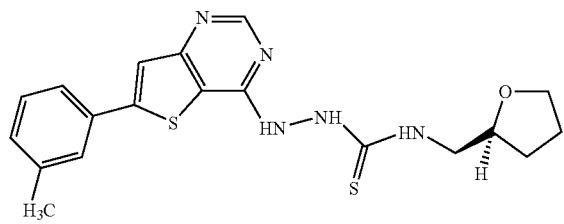 |
| 81 | 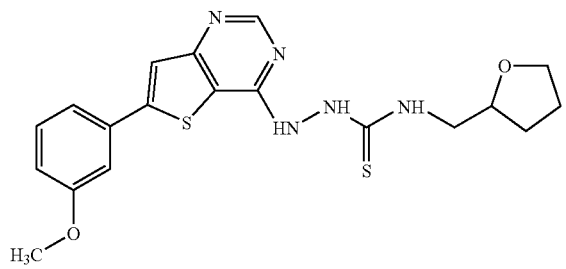 |
| 82 | 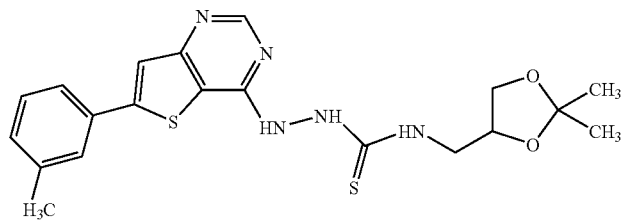 |
| 83 | 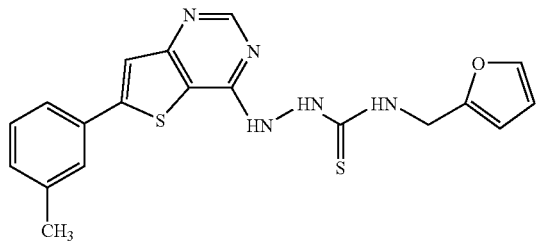 |
| 84 | 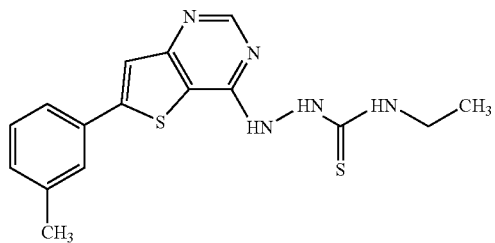 |

-continued
| No. | Compound |
|-----|----------|
| 85  | 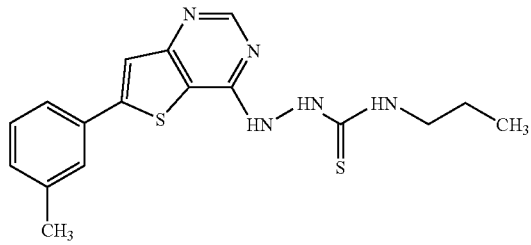 |
| 86  | 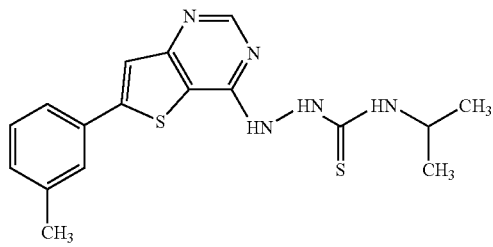 |
| 87  | 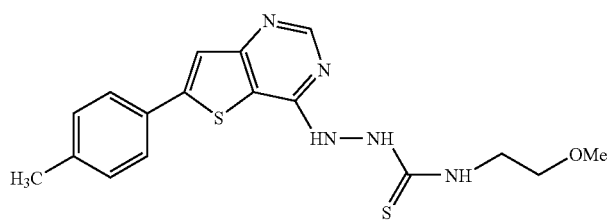 |
| 88  | 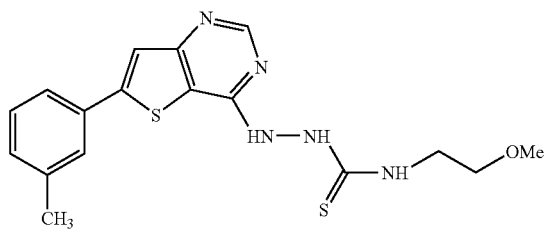 |
| 89  | 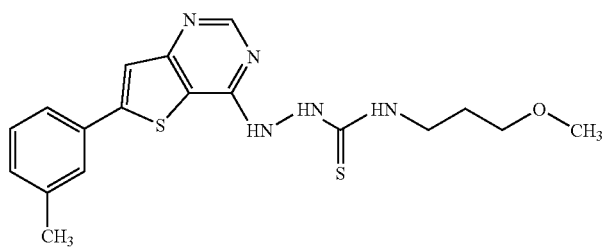 |
| 90  | 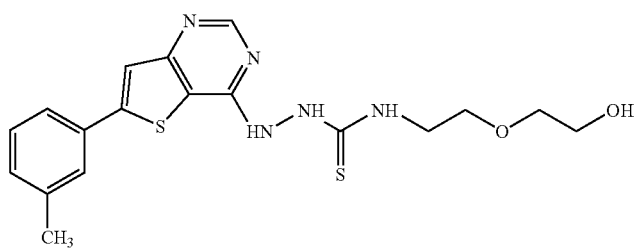 |

-continued

| No. | Compound |
|---|---|
| 91 | |
| 92 | |
| 93 | |
| 94 | |
| 95 | |
| 96 | |

| No. | Compound |
|---|---|
| 97 | 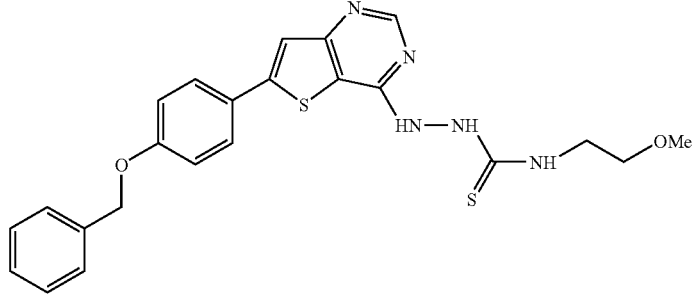 |
| 98 | 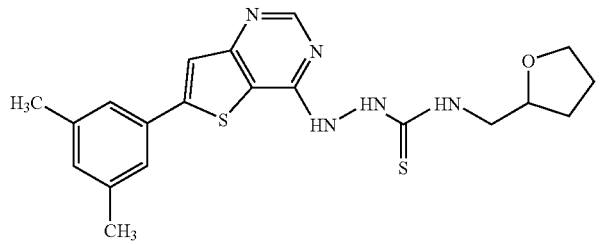 |
| 99 | 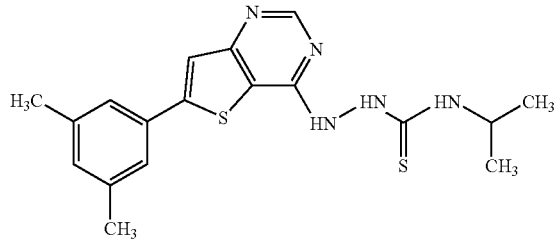 |
| 100 | 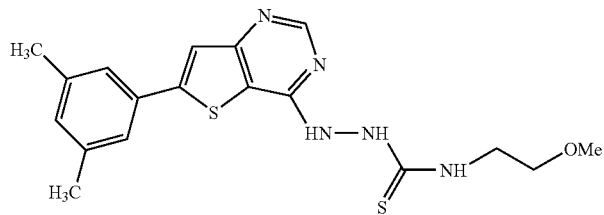 |
| 101 | 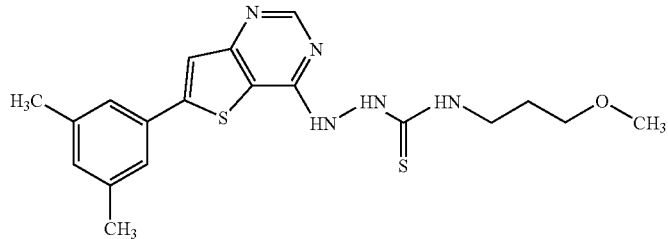 |
| 102 | 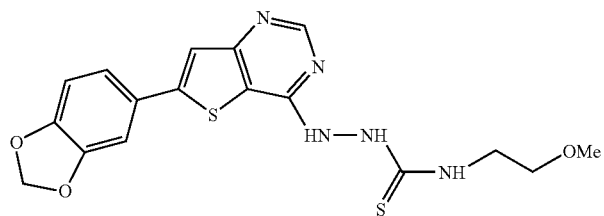 |

-continued
| No. | Compound |
|---|---|
| 103 | 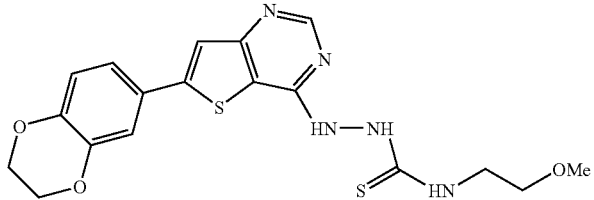 |
| 104 | 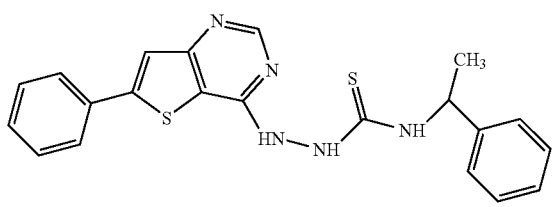 |
| 105 | 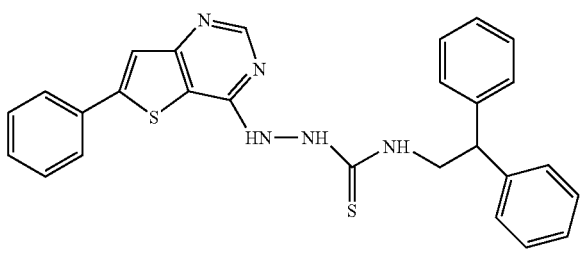 |
| 106 | 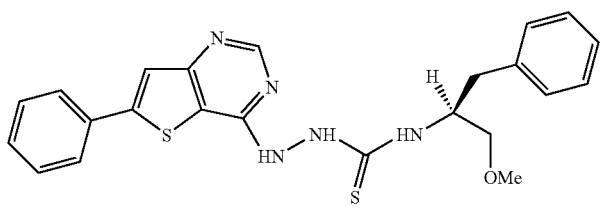 |
| 107 | 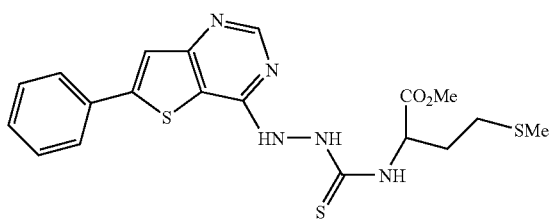 |
| 108 | 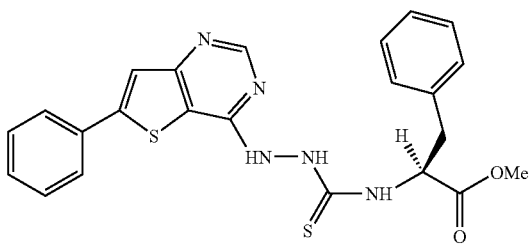 |

-continued

| No. | Compound |
|-----|----------|
| 109 | 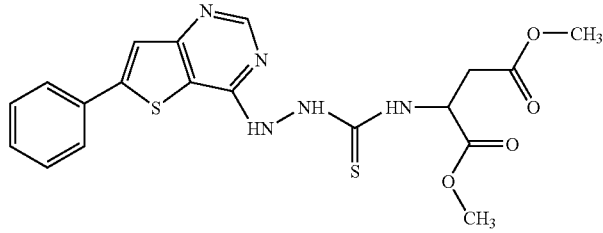 |
| 110 | 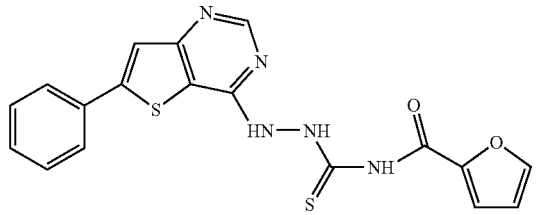 |

Synthesis

The compounds of general formula (1) may be synthesized as outlined in Scheme 1 utilizing methods known to one of skill in the art. The origin of $R^3$ is isothiocyanates, which are readily prepared from amines, as would be known to one of skill in the art, or are commercially available.

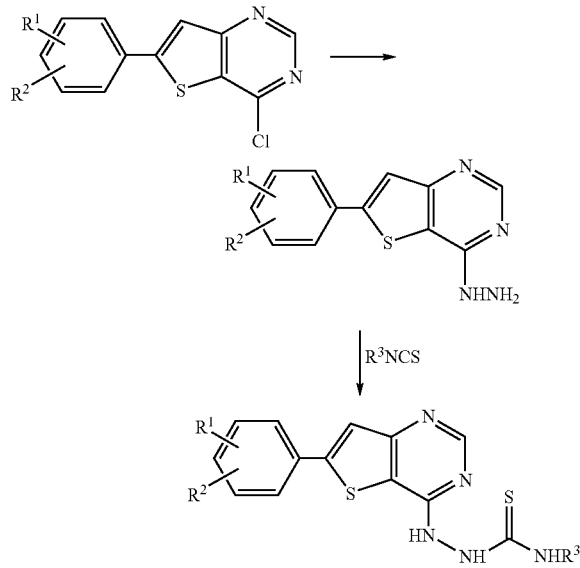

Scheme 1

Pharmaceutical Compositions

In a second aspect, the invention provides pharmaceutical compositions comprising an inhibitor of tubulin polymerization according to the invention and a pharmaceutically acceptable carrier, excipient, or diluent. Compounds of the invention may be formulated by any method well known in the art and may be prepared for administration by any route, including, without limitation, parenteral, oral, sublingual, transdermal, topical, intranasal, intratracheal, or intrarectal. In certain preferred embodiments, compounds of the invention are administered intravenously in a hospital setting. In certain other preferred embodiments, administration may preferably be by the oral route.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

As used herein, the term pharmaceutically acceptable salts refers to salts that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. The compounds can also be administered as pharmaceutically acceptable quaternary salts known by those skilled in the art, which specifically include the quaternary ammonium salt of the formula —NR+Z-, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The active compound is included in the pharmaceutically acceptable carrier or diluent in an amount sufficient to deliver to a patient a therapeutically effective amount without causing serious toxic effects in the patient treated. A preferred dose of the active compound for all of the above-mentioned conditions is in the range from about 0.01 to 300 mg/kg, preferably 0.1 to 100 mg/kg per day, more generally 0.5 to about 25 mg per kilogram body weight of the recipient per day. A typical topical dosage will range from 0.01–3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

Inhibition of Tubulin Polymerization

In a third aspect, the invention provides a method of inhibiting tubulin polymerization in a cell, comprising contacting a cell in which inhibition of tubulin polymerization is desired with an inhibitor of tubulin polymerization of the invention.

Measurement of the tubulin polymerization can be achieved using known methodologies. For example, assays for tubulin polymerization may be performed using a kit from Cytoskeleton (Denver, Colo.) and as described by Tahir, S. K., et al, (2001) Cancer Res., 61:5480–5.

Preferably, the method according to the third aspect of the invention causes an inhibition of cell proliferation of contacted cells. The phrase "inhibiting cell proliferation" is used to denote an ability of an inhibitor of tubulin polymerization to retard the growth of cells contacted with the inhibitor as compared to cells not contacted. An assessment of cell proliferation can be made by counting contacted and non-contacted cells using a Coulter Cell Counter (Coulter, Miami, Fla.) or a hemacytometer. Where the cells are in a solid growth (e.g., a solid tumor or organ), such an assessment of cell proliferation can be made by measuring the growth with calipers and comparing the size of the growth of contacted cells with non-contacted cells.

Preferably, growth of cells contacted with the inhibitor is retarded by at least 50% as compared to growth of non-contacted cells. More preferably, cell proliferation is inhibited by 100% (i.e., the contacted cells do not increase in number). Most preferably, the phrase "inhibiting cell proliferation" includes a reduction in the number or size of contacted cells, as compared to non-contacted cells. Thus, an inhibitor of tubulin polymerization according to the invention that inhibits cell proliferation in a contacted cell may induce the contacted cell to undergo growth retardation, to undergo growth arrest, to undergo programmed cell death (i.e., to apoptose), or to undergo necrotic cell death.

In some preferred embodiments, the contacted cell is a neoplastic cell. The term "neoplastic cell" is used to denote a cell that shows aberrant cell growth. Preferably, the aberrant cell growth of a neoplastic cell is increased cell growth. A neoplastic cell may be a hyperplastic cell, a cell that shows a lack of contact inhibition of growth in vitro, a benign tumor cell that is incapable of metastasis in vivo, or a cancer cell that is capable of metastasis in vivo and that may recur after attempted removal. The term "tumorigenesis" is used to denote the induction of cell proliferation that leads to the development of a neoplastic growth. In some embodiments, the tubulin polymerization inhibitor induces cell differentiation in the contacted cell. Thus, a neoplastic cell, when contacted with an inhibitor of tubulin polymerization may be induced to differentiate, resulting in the production of a non-neoplastic daughter cell that is phylogenetically more advanced than the contacted cell.

Treatment for Cell Proliferative Diseases or Conditions

In some preferred embodiments, the contacted cell is in an animal. Thus, in a fourth aspect the invention provides a method for treating a cell proliferative disease or condition in an animal, comprising administering to an animal in need thereof an effective amount of an inhibitor of tubulin polymerization of the invention. Preferably, the animal is a mammal, more preferably a domesticated mammal. Most preferably, the animal is a human.

The term "cell proliferative disease or condition" is meant to refer to any condition characterized by aberrant cell growth, preferably abnormally increased cellular proliferation. Examples of such cell proliferative diseases or conditions include, but are not limited to, cancer, restenosis, and psoriasis. In particularly preferred embodiments, the invention provides a method for inhibiting neoplastic cell proliferation in an animal comprising administering to an animal having at least one neoplastic cell present in its body a therapeutically effective amount of a tubulin polymerization inhibitor of the invention. Most preferably, the invention provides a method for treating cancer comprising administering to a patient in need thereof an effective amount of an inhibitor of tubulin polymerization of the invention.

The term "therapeutically effective amount" is meant to denote a dosage sufficient to cause inhibition of tubulin polymerization in the cells of the subject, or a dosage sufficient to inhibit cell proliferation or to induce cell differentiation in the subject. Administration may be by any route, including, without limitation, parenteral, oral, sublingual, transdermal, topical, intranasal, intratracheal, or intrarectal. In certain particularly preferred embodiments, compounds of the invention are administered intravenously in a hospital setting. In certain other preferred embodiments, administration may preferably be by the oral route.

When administered systemically, the tubulin polymerization inhibitor is preferably administered at a sufficient dosage to attain a blood level of the inhibitor from about 0.01 µM to about 100 µM, more preferably from about 0.05 µM to about 50 µM, still more preferably from about 0.1 µM to about 25 µM, and still yet more preferably from about 0.5 µM to about 25 µM. For localized administration, much lower concentrations than this may be effective, and much higher concentrations may be tolerated. One of skill in the art will appreciate that the dosage of tubulin polymerization inhibitor necessary to produce a therapeutic effect may vary considerably depending on the tissue, organ, or the particular animal or patient to be treated.

The following examples are intended to further illustrate certain preferred embodiments of the invention, and are not intended to limit the scope of the invention.

EXAMPLES

Example 1

Inhibition of Tubulin Polymerization

Figure 1B:
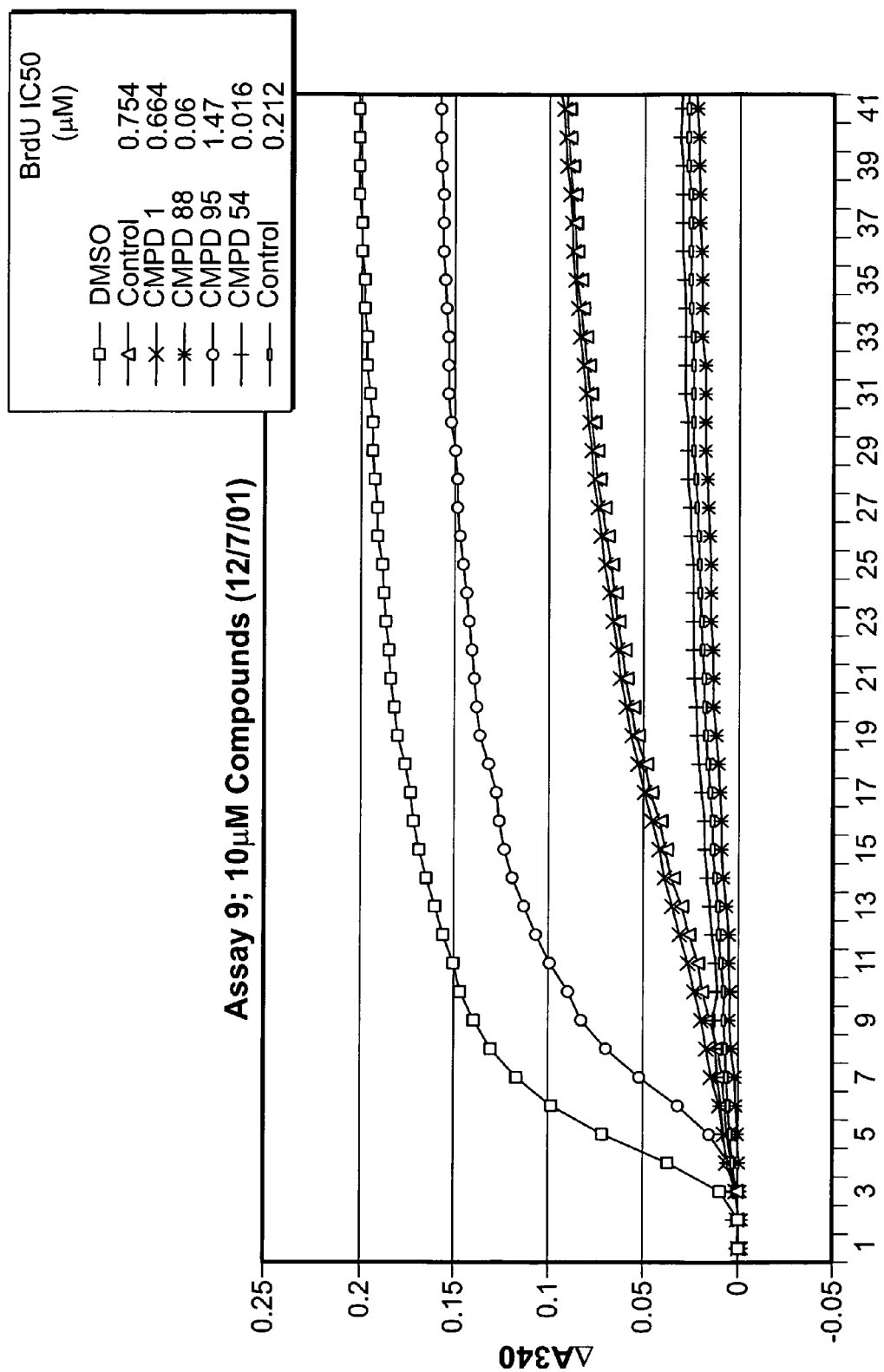
Figure 1C:
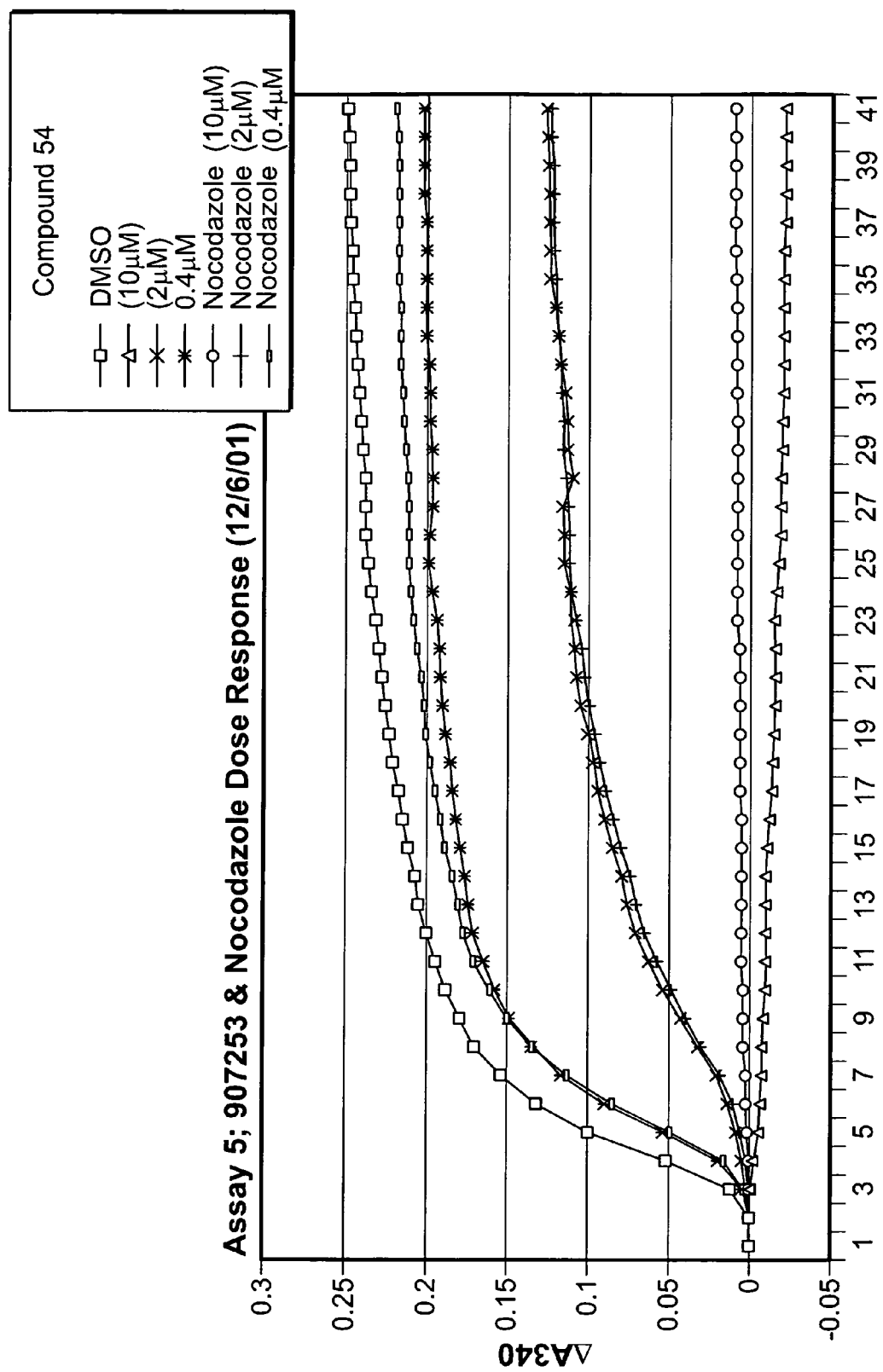

FIG. 1 illustrates the inhibition of tubulin polymerization activity conferred by exemplary compounds of the invention.

The assay measures tubulin polymerization as an increase in turbidity ($A_{340}$) over time. Assays for tubulin polymerization were performed using a kit from Cytoskeleton (Denver, Colo.) and as described by Tahir, S. K., et al, (2001) Cancer Res., 61: 5480–5, incorporated herein by reference, and as described below.

To determine the ability of the compounds to inhibit microtubule polymerization in vitro, the following protocol was followed: (i) 70 µl ice-cold MAP-rich tubulin protein from bovine brain (1.5 mg/ml final concentration) was added to polymerization buffer (80 mM PIPES pH6.8, 1 mM EGTA, 1 mM $MgCl_2$, 1 mM GTP) in a quartz microcuvette; (ii) 0.7 µl of DMSO or 100X stock of control (nocodazole) or test compound (thienopyrimidine) in DMSO were added to the cuvette; (iii) the contents were mixed by pipetting gently; (iv) the polymerization reaction was initiated by placing the cuvette in pre-warmed (37° C.) cuvette holder in Beckman spectrophotometer; (v) the absorbance was monitored at 340 nm at 30 second intervals for 20 minutes. Tubulin polymerization result in increased turbidity in the reaction solution, which is registered as an increase in absorbance at 340 nm. Inhibitors of tubulin polymerization are detected by a reduction in the rate, the initial slope, and/or extent of the turbidity change (i.e., max. absorbance at 340 nm) in plots of $\Delta A_{340}$ versus time.

Example 2

Antitumor Activity of Compound 1 Against Human Lung and Colon Tumors in Nude Mouse Xenografts A nude mouse/human carcinoma model was used to examine the effect of tubulin inhibitors on tumor growth and animal survival. Groups of immune deficient (nude) mice were implanted subcutaneously with suspensions of the human tumor lines A549 (lung) and SW480 (colon). When palpable tumors appeared and were of a preselected volume (approximately 40–150 $mm^3$), animals were subdivided into various treatment groups such that the variation in mean tumor volume of each group was within 10%. The animals were then treated daily with either control vehicle or Compound 1 administered by intraperitonel injection. Twice weekly, the volume of the tumors in each animal in each group was measured to gather information on tumor growth (volume) as a function of time. Systemic toxicity was assessed by measuring individual animal body weights, and toxicity was evaluated by examination of differences in body weight gain as a function of time. Tumor volumes and body weights were monitored for up to 35 days after the beginning of treatment.

Experimental Procedures

Cell Lines: Human tumor lines A549 (lung) and SW480 (colon) were grown in cell culture medium (F-11) containing 10% Fetal Bovine Serum (FBS). The cells were kept at 37° C. in a humidified 5% CO2/air incubator. Antibiotics were not added to the medium.

Animal Tumor Model

NCr nude (nu/nu) female mice, age 3–4 weeks, were purchased from Taconic (Germantown, N.Y.). The animals were housed ten per cage in sterile filter-topped cages in ventilated cage racks and Microisolator™ cages. Upon arrival, they were quarantined for at least four working days before use. Temperature was maintained at 72±5° F. (19–24° C.) and relative humidity at 35–70%, and a 12-hour light/dark cycle was used. The mice were fed sterile, autoclavable, certified, Purina rodent chow ad libitum. Drinking water was also autoclaved.

After the animals were released from quarantine, the mice were injected subcutaneously in the right flank with either $5 \times 10^6$ A549 cells or $5 \times 10^6$ SW480 cells in complete medium at an injection volume of 0.1 ml. Tumor dimensions and body weights were measured two times per week. Vernier calipers were used to measure tumors in two planes, and tumor volume (V) was calculated as follows:

$$V=(xy^2)/2,$$

where x and y were the tumor measurements minus skin thickness. At the end of the experiment, the mice were sacrificed by $CO_2$ inhalation followed by cervical dislocation.

Pharmaceuticals

The test articles were administered intraperitoneally generally at a dose level of 10 mg/kg. When the solubility of a molecule of the invention was relatively low, we used relatively higher levels of organic co-solvents for preparation of the dosing solution. The "vehicle" of the invention comprised of 7.1% ethanol/35.8% PEG400/57.1% phosphate buffer (v/v/v).

Treatment Protocol

When the tumor volumes reached a predetermined size (mean tumor volume between about 40–150 $mm^3$), animals were added randomly to treatment groups of 12 mice each as follows: Animals were treated daily with the vehicle or Compound 1 (10 mg/kg), or with the positive control drug (Taxol) administered by intraperitoneal injection at the maximum tolerated dose of 20 mg/kg every fourth day, on Days 1, 4, 7, and 10.

The tumor volumes of the animals were monitored for evidence of shrinkage or growth delay for a period of up to 35 days after the start of treatment. Response to treatment was measured in two ways, depending on the tumor response to treatment. The first was the optimum T/C (%), calculated as follows: For each day the tumors were measured, the changes in median tumor volume (V) for each treated (T) and control (C) group were determined by subtracting the mean tumor volume on the first day of treatment (Day 0) from the median tumor volume on the specific observation day. These values were used to express a percent difference in size, [% T/C=(T/C)×100]. The minimum value is designated the optimum response to treatment. A value of 42% or less is considered active by National Cancer Institute (NCI) standards.

At the end of the study the mice were sacrificed by $CO_2$ inhalation followed by cervical dislocation. Animals were sacrificed if their tumor volumes reached 2500 $mm^3$.

Statistical analyses as described above was performed using JMP (SAS Institute Inc., Cary, N.C.).

Results: Animal Tumor Model

Tumor Growth

The tumors in mice were measurable within 14 days of tumor cell injection and grew with an initial mean doubling time of about 4 days. These values were calculated from the control group. Endpoint results are presented as Day 35 of the study, since the first control animals were sacrificed at that time.

Tumor Response to Treatment

Figure 2:
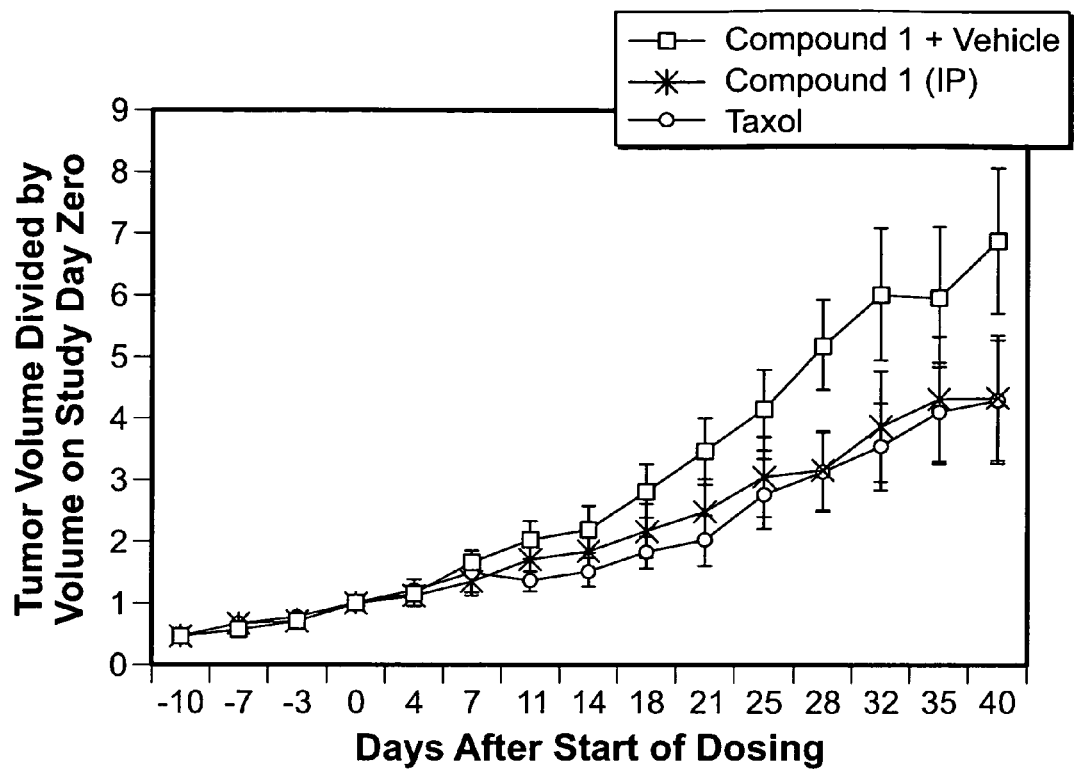
FIG. 2. A549 (lung) tumor cell line response to (i) Compound 1 (IP) versus (ii) Compound 1 plus vehicle and (iii) Taxol. Compound 1 confers substantial suppression of tumor growth.
Figure 3:
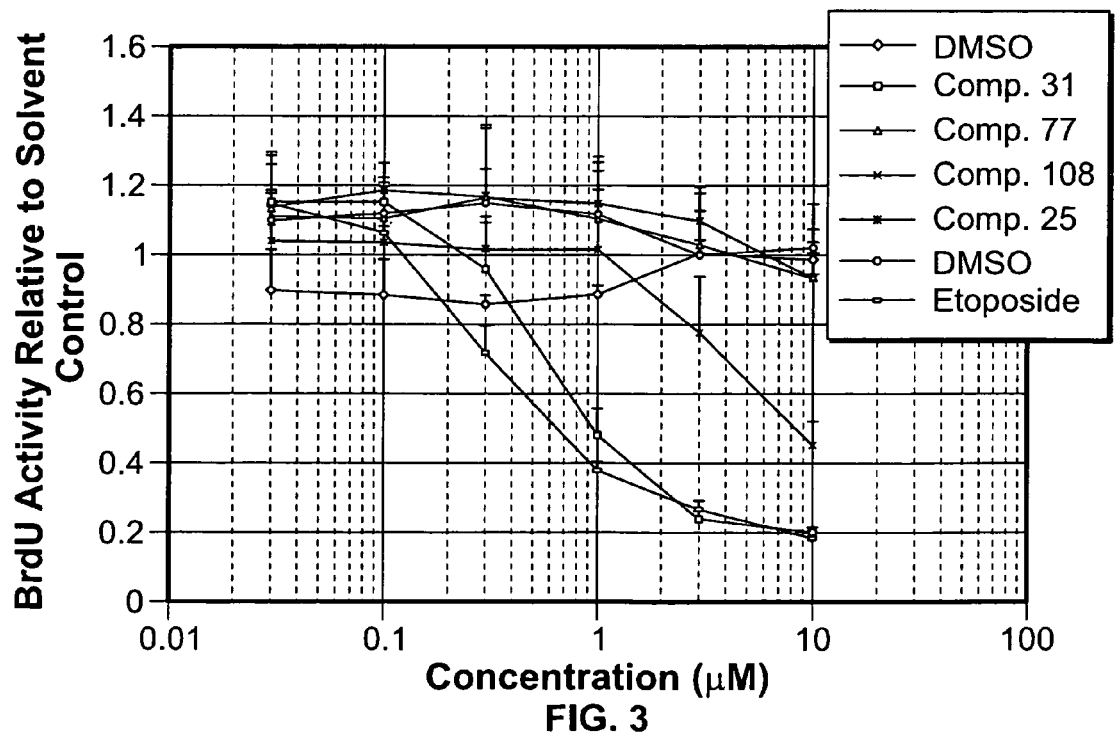
FIG. 3. Antiproliferation activity of various compounds of the invention utilizing bromodeoxyuridine (BrdU) proliferation assay with a breast cancer cell line.
Figure 4:
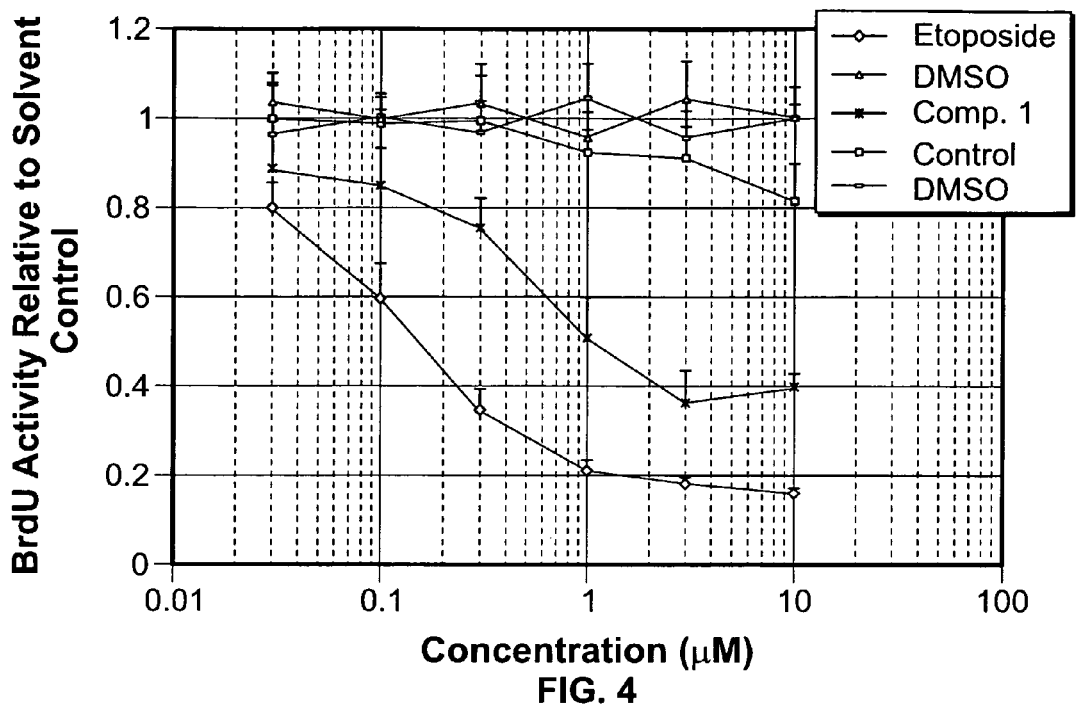
FIG. 4. Antiproliferation activity of compound 1 of the invention utilizing bromodeoxyuridine (BrdU) proliferation assay with a breast cancer cell line.
Figure 5:
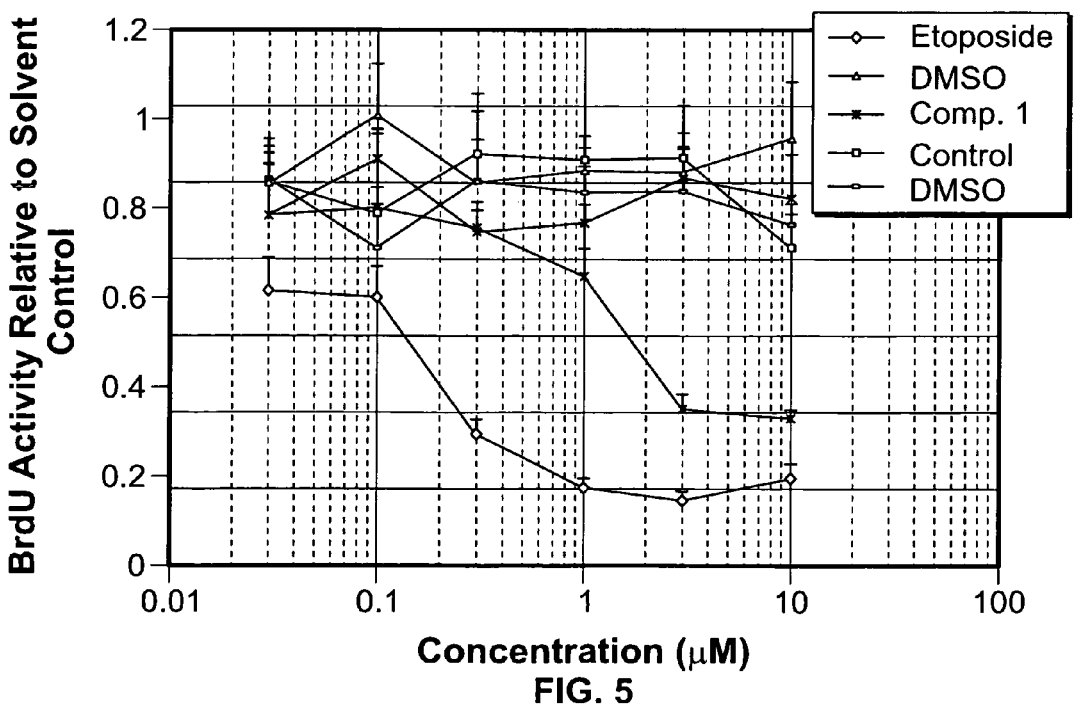
FIG. 5. Antiproliferation activity of compound 1 of the invention utilizing bromodeoxyuridine (BrdU) proliferation assay with a colon cancer cell line.

The A549 (lung cell) tumors responded to the treatment regimen in this study (FIG. 2). Compound 1 slowed tumor growth substantially. Normalizing individual tumor volumes at 35 days with the tumor volume at the start of drug treatment shows that in animals treated with vehicle only, tumor volume increased approximately 7-fold, compared with a 4-fold increase in tumor volume of animals treated with either Compound 1 or Taxol. The mean tumor volume after 27 days of treatment in the vehicle control group was 346.9±164.7 $mm^3$ compared with 223.8±164.1 $mm^3$ for the group treated with Compound 1 administered daily at a dose level 10 mg/kg.

Comparison of tumor response to treatment with chemotherapeutics used in the clinic was determined by calculating the %T/C value as follows: %T/C=the mean tumor volume for treated animals vs. that for control animals×100. Compound 1 and Taxol reduced tumor growth of A549 xenografts with %T/C values of 65% and 59% respectively.

Treatment of SW480 tumors with Compound 1 did not result in a reduced tumor size after daily administration at a dose level of 10 mg/kg administered intraperitoneally. Tumor volume was unchanged in treated animals compared with controls (647.7±500.6 mm$^3$ vs. 677.9±574.3 mm$^3$).

Systemic toxicity, as determined by body weight reduction, was not significant for any of the treated groups (p>0.05 for all groups compared with vehicle control).

Example 3

Bromodeoxyuridine (BrdU) Proliferation Assay

In order to determine the antiproliferative activity of microtubule inhibitors, A549 cells were plated in 96 well plates at 2000 cells/well 24 hours prior to the addition of a compound of the invention in 80 ul growth media (F12K, 10% FBS, Pen/Strep). Prior to addition to cells, compounds were solubilized in 100% DMSO to 5 mM and serially diluted in 6 semi-log steps in 100% DMSO. The diluted compounds were added to cells by two 15.8-fold dilution steps, the first being a dilution into a 23% ethanol/H$_2$O mixture and the second being a dilution into growth media. Finally, these dilutions were followed by a 1:1 dilution onto cells. The resulting final solvent concentration was 0.2% DMSO/0.75% ethanol. Compounds were tested at final concentrations of 10, 3, 1, 0.3, 0.1 and 0.03 uM. Forty-eight hours after the addition of compound, the effects on cellular proliferation were measured using a cell proliferation BrdU ELISA (Roche Molecular Biochemicals, Cat.#1 669 915).

Antiproliferative activity of the tubulin inhibitors was also measured on two other tumor cell lines, SW-480 and MDA-MB-231. The addition of compound and measurements of cellular viability were performed as described above except that the growth media for MBA-MD 231-comprised F12, 10% FBS, Pen/Strep. See FIG. 1 for exemplary IC50 results (μM of compound necessary for 50% inhibition) for compounds 1, 19, 39, 43, 54, 62, 88 and 95. In addition, the following table illustrates IC50 values for exemplary compounds of the invention. Compounds 1, 2, 4, 5, 6, 10, 11, 13, 15, 16, 17, 18, 19, 20, 22, 25, 26, 28, 30, 31, 33, 34, 35, 38, 39, 42, 43, 46, 47, 48, 49, 50, 51, 52, 54, 55, 56, 57, 58, 62, 63, 64, 65, 67, 68, 69, 70, 71, 72, 73, 74, 76, 79, 80, 81, 82, 83, 84, 85, 86, 87, 88, 89, 91, 92, 95, 98, 99, 100, 101, 102, 105, and their pharmaceutically acceptable salts represent particularly active examples of the compounds of the invention and compounds 1, 2, 4, 5, 6, 13, 16, 19, 20, 31, 33, 38, 39, 42, 43, 46, 50, 51, 54, 55, 57, 62, 63, 64, 65, 69, 71, 72, 73, 74, 76, 79, 80, 83, 84, 85, 86, 87, 88, 89, 98, 99, 100, 101, and 102, and their pharmaceutically acceptable salts represent examples of the most active compounds of the invention.

| Compound Number | Assay Result (IC50μM) |
| --- | --- |
| 1 | .664 |
| 2 | .39 |
| 3 | 9999 |
| 4 | .904 |
| 5 | .49 |
| 6 | .329 |
| 7 | 9999 |
| 8 | 9999 |
| 9 | 9999 |
| 10 | 1.334 |
| 11 | 2.198 |
| 12 | 9999 |
| 13 | .38 |
| 14 | 26.73 |
| 15 | 6.699 |
| 16 | .998 |
| 17 | 5.105 |
| 18 | 10.732 |
| 19 | .089 |
| 20 | .071 |
| 21 | 9999 |
| 22 | 5.572 |
| 23 | Not Tested (NT) |
| 24 | 9999 |
| 25 | 6.44 |
| 26 | 5.754 |
| 27 | 9999 |
| 28 | 6.31 |
| 29 | NT |
| 30 | 1.968 |
| 31 | .369 |
| 32 | 9999 |
| 33 | .155 |
| 34 | 1.5 |
| 35 | 2.786 |
| 36 | 9999 |
| 37 | 9999 |
| 38 | .121 |
| 39 | .039 |
| 40 | 9999 |
| 41 | NT |
| 42 | .146 |
| 43 | .438 |
| 44 | 9999 |
| 45 | 9999 |
| 46 | .256 |
| 47 | 7.161 |
| 48 | 1.432 |
| 49 | NT |
| 50 | .927 |
| 51 | .622 |
| 52 | NT |
| 53 | NT |
| 54 | .016 |
| 55 | .15 |
| 56 | NT |
| 57 | .23 |
| 58 | 1.11 |
| 59 | 9999 |
| 60 | 9999 |
| 61 | 9999 |
| 62 | .228 |
| 63 | .211 |
| 64 | .188 |
| 65 | .134 |
| 66 | NT |
| 67 | 18.621 |
| 68 | 6.026 |
| 69 | .093 |
| 70 | 1.611 |
| 71 | .02 |
| 72 | .024 |
| 73 | .202 |
| 74 | .054 |
| 75 | NT |
| 76 | .187 |
| 77 | 9999 |
| 78 | 9999 |
| 79 | .719 |

-continued

| Compound Number | Assay Result (IC50µM) |
|---|---|
| 80 | .151 |
| 81 | NT |
| 82 | NT |
| 83 | .127 |
| 84 | .113 |
| 85 | .044 |
| 86 | .026 |
| 87 | .166 |
| 88 | .06 |
| 89 | .028 |
| 90 | NT |
| 91 | 2.198 |
| 92 | 1.186 |
| 93 | NT |
| 94 | 9999 |
| 95 | 1.469 |
| 96 | 9999 |
| 97 | 9999 |
| 98 | .025 |
| 99 | .086 |
| 100 | .013 |
| 101 | .029 |
| 102 | .385 |
| 103 | NT |
| 104 | 9999 |
| 105 | 8.147 |
| 106 | NT |
| 107 | 9999 |
| 108 | 9999 |
| 109 | 9999 |
| 110 | 9999 |

Example 4

Preparation of Compound 100

Step 1: Preparation of 4-Hydroxy-6-(3,5-Dimethylphenyl)thieno[3,2-d]pyrimidine

3-Amino-2-methoxycarbonyl-4-(3,5-dimethylphenyl) thiophene (prepared according to H. Hartmann and J. Liebscher, Synthesis, 275 (1984)) (17.2 g) was heated under reflux with formamide (150 mL) for 5.5 hours. The mixture was cooled to room temperature and then poured onto ice. The solid precipitate was filtered off and crystallized from ethanol.

MW=256 confirmed by LC-MS; tr=17.31 min; MH+=257; NMR: 2.30 (s, 6H), 7.07 (broad s, 1H), 7.45 (broad s, 2H), 7.78 (s, 1H), 8.15 (s, 1H).

Step 2: Preparation of 4-Chloro-6-(3,5-Dimethylphenyl) thieno[3,2-d]pyrimidine

The hydroxy compound prepared in Step 1 was treated with phosphorous oxychloride (150 mL) and diisopropylethylamine (2 mL). The mixture was then heated at 100° C. for 4 hours. The solvents were evaporated under reduced pressure and the residue was carefully treated with ice water. The resulting solid was filtered off and crystallized from ethanol.

MW=274 confirmed by LC-MS; tr=24.38 min; MH+=275/277; NMR: 2.30 (s, 6H), 7.18 (s, 1H), 7.60 (s, 2H), 8.08 (s, 1H), 9.00 (s, 1H).

Step 3: Preparation of 4-Hydrazino-6-(3,5-dimethylphenyl)thieno[3,2-d]pyrimidine The chloro compound prepared in Step 2 (0.7 g) was treated with 2-propanol (15 mL) and anhydrous hydrazine (1.0 mL) with shaking at 85° C. overnight. The reaction mixture was cooled to room temperature and then poured into ice water. The resulting solid was filtered off and washed thoroughly with water. The crude product was crystallized from ethanol with the aid of decolorizing charcoal to give the hydrazino compound, 0.47 g as a buff-colored solid. MW=270; confirmed by LC-MS; tr=13.36 min, MH+=271; NMR: 2.35 (s, 6H), 4.85 (broad s, 2H), 7.05 (s, 1H), 7.42 (s, 2H), 7.61 (s, 1H), 8.95 (s,1H).

Step 4: Preparation of N-(2-Methoxyethyl)-2-[6-(3,5-dimethylphenyl)]thieno[3,2-d]pyrimidinyl-4-yl]-hydrazine carbothioamide (compound 100)

Figure 6A:
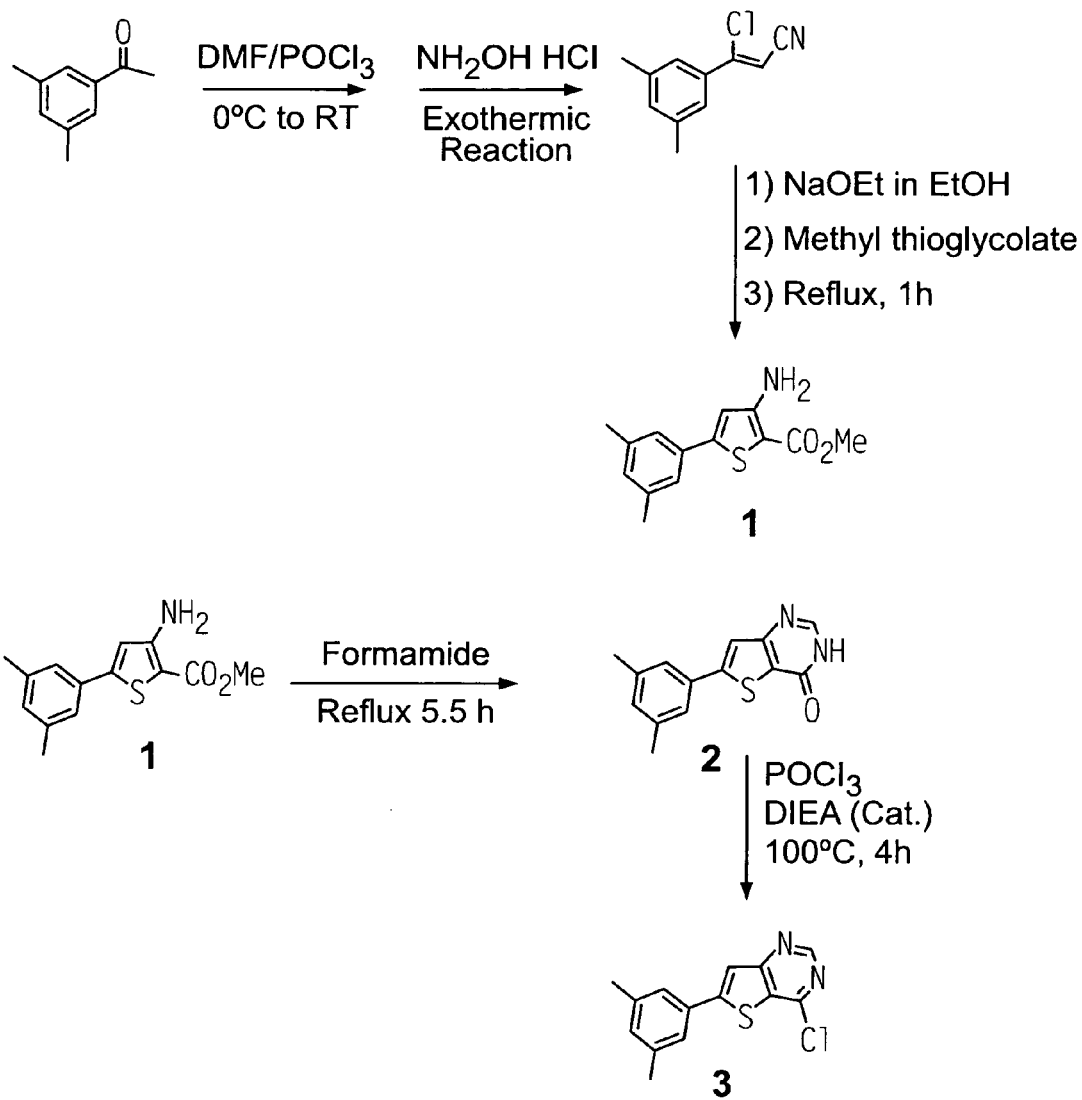
FIGS. 6a and 6b. Synthesis flowchart for an exemplary compound of the invention (compound 100).
Figure 6B:
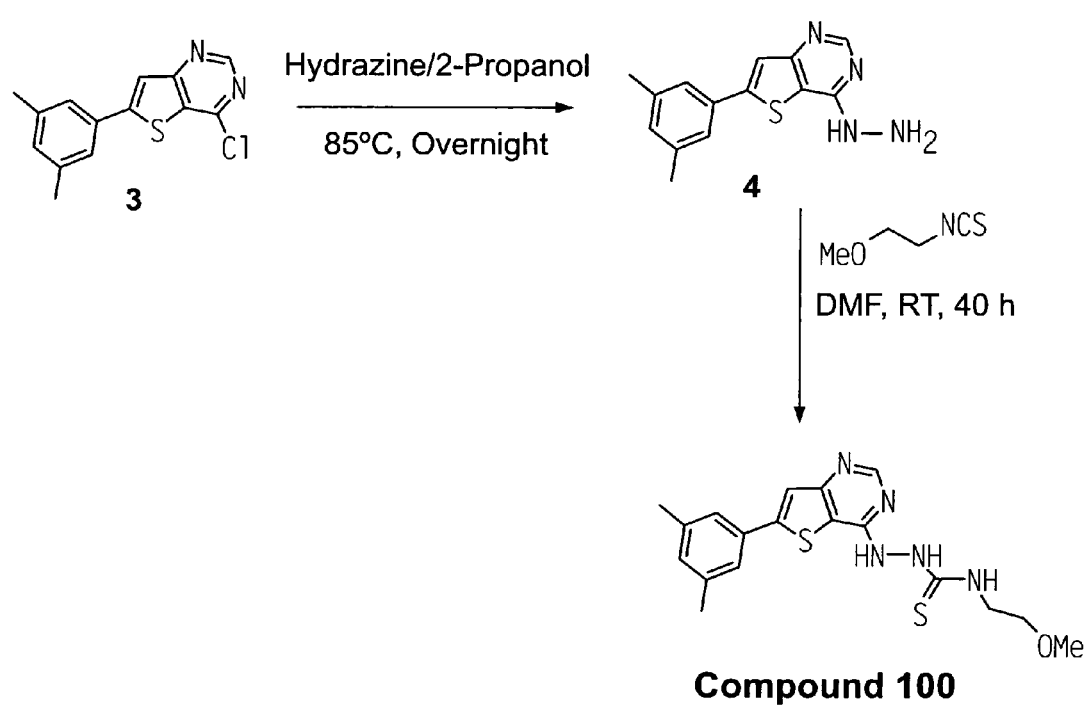

The hydrazino compound prepared in Step 3, 40 mg, was dissolved in anhydrous DMF (2 mL). 2-Methoxyethyl-isothiocyanate (60 µL) was added and the mixture shaken for 40 hours at room temperature. Water was then added and the precipitated product was filtered off, washed with diethyl ether and dried under vacuum. MW=387; confirmed by LC-MS; tr=14.94, MH+=388; NMR: 2.32 (s, 6H), 3.28 (s, 3H), 3.42 (m, 2H), 3.62 (m, 2H), 7.10 (s, 1H), 7.39 (s, 2H), 7.74 (s, 1H), 8.38 (broad s, 1H), 8.45 (s, 1H, exchanges with D2O), 9.68 (s, 1H, exchanges with D2O), 9.78 (broad s, exchanges with $D_2O$). See FIGS. 6a and 6b.

General Experimental Methods

NMR spectra were obtained on a Varian 300 MHz Mercury system with methyl-sulfoxide-d6 as the solvent. LC-MS was performed on a Waters Micromass ZQ instrument with electrospray ionization. The HPLC component was a Waters 2690 Separation Module coupled to a Waters Model 996 photodiode array detector. The HPLC method utilized a 2.1×250 mm 5 µM C-18 reversed phase column (Alltech) with a flow rate of 0.25 mL/min and a gradient of 5–85% acetonitrile with water containing 0.1% trifluoroacetic acid over 15 minutes. The gradient then ramps to 100% acetonitrile and continues at 100% acetonitrile for 25 minutes.

What is claimed is:

1. A compound of the formula (1)

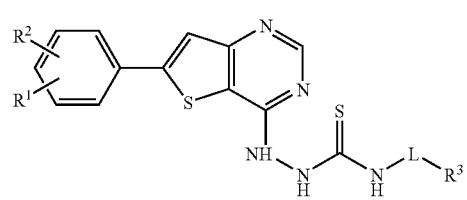

(1)

or a pharmaceutically acceptable salt thereof, wherein
$R^1$ and $R^2$ are independently selected from the group consisting of —H, halo, $C_1$–$C_6$ alkyl, halogenated-$C_1$–$C_6$-alkyl, and —$OR^4$, or
$R^1$ and $R^2$ together with the carbon to which they are attached form a heterocyclyl;
$R^4$ is selected from the group consisting of $C_1$–$C_6$ alkyl, or
$R^4$ is aryl or aryl-$C_1$–$C_6$-alkyl, wherein the aryl portion is optionally substituted with one to four groups independently selected from halo, cyano, oxo, carboxy, formyl, nitro, amino, amidino, guanidino, —$(CH_2)_5$—$NR^{30}R^{31}$, or
$C_1$–$C_5$ alkyl or alkenyl or arylalkyl imino, carbamoyl, azido, carboxamido, mercapto, hydroxy, hydroxyalkyl, alkylaryl, arylalkyl, $C_1$–$C_8$ alkyl, $C_1$–$C_8$ alkenyl, $C_1$–$C_8$ alkoxy, $C_1$–$C_8$ alkoxycarbonyl, aryloxycarbonyl, $C_2$–$C_8$ acyl, $C_2$–$C_8$ acylamino, $C_1$–$C_8$ alkylthio, arylalkylthio, arylthio, $C_1$–$C_8$ alkylsulfinyl, arylalkylsulfinyl, arylsulfinyl, $C_1$–$C_8$ alkylsulfonyl, arylalkylsulfonyl, arylsulfonyl, $C_0$–$C_6$ N-alkyl carbamoyl, $C_2$–$C_{15}$ N,N-dialkylcarbamoyl, $C_3$–$C_7$ cycloalkyl, aroyl, aryloxy, arylalkyl ether, aryl, aryl fused to a cycloalkyl or heterocycle or another aryl ring, $C_3$–$C_7$ heterocycle, or any of these rings fused or spiro-fused to a cycloalkyl, heterocyclyl, or aryl, each of which is optionally substituted with one or more groups independently selected from halo, cyano, oxo, carboxy, formyl, nitro, amino, amidino or guanidine;

$R^{30}$ and $R^{31}$ are each independently hydrogen, cyano, oxo, carboxamido, amidino, $C_1$–$C_8$ hydroxyalkyl, $C_1$–$C_3$ alkylaryl, aryl-$C_1$–$C_3$ alkyl, $C_1$–$C_8$ alkyl, $C_1$–$C_8$ alkenyl, $C_1$–$C_8$ alkoxycarbonyl, aryloxycarbonyl, aryl-$C_1$–$C_3$ alkoxycarbonyl, $C_2$–$C_8$ acyl, $C_1$–$C_8$ alkylsulfonyl, arylalkylsulfonyl, arylsulfonyl, aroyl, aryl, cycloalkyl, heterocyclyl, or heteroaryl, wherein each optionally substituted with one more groups selected from halo, cyano, oxo, carboxy, formyl, nitro, amino, amidino, guanidine, or $R^{30}$ and $R^{31}$ taken together with the N to which they are attached form a heterocyclyl or heteroaryl, each of which is optionally substituted with from 1 to 3 substituents selected from halo, cyano, oxo, carboxy, formyl, nitro, amino, amidino, guanidine;

L is selected from the group consisting of a covalent bond, $C_1$–$C_6$ alkyl, —C(O)—, and —(CH$_2$)$_{0-3}$C(H)(R$^5$)—;

$R^5$ is selected from the group consisting of $C_1$–$C_6$ alkyl, aryl, aryl-$C_1$–$C_6$-alkyl, —$R^6$—S—$R^7$, —$R^6$—C(O)OR$^7$, and —$R^6$—O—$R^7$, wherein $R^6$ and $R^7$ are $C_1$–$C_6$ alkyl;

$R^3$ is selected from the group consisting of H, $C_1$–$C_6$ alkyl, hydroxy $C_1$–$C_6$ alkyl, —OR$^8$, —C(O)OR$^9$, —N(R$^{10}$)R$^{11}$, or $R^3$ is $C_3$–$C_8$-cycloalkyl, heterocyclyl, aryl, heteroaryl, arylalkyl, each of which is optionally substituted with one to four groups selected from halo, cyano, oxo, carboxy, formyl, nitro, amino, amidino, guanidino, —(CH$_2$)$_s$—NR$^{30}$R$^{31}$, or $C_1$–$C_5$ alkyl or alkenyl or arylalkyl imino, carbamoyl, azido, carboxamido, mercapto, hydroxy, hydroxyalkyl, alkylaryl, arylalkyl, $C_1$–$C_8$ alkyl, $C_1$–$C_8$ alkenyl, $C_1$–$C_8$ alkoxy, $C_1$–$C_8$ alkoxycarbonyl, aryloxycarbonyl, $C_2$–$C_8$ acyl, $C_2$–$C_8$ acylamino, $C_1$–$C_8$ alkylthio, arylalkylthio, arylthio, $C_1$–$C_8$ alkylsulfinyl, arylalkylsulfinyl, arylsulfinyl, $C_1$–$C_8$ alkylsulfonyl, arylalkylsulfonyl, arylsulfonyl, $C_0$–$C_6$ N-alkyl carbamoyl, $C_2$–$C_{15}$ N,N-dialkylcarbamoyl, $C_3$–$C_7$ cycloalkyl, aroyl, aryloxy, arylalkyl ether, aryl, aryl fused to a cycloalkyl or heterocycle or another aryl ring, $C_3$–$C_7$ heterocycle, or any of these rings fused or spiro-fused to a cycloalkyl, heterocyclyl, or aryl, each of which is optionally substituted with one or more groups independently selected from halo, cyano, oxo, carboxy, formyl, nitro, amino, amidino or guanidine;

$R^8$ is $C_1$–$C_6$ alkyl or hydroxy $C_1$–$C_6$ alkyl; and
$R^9$, $R^{10}$, and $R^{11}$ are $C_1$–$C_6$ alkyl.

2. The compound of claim 1 wherein $R^2$ is H.

3. The compound of claim 1 wherein $R^1$ and $R^2$ are independently selected from the group consisting of H, halogen, $C_1$–$C_6$ alkyl, and —OR$^4$, wherein $R^4$ is $C_1$–$C_6$ alkyl, or wherein $R^1$ and $R^2$ together with the carbon to which they are attached form a heterocyclyl moiety.

4. The compound of claim 1 wherein $R^1$ and $R^2$ are independently selected from the group consisting of H, —Cl, —CH$_3$, and —OCH$_3$, or wherein $R^1$ and $R^2$ together with the carbon to which they are attached form a 5- or 6-membered heterocyclyl moiety.

5. The compound of claim 1 wherein L is a covalent bond.

6. The compound of claim 1 wherein L is $C_1$–$C_6$ alkyl.

7. The compound of claim 1 wherein L is —(CH$_2$)$_{0-1}$C(H)(R$^5$)—.

8. The compound of claim 5 wherein $R^3$ is selected from the group consisting of H, hydroxy alkyl, or $R^3$ is cycloalkyl, heterocyclyl, aryl, or heteroaryl, each of which is optionally substituted with one to four groups independently selected from halo, cyano, oxo, carboxy, formyl, nitro, amino, amidino, guanidino, —(CH$_2$)$_s$—NR$^{30}$R$^{31}$, or $C_1$–$C_5$ alkyl or alkenyl or arylalkyl imino, carbamoyl, azido, carboxamido, mercapto, hydroxy, hydroxyalkyl, alkylaryl, arylalkyl, $C_1$–$C_8$ alkyl, $C_1$–$C_8$ alkenyl, $C_1$–$C_8$ alkoxy, $C_1$–$C_8$ alkoxycarbonyl, aryloxycarbonyl, $C_2$–$C_8$ acyl, $C_2$–$C_8$ acylamino, $C_1$–$C_8$ alkylthio, arylalkylthio, arylthio, $C_1$–$C_8$ alkylsulfinyl, arylalkylsulfinyl, arylsulfinyl, $C_1$–$C_8$ alkylsulfonyl, arylalkylsulfonyl, arylsulfonyl, $C_0$–$C_6$ N-alkyl carbamoyl, $C_2$–$C_{15}$ N,N-dialkylcarbamoyl, $C_3$–$C_7$ cycloalkyl, aroyl, aryloxy, arylalkyl ether, aryl, aryl fused to a cycloalkyl or heterocycle or another aryl ring, $C_3$–$C_7$ heterocycle, or any of these rings fused or spiro-fused to a cycloalkyl, heterocyclyl, or aryl, each of which is optionally substituted with one or more groups independently selected from halo, cyano, oxo, carboxy, formyl, nitro, amino, amidino or guanidine.

9. The compound of claim 8 wherein $R^3$ is H, or $R^3$ is $C_3$–$C_6$ cycloalkyl, 5- to 6-membered heterocyclyl, or aryl, each of which is optionally substituted with one to four groups independently selected from halo, cyano, oxo, carboxy, formyl, nitro, amino, amidino, guanidino, —(CH$_2$)$_s$—NR$^{30}$R$^{31}$, or $C_1$–$C_5$ alkyl or alkenyl or arylalkyl imino, carbamoyl, azido, carboxamido, mercapto, hydroxy, hydroxyalkyl, alkylaryl, arylalkyl, $C_1$–$C_8$ alkyl, $C_1$–$C_8$ alkenyl, $C_1$–$C_8$ alkoxy, $C_1$–$C_8$ alkoxycarbonyl, aryloxycarbonyl, $C_2$–$C_8$ acyl, $C_2$–$C_8$ acylamino, $C_1$–$C_8$ alkylthio, arylalkylthio, arylthio, $C_1$–$C_8$ alkylsulfinyl, arylalkylsulfinyl, arylsulfinyl, $C_1$–$C_8$ alkylsulfonyl, arylalkylsulfonyl, arylsulfonyl, $C_0$–$C_6$ N-alkyl carbamoyl, $C_2$–$C_{15}$ N,N-dialkylcarbamoyl, $C_3$–$C_7$ cycloalkyl, aroyl, aryloxy, arylalkyl ether, aryl, aryl fused to a cycloalkyl or heterocycle or another aryl ring, $C_3$–$C_7$ heterocycle, or any of these rings fused or spiro-fused to a cycloalkyl, heterocyclyl, or aryl, each of which is optionally substituted with one or more groups independently selected from halo, cyano, oxo, carboxy, formyl, nitro, amino, amidino or guanidine.

10. The compound of claim 9 wherein $R^3$ is selected from the group consisting of cyclopropyl, benzyl, or $R^3$ is benzyl optionally substituted with one to four groups independently selected from halo, cyano, oxo, carboxy, formyl, nitro, amino, amidino, guanidino, —(CH$_2$)$_s$—NR$^{30}$R$^{31}$, or $C_1$–$C_5$ alkyl or alkenyl or arylalkyl imino, carbamoyl, azido, carboxamido, mercapto, hydroxy, hydroxyalkyl, alkylaryl, arylalkyl, $C_1$–$C_8$ alkyl, $C_1$–$C_8$ alkenyl, $C_1$–$C_8$ alkoxy, $C_1$–$C_8$ alkoxycarbonyl, aryloxycarbonyl, $C_2$–$C_8$ acyl, $C_2$–$C_8$ acylamino, $C_1$–$C_8$ alkylthio, arylalkylthio, arylthio, $C_1$–$C_8$ alkylsulfinyl, arylalkylsulfinyl, arylsulfinyl, $C_1$–$C_8$ alkylsulfonyl, arylalkylsulfonyl, arylsulfonyl, $C_0$–$C_6$ N-alkyl carbamoyl, $C_2$–$C_{15}$ N,N-dialkylcarbamoyl, $C_3$–$C_7$ cycloalkyl, aroyl, aryloxy, arylalkyl ether, aryl, aryl fused to a cycloalkyl or heterocycle or another aryl ring, $C_3$–$C_7$ heterocycle, or any of these rings fused or spiro-fused to a cycloalkyl, heterocyclyl, or aryl, each of which is optionally substituted with one or more groups independently selected from halo, cyano, oxo, carboxy, formyl, nitro, amino, amidino or guanidine.

11. The compound of claim 10 wherein $R^3$ is benzyl optionally substituted with one to three substituents independently selected from the group consisting of —$CH_3$, —$CO_2H$, —$CO_2CH_2CH_3$, —$OCH_3$, —$CF_3$, —CN, —$NO_2$, —$SO_2NH_2$, and —Cl.

12. The compound of claim 6 wherein
   $R^3$ is selected from the group consisting of H, —$OR^8$, —C(O)$OR^9$, and —N($R^{10}$)$R^{11}$, or
   $R^3$ is cycloalkyl, heterocyclyl, aryl or heteroaryl, each of which is optionally substituted with one to four groups independently selected from halo, cyano, oxo, carboxy, formyl, nitro, amino, amidino, guanidino, —$(CH_2)_s$—$NR^{30}R^{31}$, or
   $C_1$–$C_5$ alkyl or alkenyl or arylalkyl imino, carbamoyl, azido, carboxamido, mercapto, hydroxy, hydroxyalkyl, alkylaryl, arylalkyl, $C_1$–$C_8$ alkyl, $C_1$–$C_8$ alkenyl, $C_1$–$C_8$ alkoxy, $C_1$–$C_8$ alkoxycarbonyl, aryloxycarbonyl, $C_2$–$C_8$ acyl, $C_2$–$C_8$ acylamino, $C_1$–$C_8$ alkylthio, arylalkylthio, arylthio, $C_1$–$C_8$ alkylsulfinyl, arylalkylsulfinyl, arylsulfinyl, $C_1$–$C_8$ alkylsulfonyl, arylalkylsulfonyl, arylsulfonyl, $C_0$–$C_6$ N-alkyl carbamoyl, $C_2$–$C_{15}$ N,N-dialkylcarbamoyl, $C_3$–$C_7$ cycloalkyl, aroyl, aryloxy, arylalkyl ether, aryl, aryl fused to a cycloalkyl or heterocycle or another aryl ring, $C_3$–$C_7$ heterocycle, or any of these rings fused or spiro-fused to a cycloalkyl, heterocyclyl, or aryl, each of which is optionally substituted with one or more groups independently selected from halo, cyano, oxo, carboxy, formyl, nitro, amino, amidino or guanidine.

13. The compound of claim 12 wherein
   $R^3$ is selected from the group consisting of H, $C_3$–$C_6$ cycloalkyl, 4- to 6-membered heterocyclyl, —$OR^8$, or
   $R^3$ is optionally benzyl, each of which is optionally substituted with one to four groups independently selected from halo, cyano, oxo, carboxy, formyl, nitro, amino, amidino, guanidino, —$(CH_2)_s$—$NR^{30}R^{31}$, or
   $C_1$–$C_5$ alkyl or alkenyl or arylalkyl imino, carbamoyl, azido, carboxamido, mercapto, hydroxy, hydroxyalkyl, alkylaryl, arylalkyl, $C_1$–$C_8$ alkyl, $C_1$–$C_8$ alkenyl, $C_1$–$C_8$ alkoxy, $C_1$–$C_8$ alkoxycarbonyl, aryloxycarbonyl, $C_2$–$C_8$ acyl, $C_2$–$C_8$ acylamino, $C_1$–$C_8$ alkylthio, arylalkylthio, arylthio, $C_1$–$C_8$ alkylsulfinyl, arylalkylsulfinyl, arylsulfinyl, $C_1$–$C_8$ alkylsulfonyl, arylalkylsulfonyl, arylsulfonyl, $C_0$–$C_6$ N-alkyl carbamoyl, $C_2$–$C_{15}$ N,N-dialkylcarbamoyl, $C_3$–$C_7$ cycloalkyl, aroyl, aryloxy, arylalkyl ether, aryl, aryl fused to a cycloalkyl or heterocycle or another aryl ring, $C_3$–$C_7$ heterocycle, or any of these rings fused or spiro-fused to a cycloalkyl, heterocyclyl, or aryl, each of which is optionally substituted with one or more groups independently selected from halo, cyano, oxo, carboxy, formyl, nitro, amino, amidino or guanidine.

14. The compound of claim 13 wherein
   $R^3$ is H or —$OCH_3$, or
   $R^3$ is 5- to 6-membered heterocyclyl or benzyl, each of which is optionally substituted with one to four groups independently selected from halo, cyano, oxo, carboxy, formyl, nitro, amino, amidino, guanidino, —$(CH_2)_s$—$NR^{30}R^{31}$, or
   $C_1$–$C_5$ alkyl or alkenyl or arylalkyl imino, carbamoyl, azido, carboxamido, mercapto, hydroxy, hydroxyalkyl, alkylaryl, arylalkyl, $C_1$–$C_8$ alkyl, $C_1$–$C_8$ alkenyl, $C_1$–$C_8$ alkoxy, $C_1$–$C_8$ alkoxycarbonyl, aryloxycarbonyl, $C_2$–$C_8$ acyl, $C_2$–$C_8$ acylamino, $C_1$–$C_8$ alkylthio, arylalkylthio, arylthio, $C_1$–$C_8$ alkylsulfinyl, arylalkylsulfinyl, arylsulfinyl, $C_1$–$C_8$ alkylsulfonyl, arylalkylsulfonyl, arylsulfonyl, $C_0$–$C_6$ N-alkyl carbamoyl, $C_2$–$C_{15}$ N,N-dialkylcarbamoyl, $C_3$–$C_7$ cycloalkyl, aroyl, aryloxy, arylalkyl ether, aryl, aryl fused to a cycloalkyl or heterocycle or another aryl ring, $C_3$–$C_7$ heterocycle, or any of these rings fused or spiro-fused to a cycloalkyl, heterocyclyl, or aryl, each of which is optionally substituted with one or more groups independently selected from halo, cyano, oxo, carboxy, formyl, nitro, amino, amidino or guanidine.

15. A compound of claim 1 selected from the group consisting of:

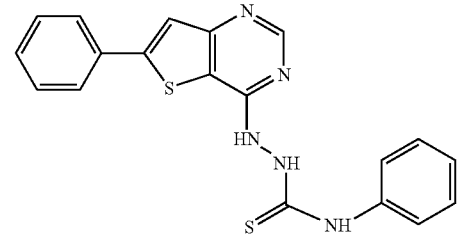

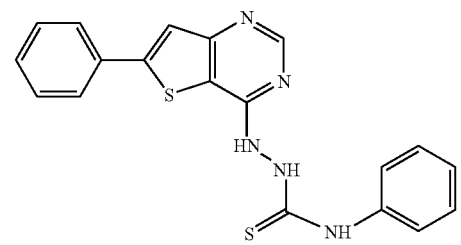

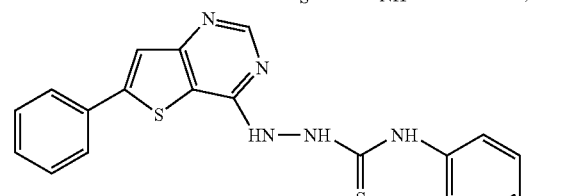

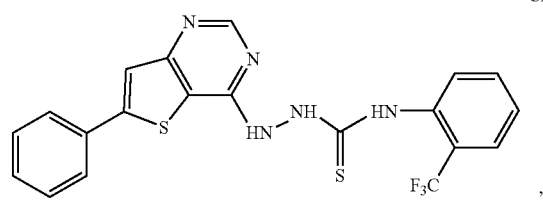

-continued
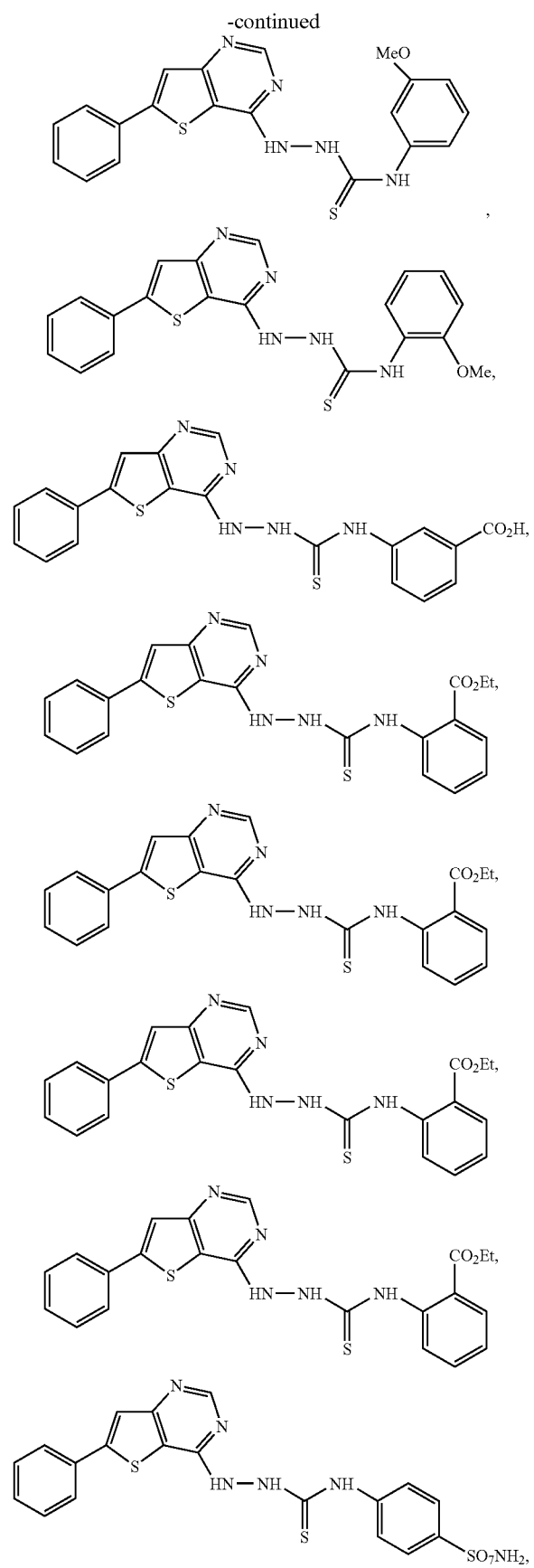
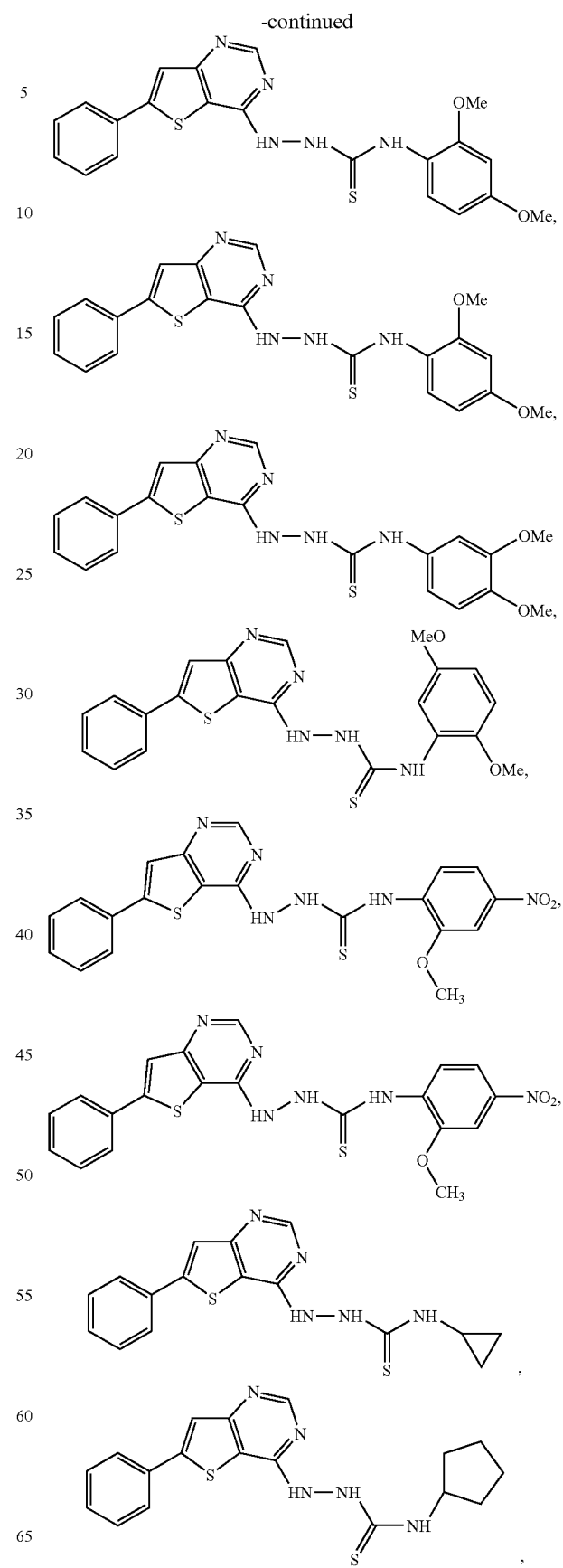

-continued

-continued
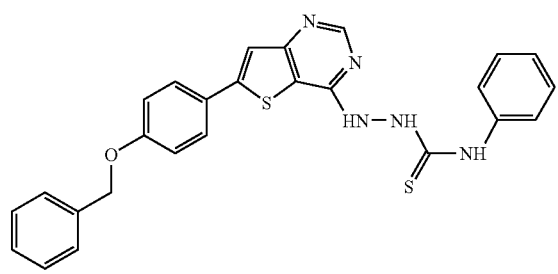
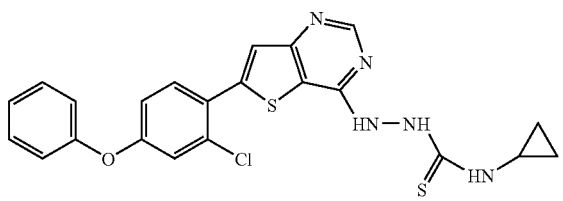
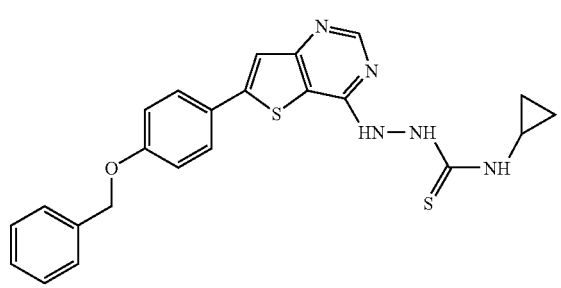
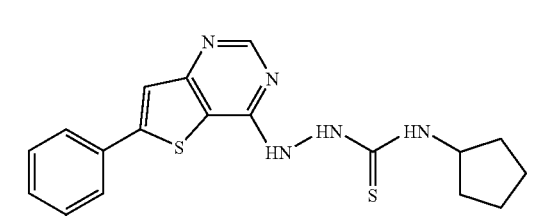
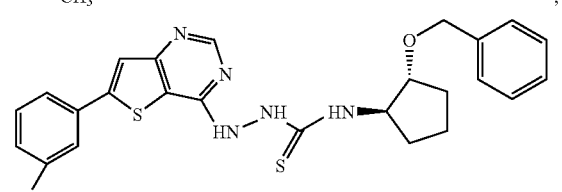
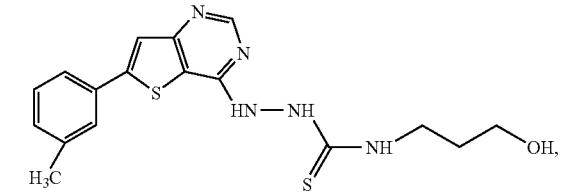
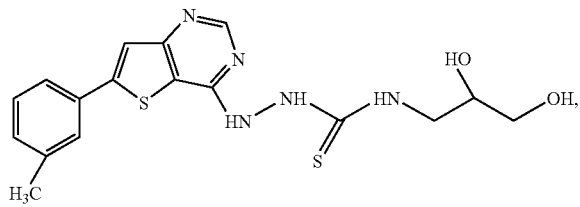
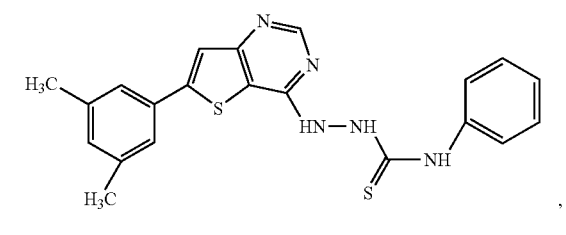

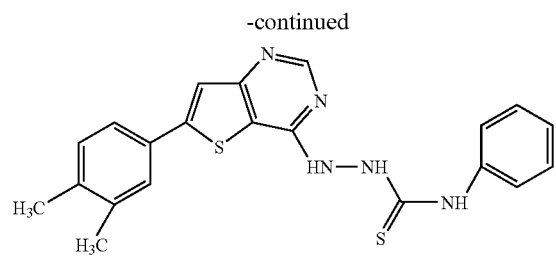
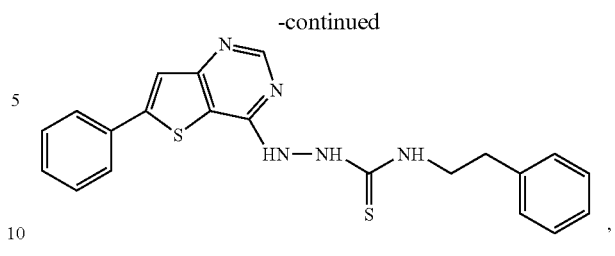
,
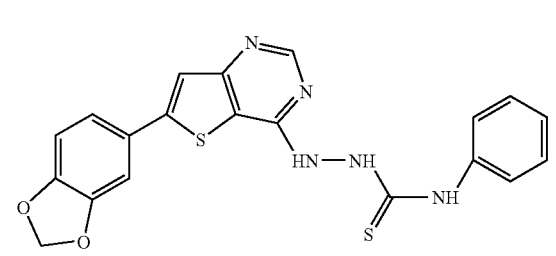
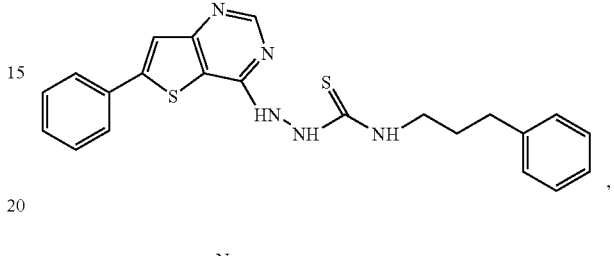
,
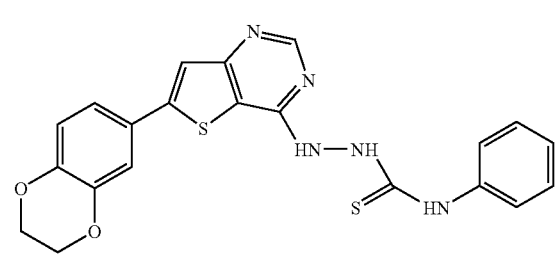
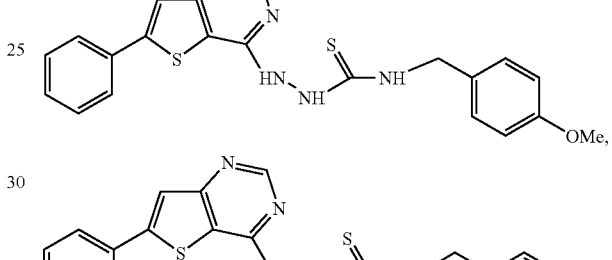
,
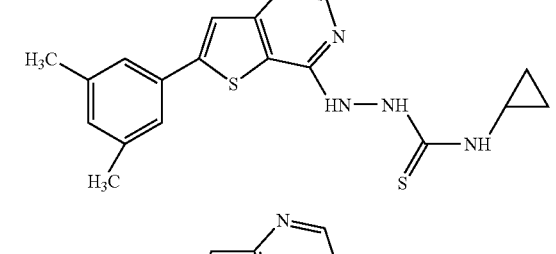
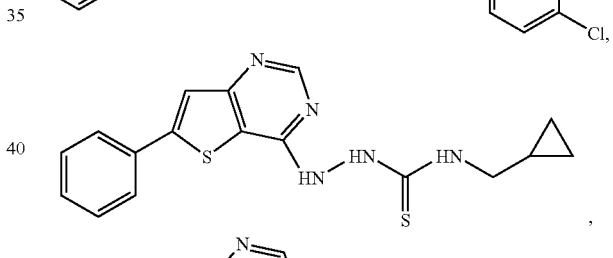
,
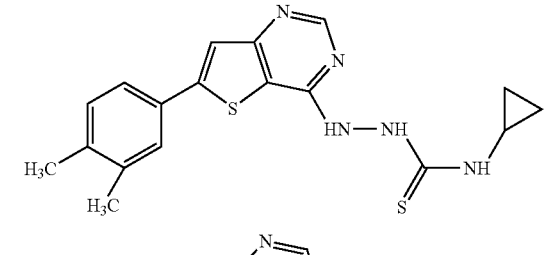
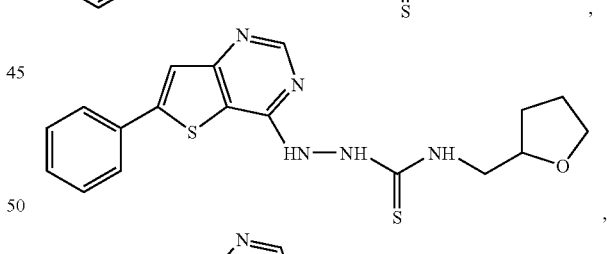
,
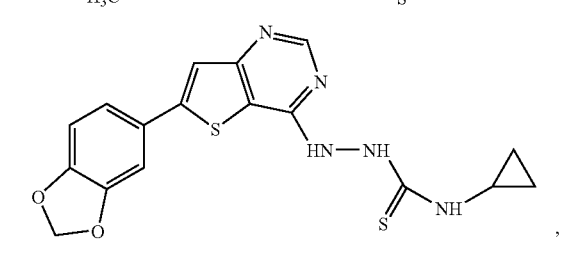
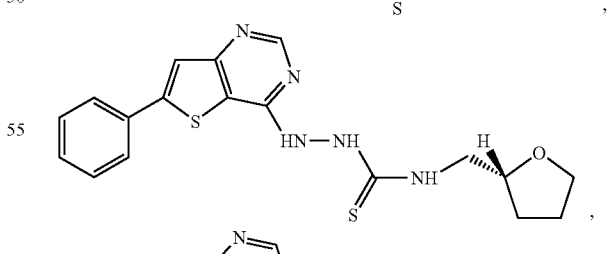
,
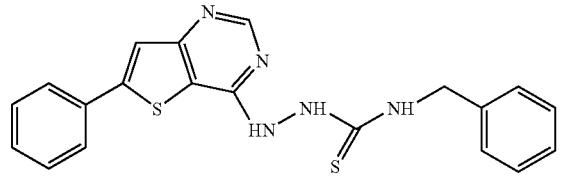
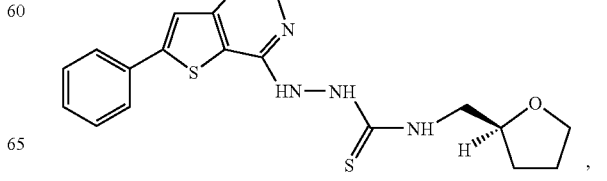
,

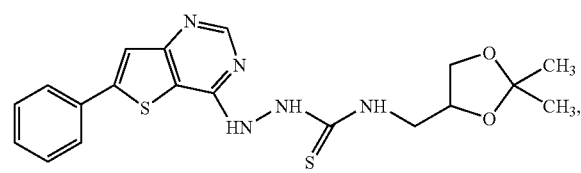
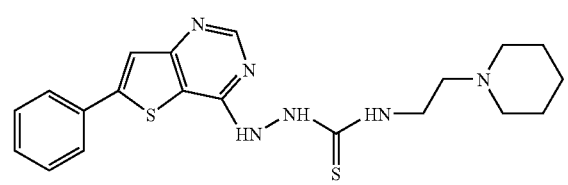
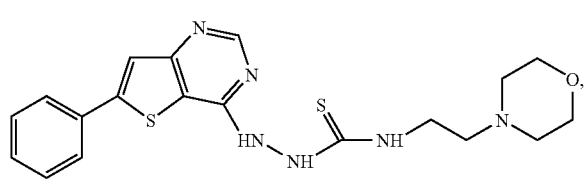
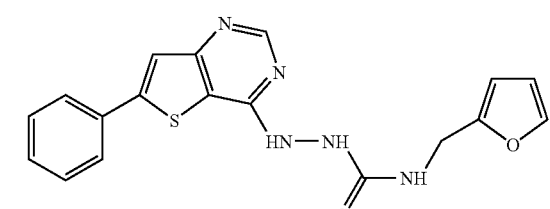
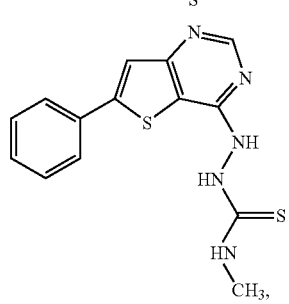
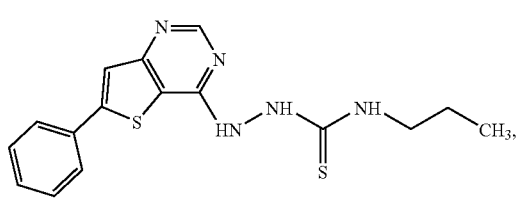
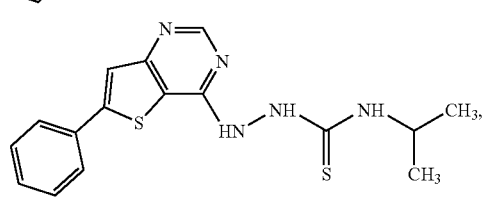
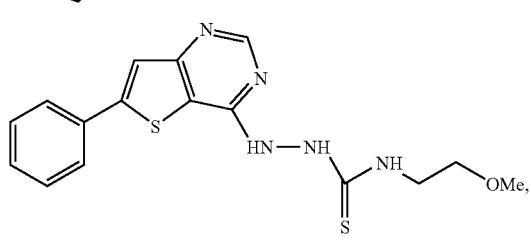
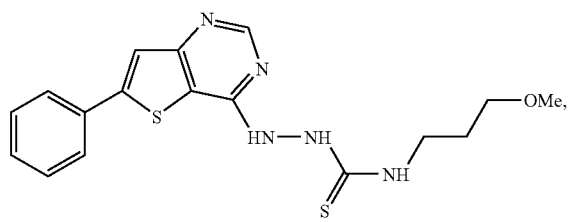
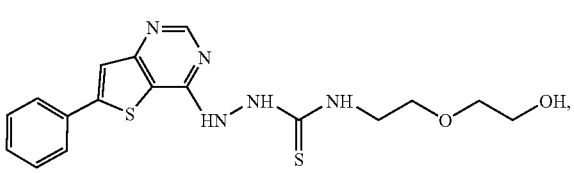
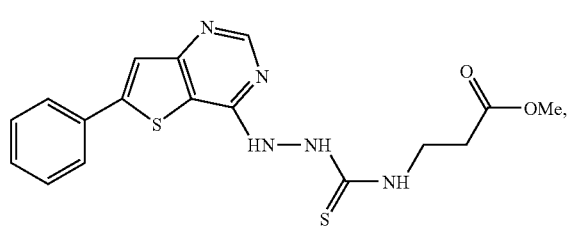
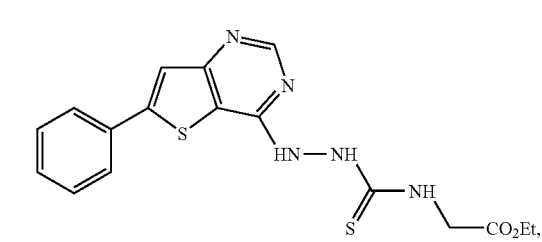
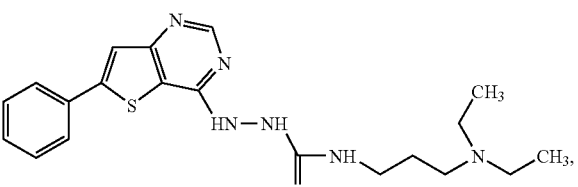
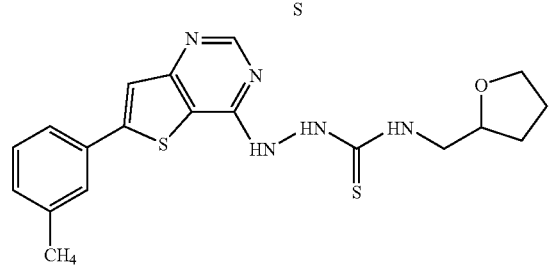
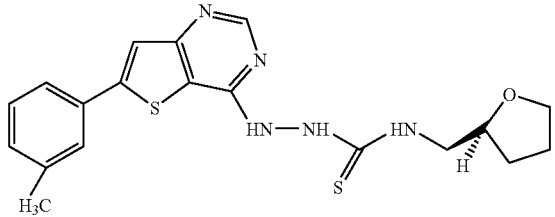

-continued
85
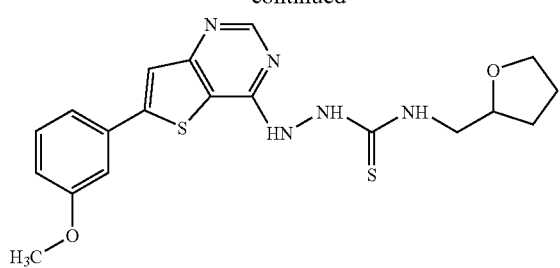
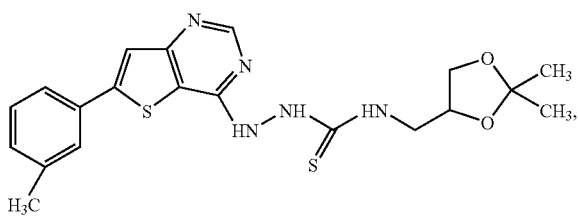
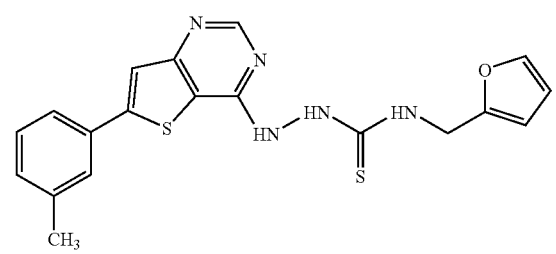
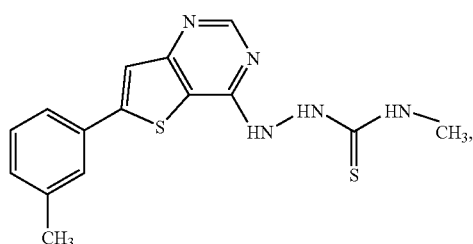
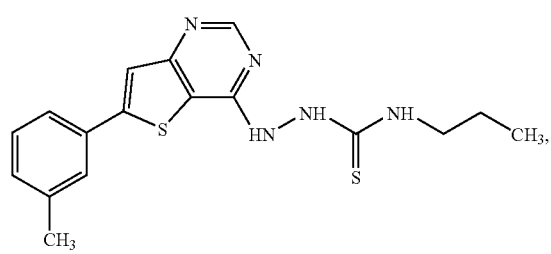
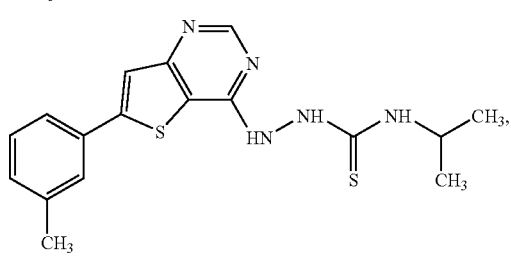
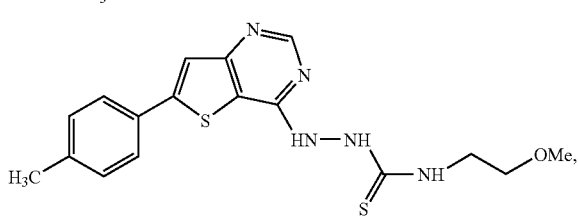
86
-continued
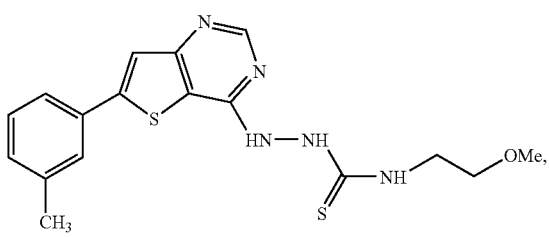
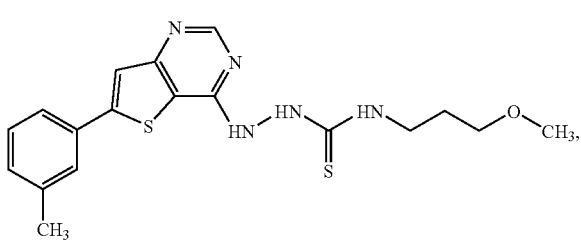
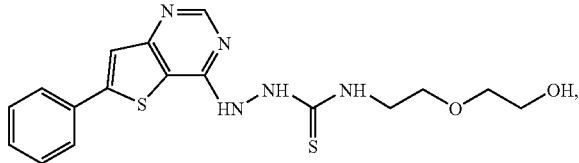
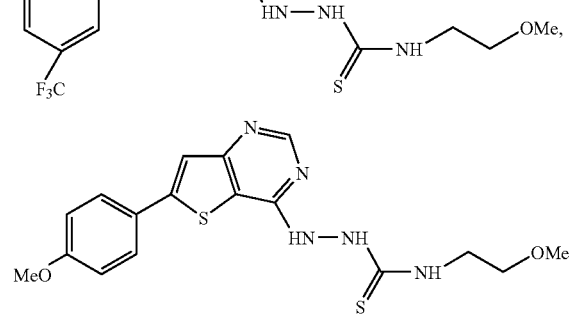
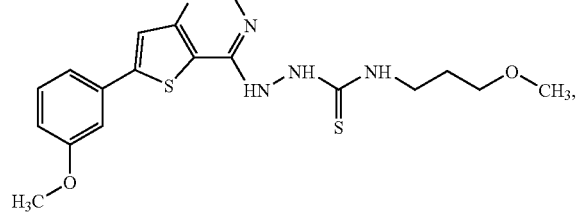

-continued
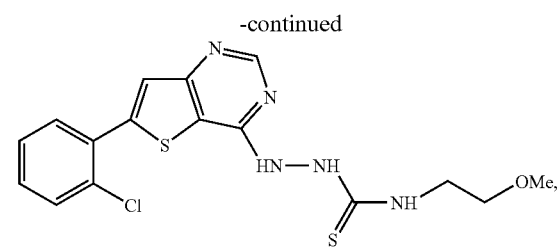
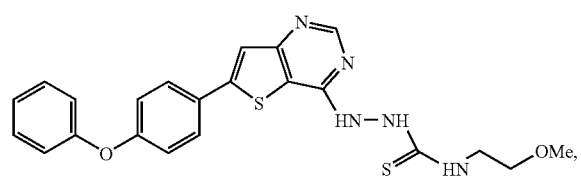
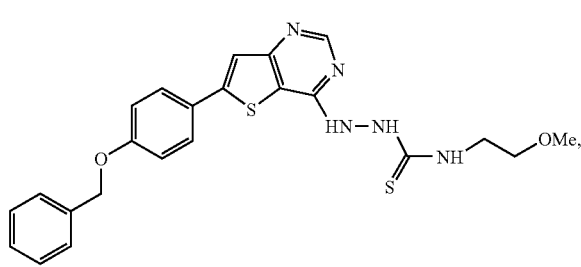
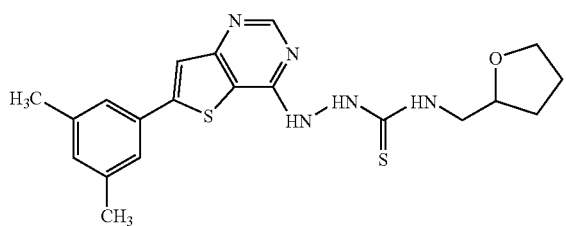
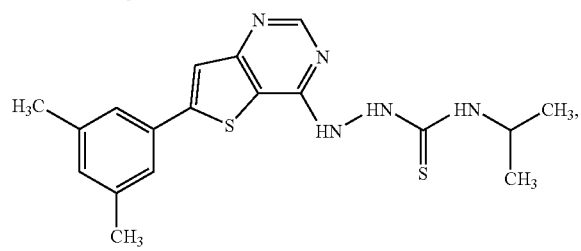
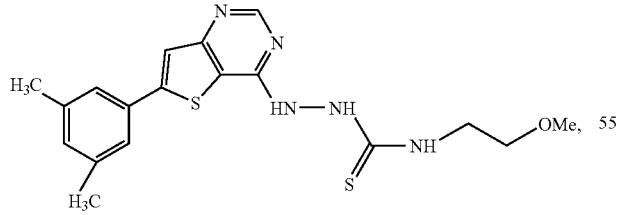
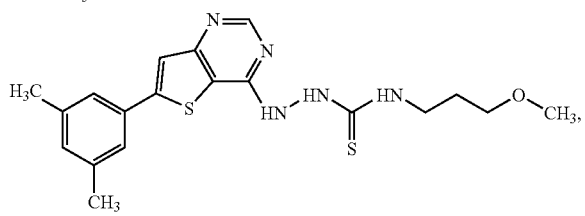
-continued
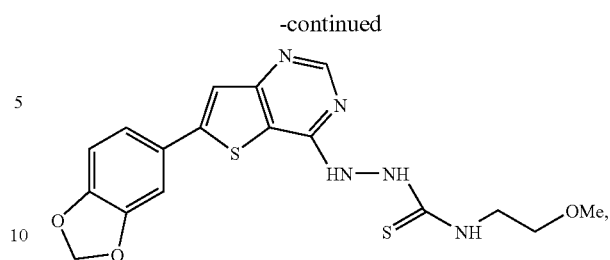
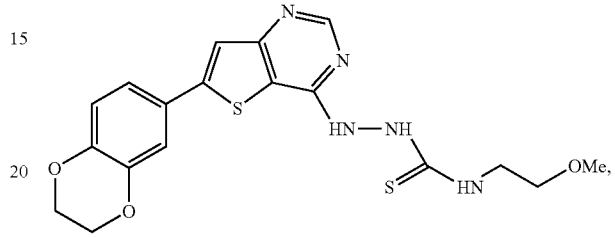
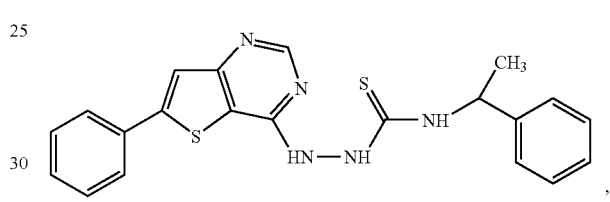
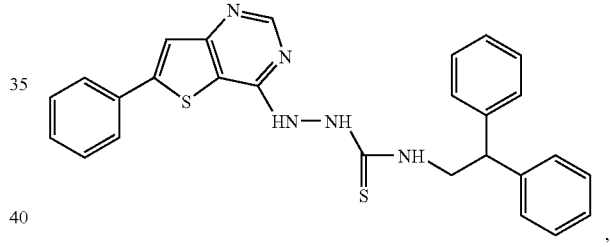
and their pharmaceutically acceptable salts.
16. A compound of claim 15 selected from the group consisting of:
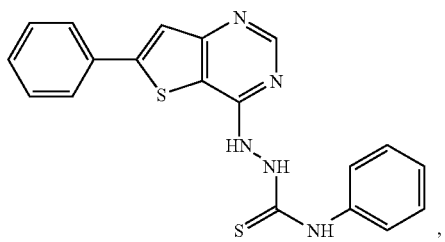
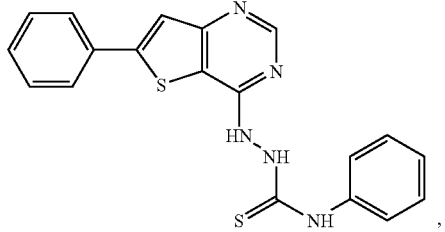

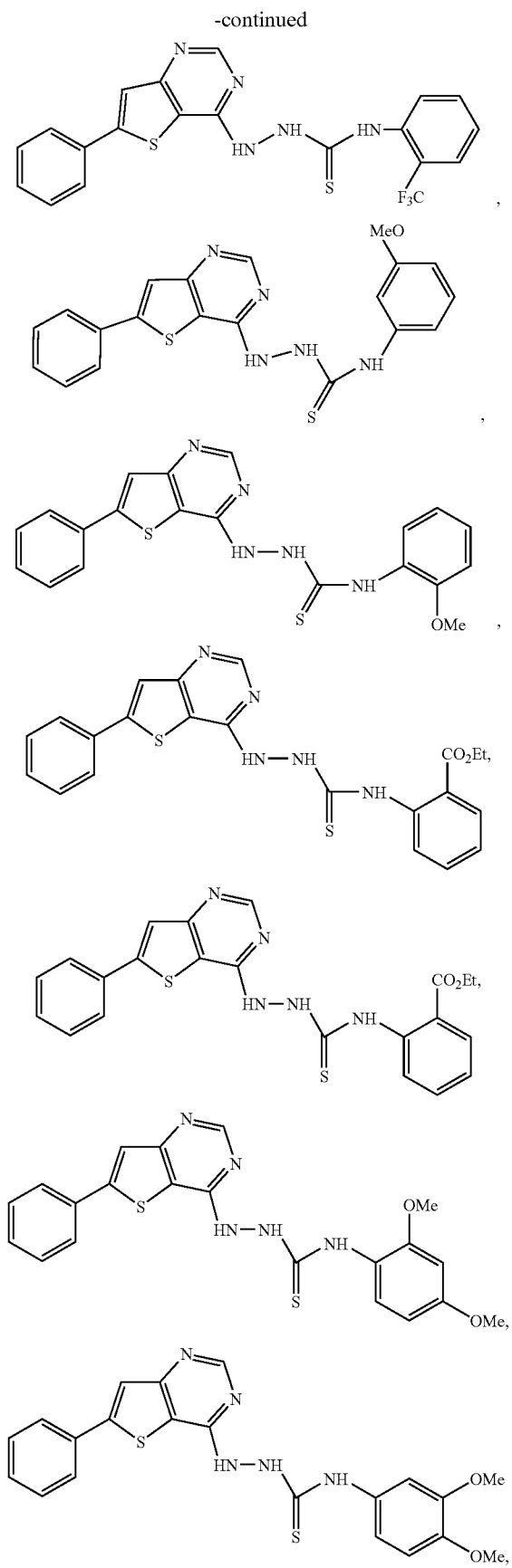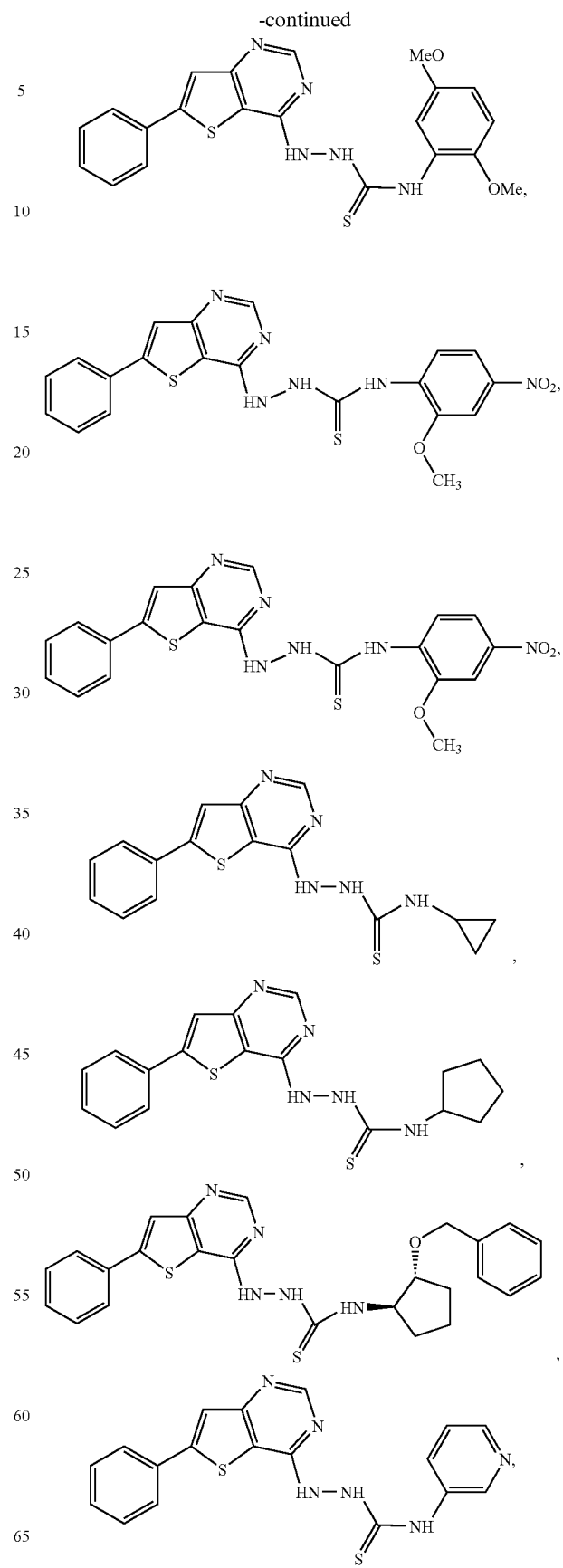

-continued
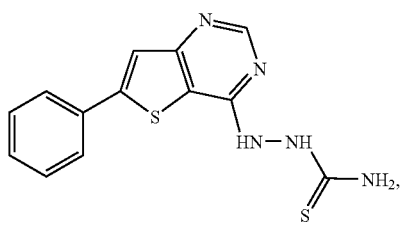
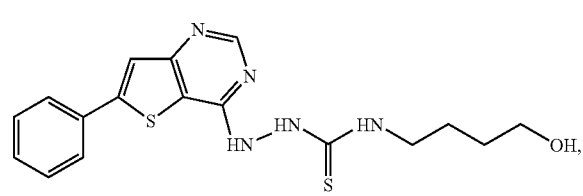
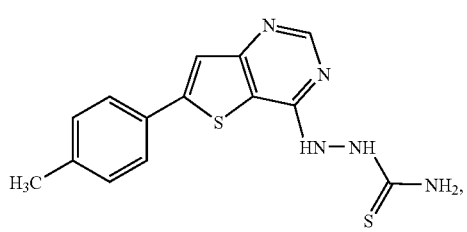
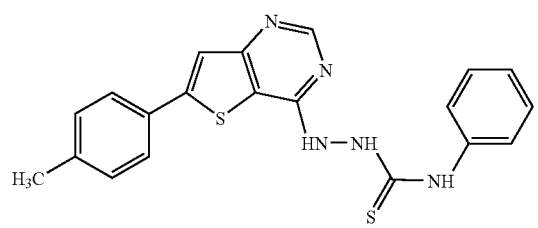
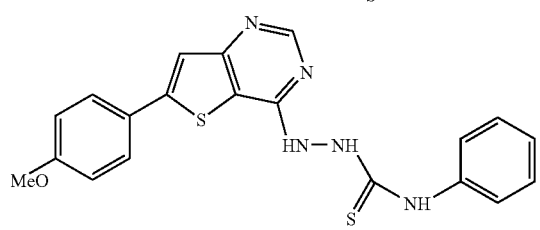
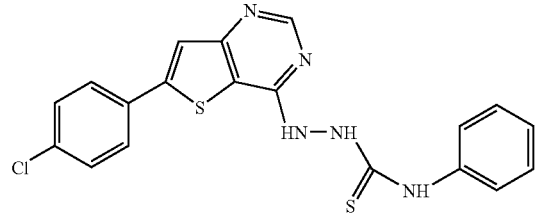
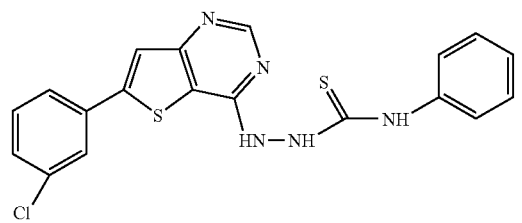
-continued
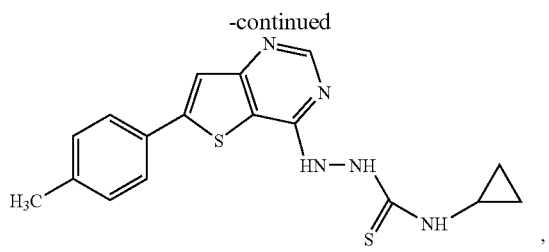
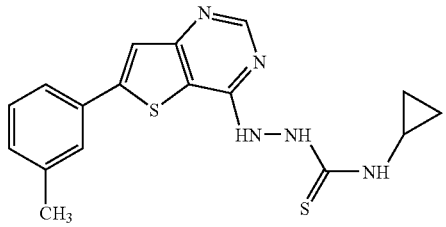
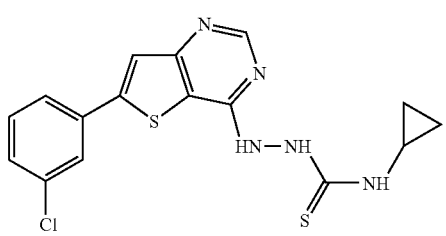
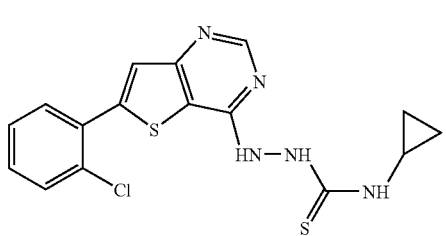
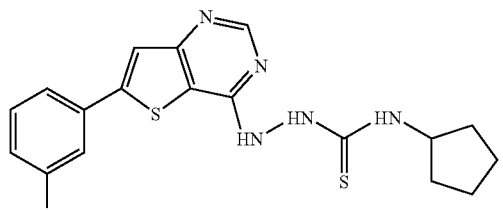
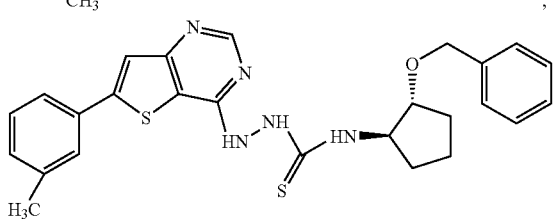
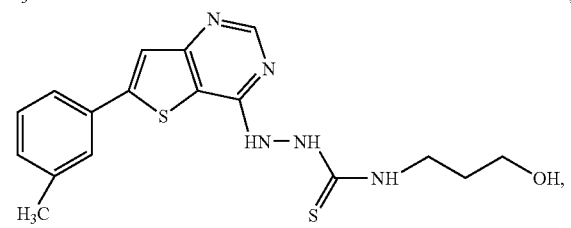

-continued
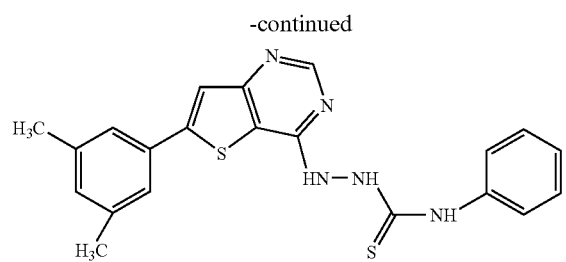
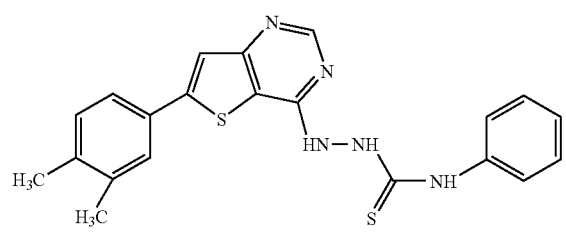
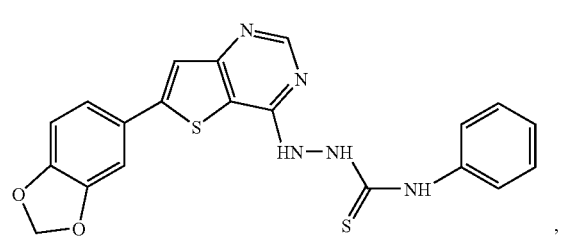
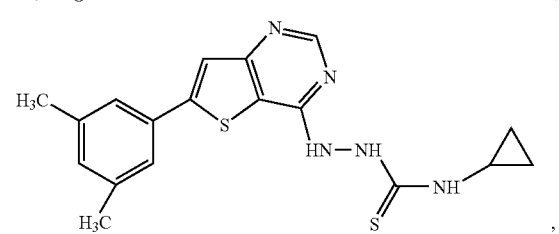
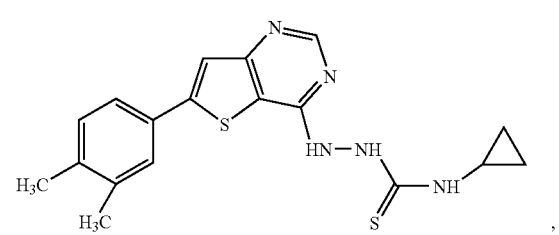
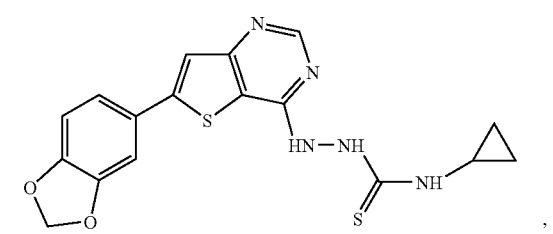
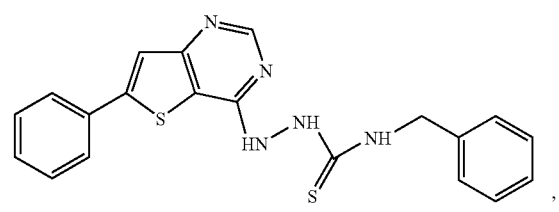
,
-continued
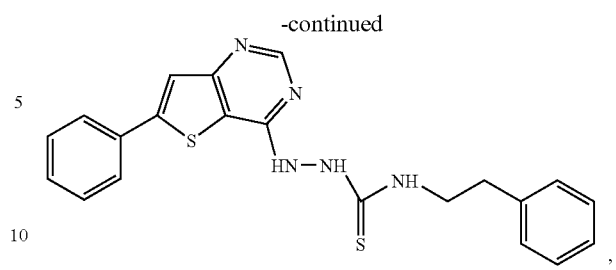
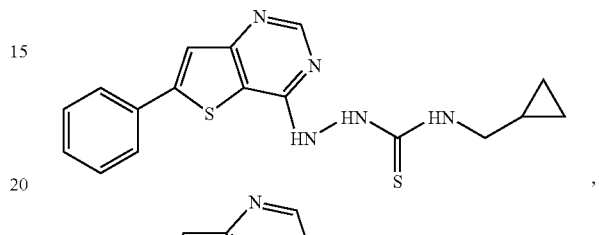
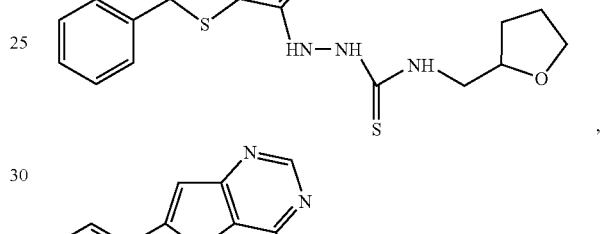
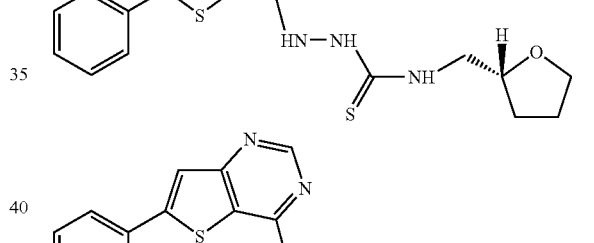
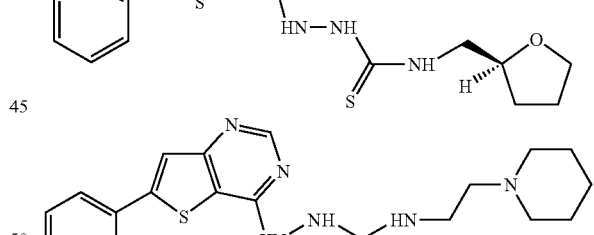
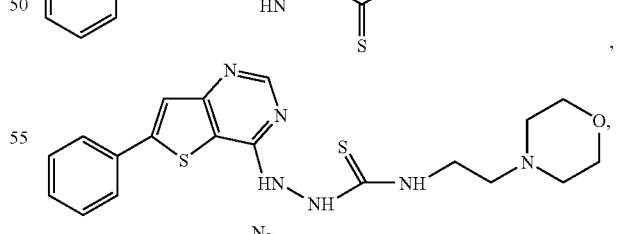
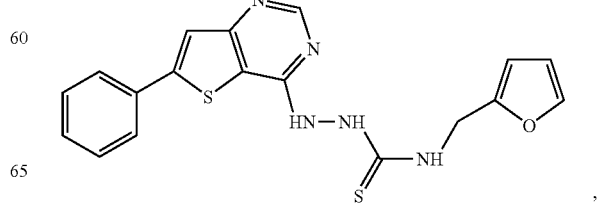
, -continued
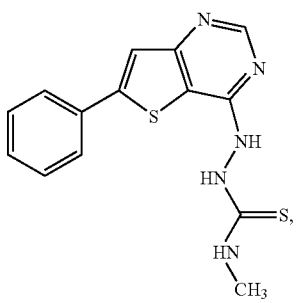
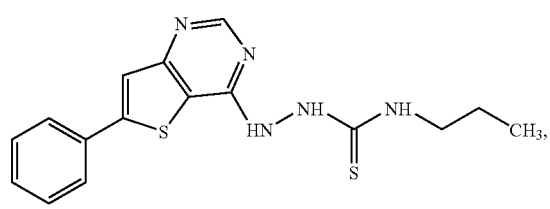
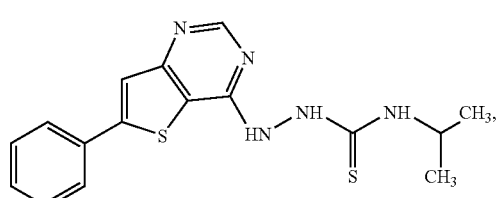
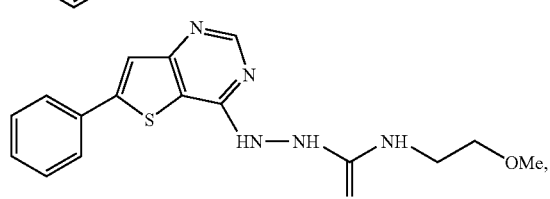
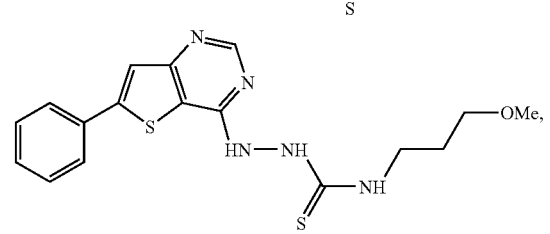
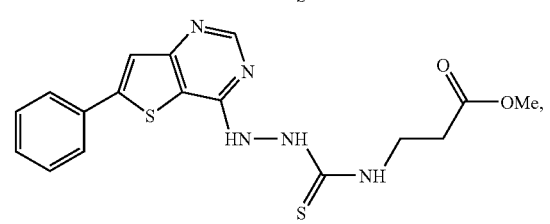
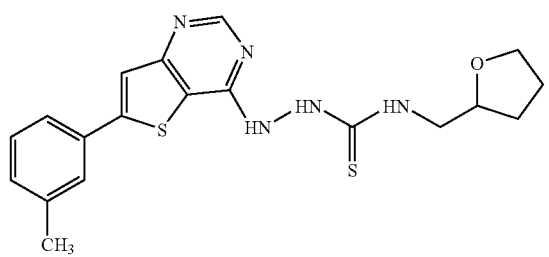
-continued
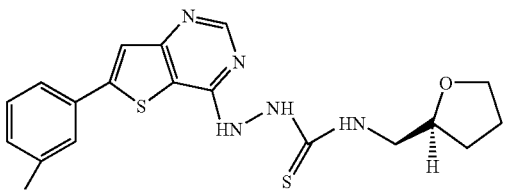
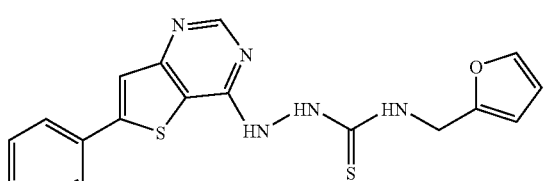
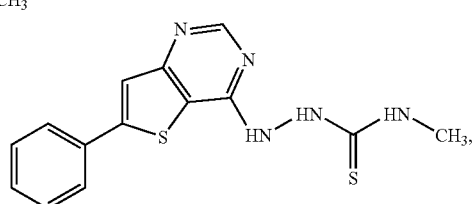
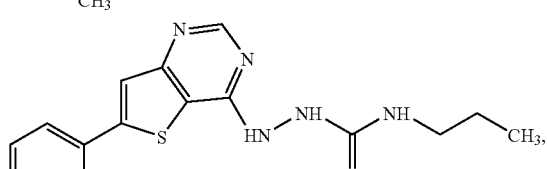
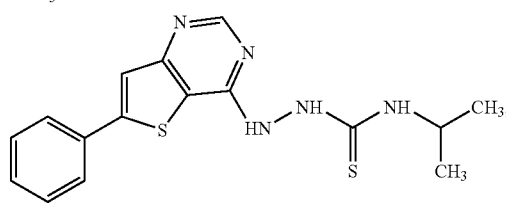
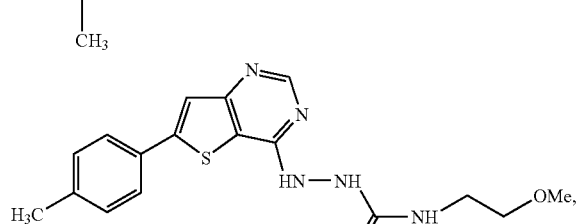
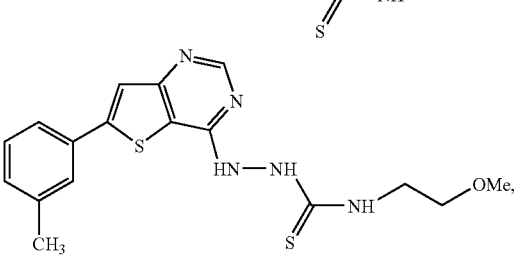

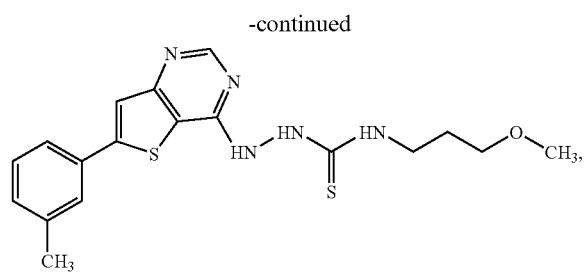
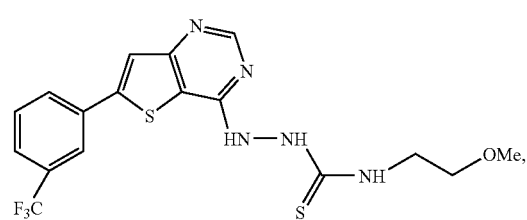
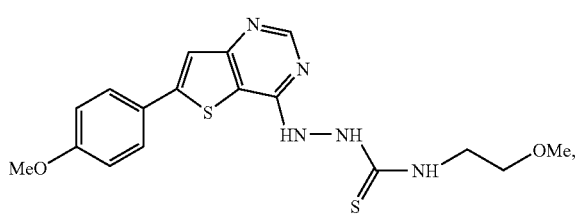
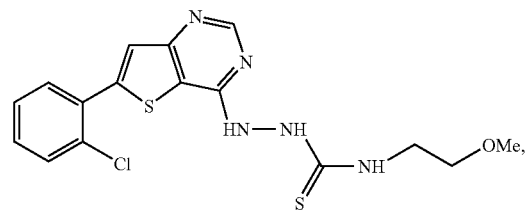
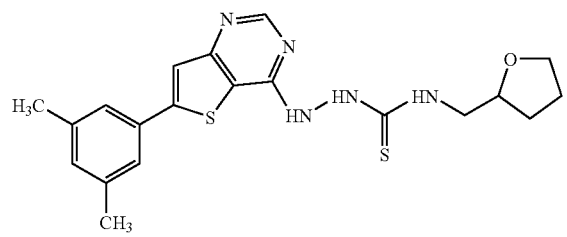
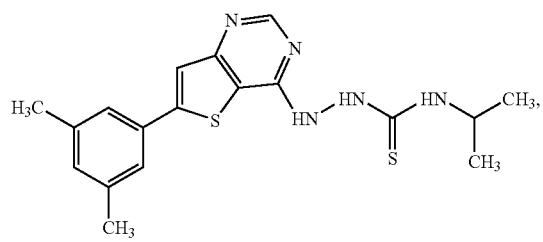
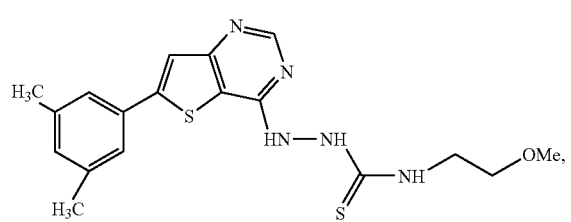
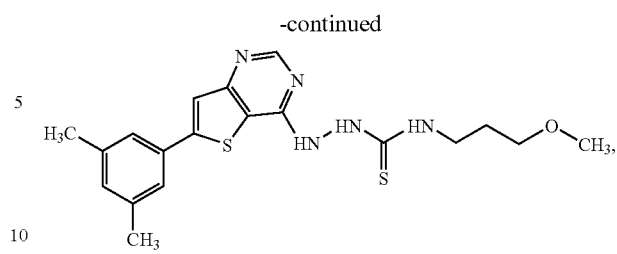
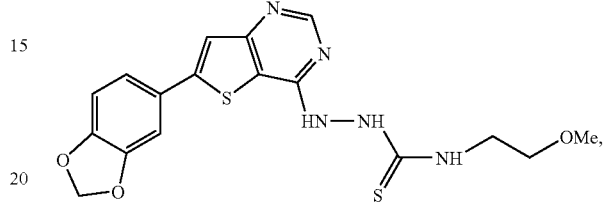
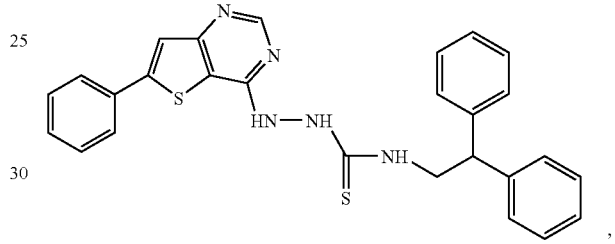
and their pharmaceutically acceptable salts.
17. A compound of claim 16 selected from the group consisting of:
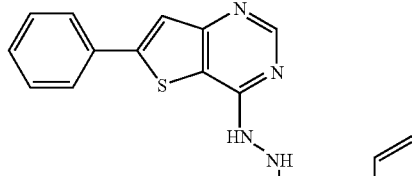
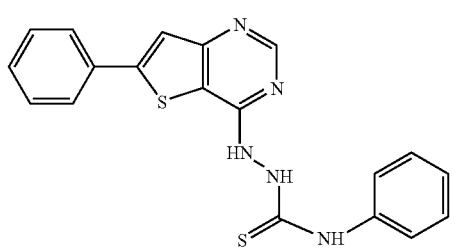
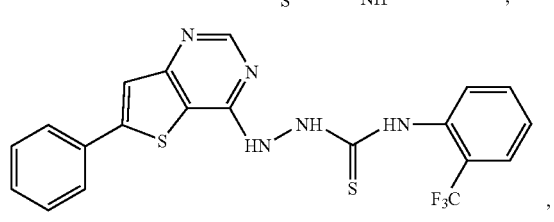

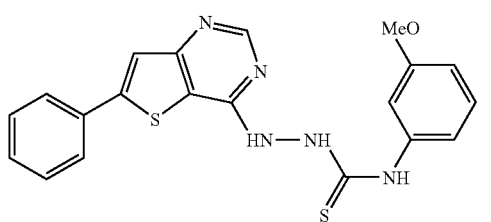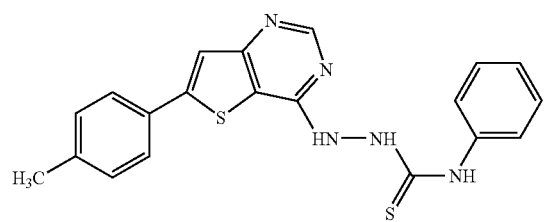

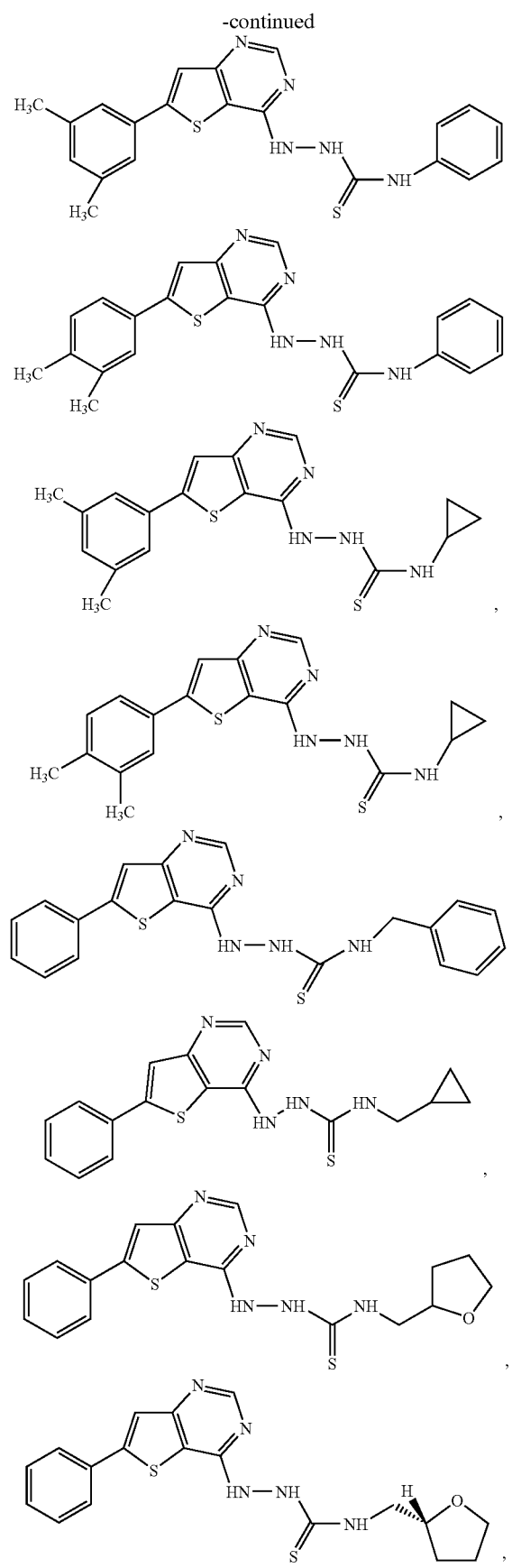
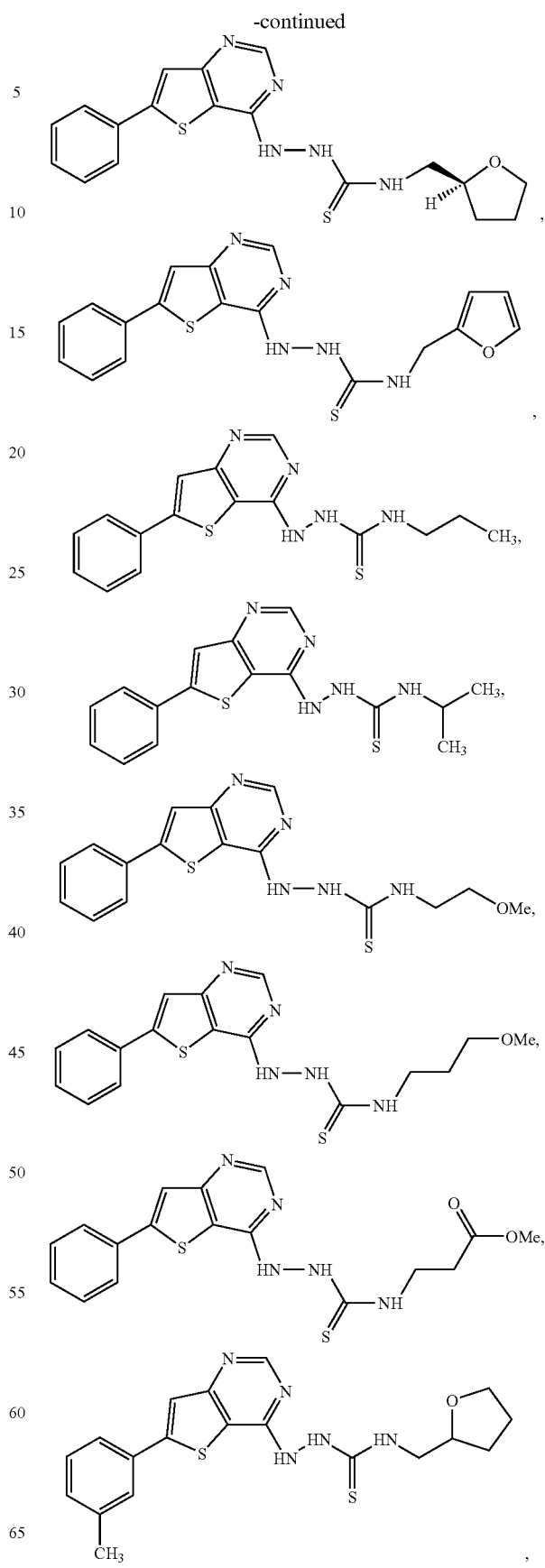

-continued
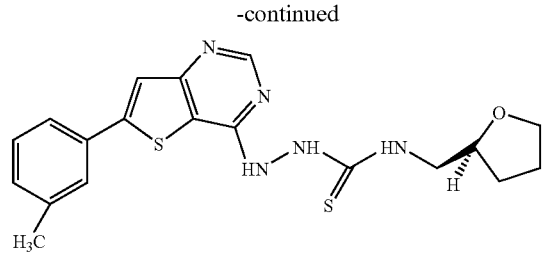
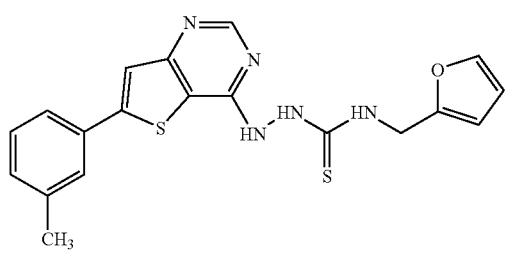
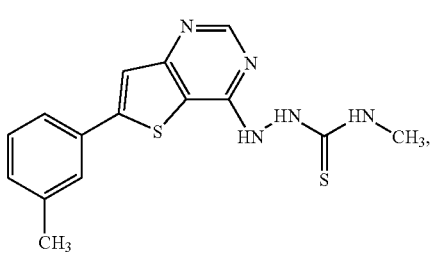
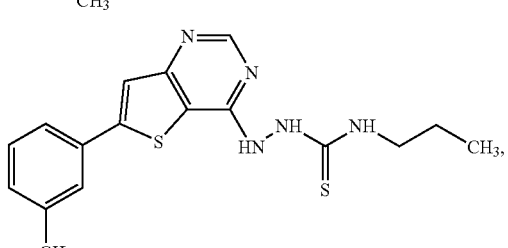
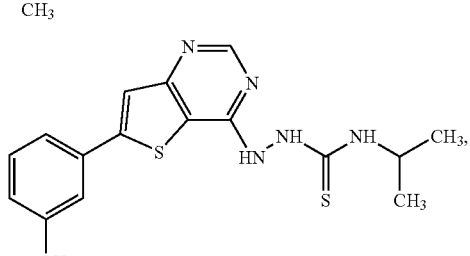
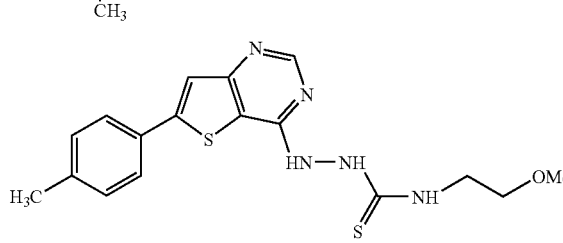
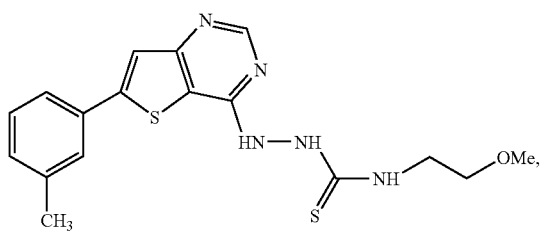
-continued
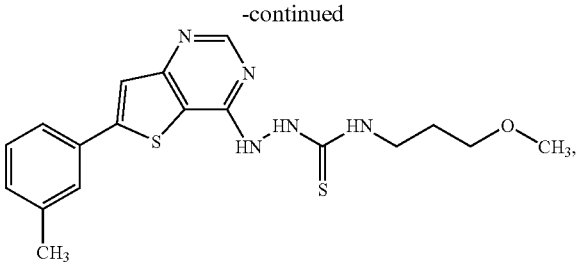
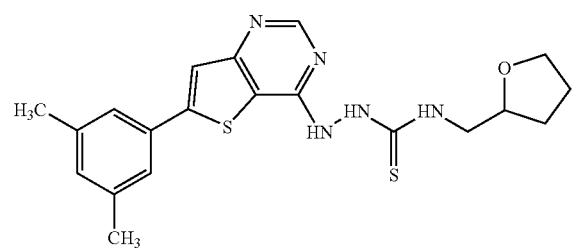
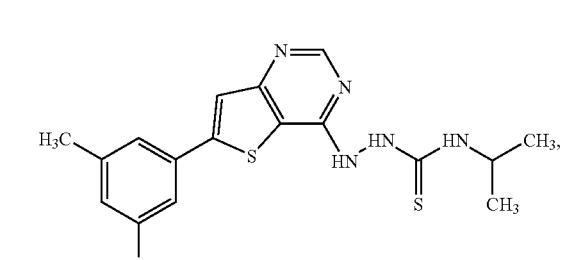
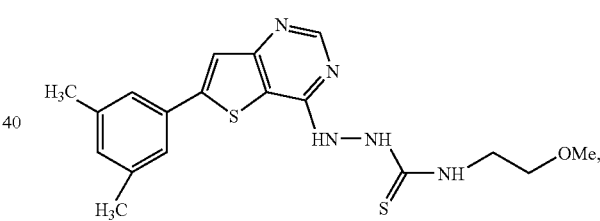
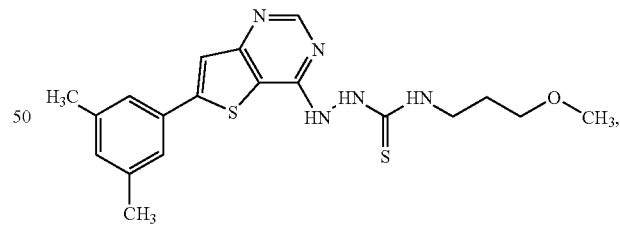
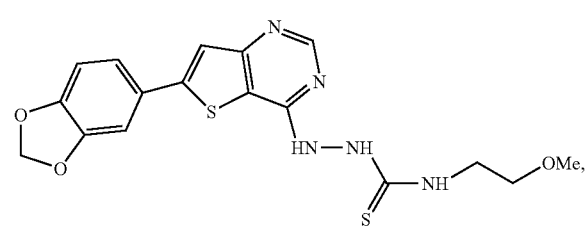

18. A compound of claim 17 selected from the group consisting of:
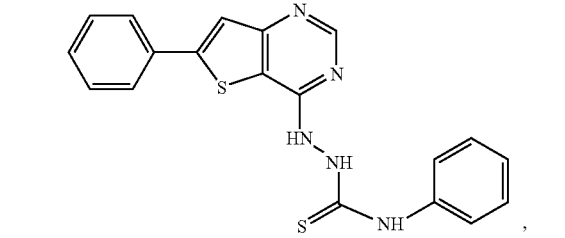
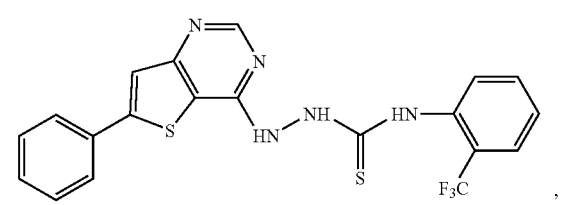
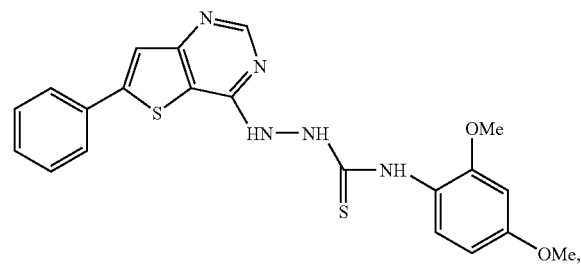
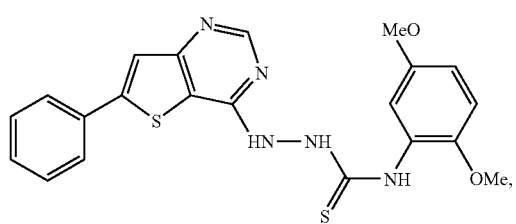
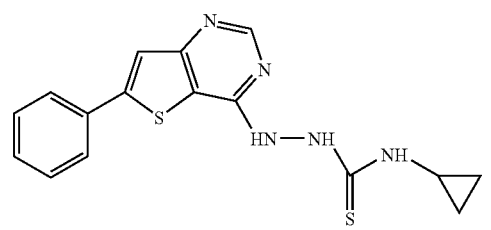
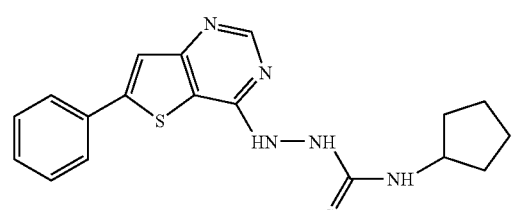
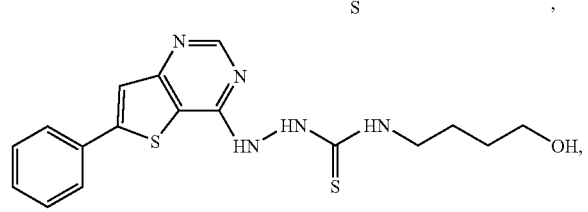
-continued
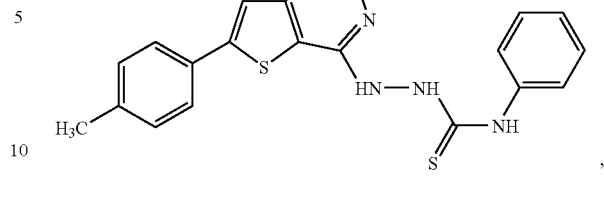
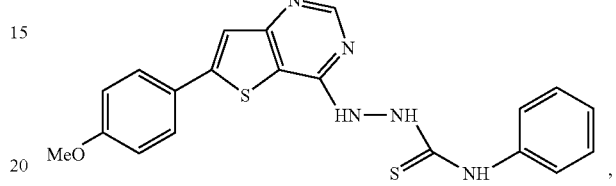
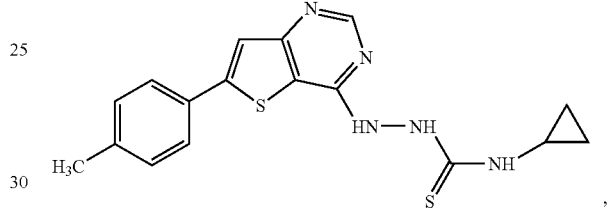
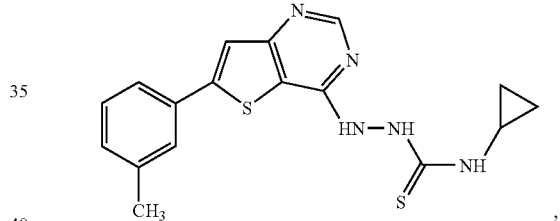
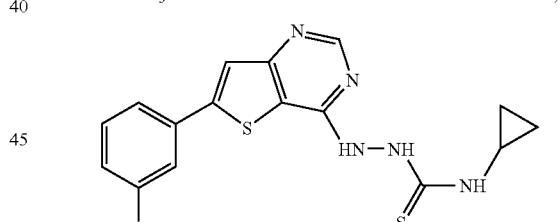
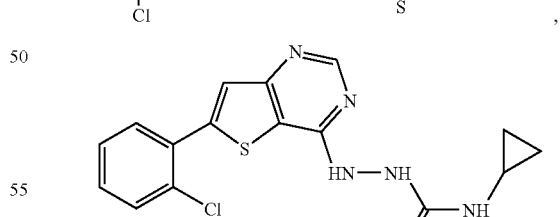
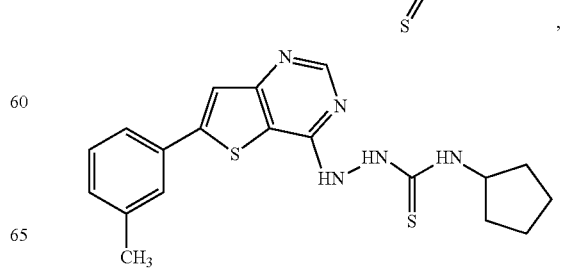

-continued
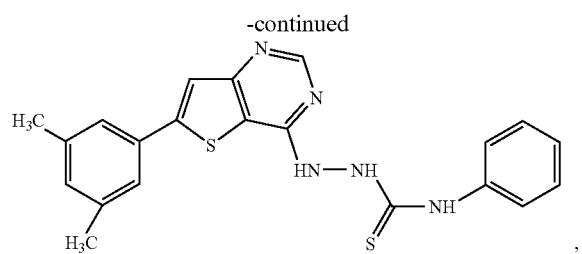,
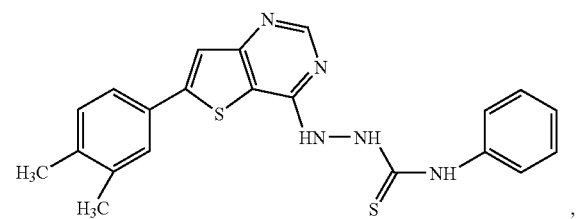,
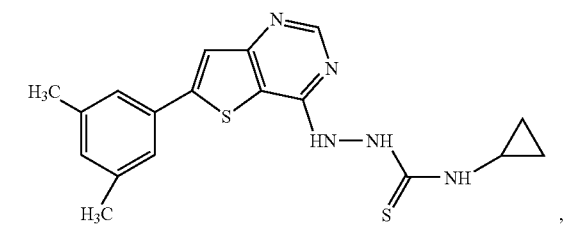,
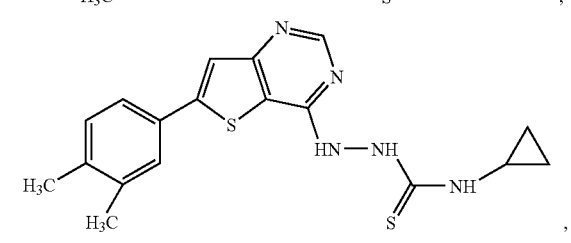,
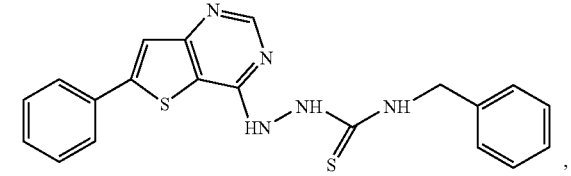,
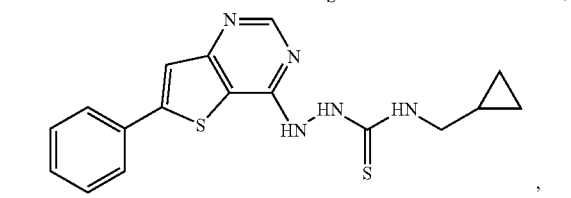,
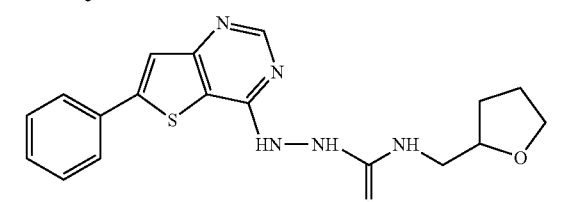,
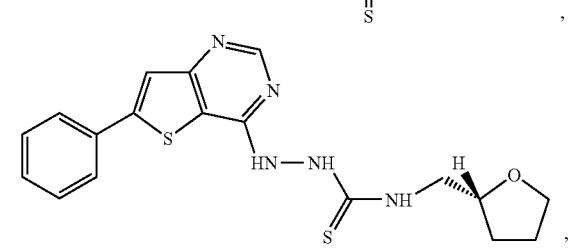,
-continued
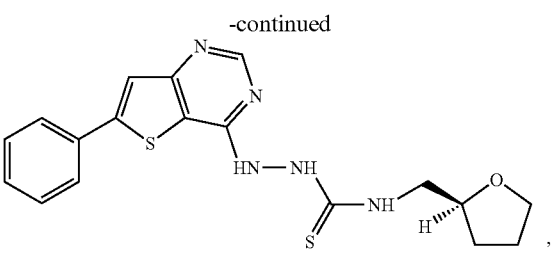,
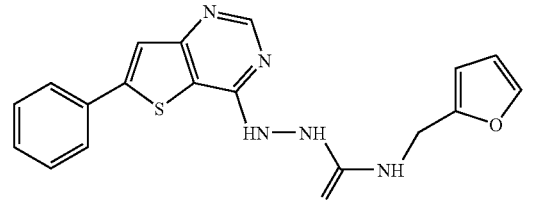,
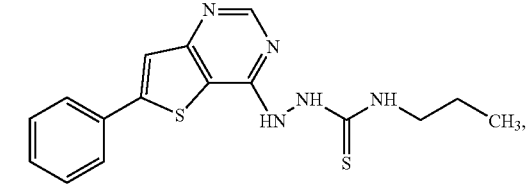,
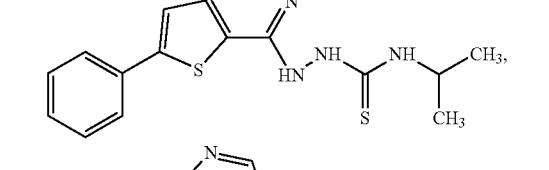,
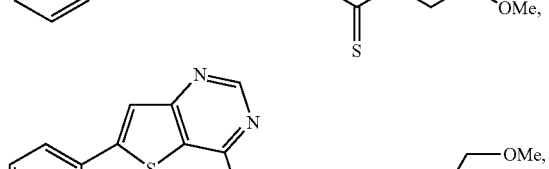,
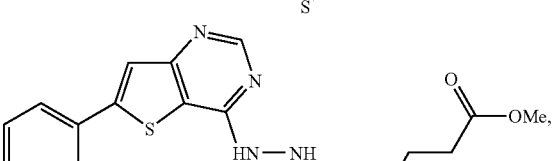,
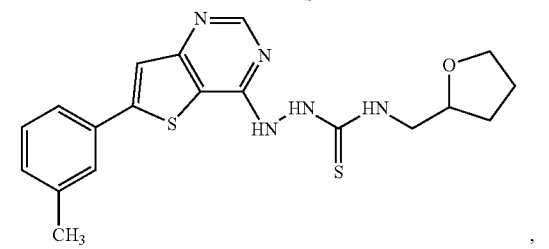,

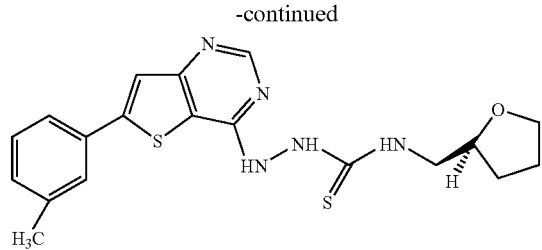
,
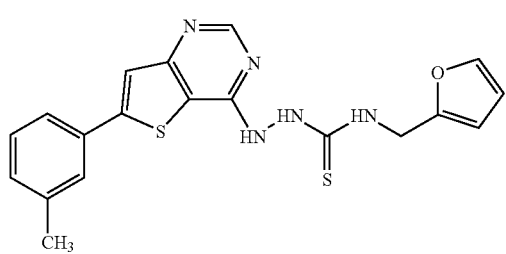
,
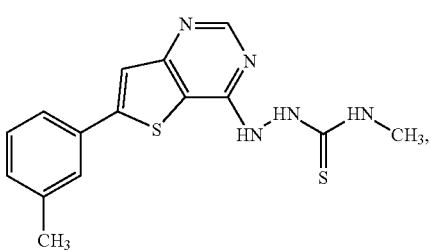
,
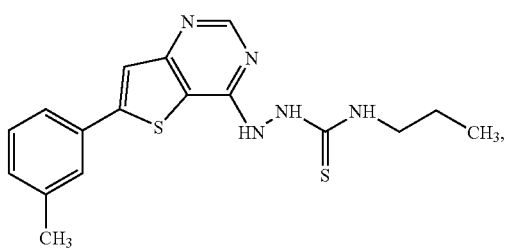
,
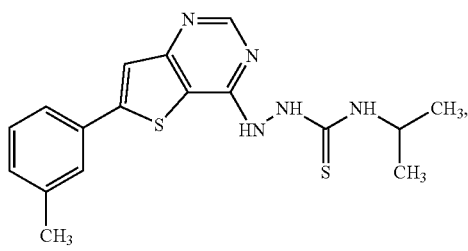
,
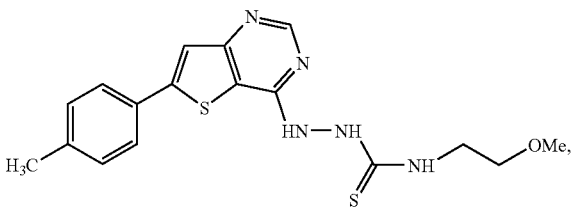
,
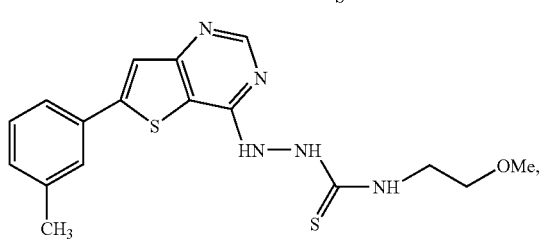
,
and their pharmaceutically acceptable salts.
19. A pharmaceutical composition comprising the compound of claim 1 and a pharmaceutical acceptable carrier, excipient, or diluent.
20. A method of inhibiting tubulin polymerization in a mammal comprising administering an effective amount of the compound of any one of claims 1–18 to said mammal.

21. A method of inhibiting cell proliferation comprising contacting cells with an effective amount of the compound of any one of claims 1–18.

22. A method for treating a patient with a cell proliferative disease or condition comprising administering to a patient in need thereof an effective amount of the compound of any one of claims 1–18, wherein the cell proliferative disease or condition is lung cancer.

* * * * *